(12) United States Patent
Kawahata et al.

(10) Patent No.: US 9,656,995 B2
(45) Date of Patent: May 23, 2017

(54) TRIAZINE DERIVATIVE

(71) Applicant: Carna Biosciences, Inc., Kobe-Shi, Hyogo (JP)

(72) Inventors: Wataru Kawahata, Kobe (JP); Tokiko Asami, Kobe (JP); Masaaki Sawa, Kobe (JP); Yuko Asamitsu, Kobe (JP); Takayuki Irie, Kobe (JP); Takahiro Miyake, Kobe (JP); Takao Kiyoi, Kobe (JP)

(73) Assignee: CARNA BIOSCIENCES, INC., Hyogo (JP)

(*) Notice: Subject to any disclaimer, the term of this patent is extended or adjusted under 35 U.S.C. 154(b) by 0 days.

(21) Appl. No.: 14/907,396

(22) PCT Filed: Jul. 15, 2014

(86) PCT No.: PCT/JP2014/068752
§ 371 (c)(1),
(2) Date: Jan. 25, 2016

(87) PCT Pub. No.: WO2015/012149
PCT Pub. Date: Jan. 29, 2015

(65) Prior Publication Data
US 2016/0168122 A1 Jun. 16, 2016

(30) Foreign Application Priority Data

Jul. 26, 2013 (JP) .................. 2013-155331
Sep. 11, 2013 (JP) .................. 2013-187987
Mar. 31, 2014 (JP) .................. 2014-073227

(51) Int. Cl.
*C07D 401/14* (2006.01)
*C07D 403/14* (2006.01)
*A61K 31/53* (2006.01)
*A61P 19/02* (2006.01)

(52) U.S. Cl.
CPC ............ *C07D 401/14* (2013.01); *A61K 31/53* (2013.01); *C07D 403/14* (2013.01)

(58) Field of Classification Search
CPC ..... C07D 401/14; C07D 403/14; A61K 31/53
USPC ......................... 544/204, 209; 514/241, 245
See application file for complete search history.

(56) References Cited

U.S. PATENT DOCUMENTS

2015/0011751 A1* 1/2015 Kawahata ............... A61K 31/53
540/544

FOREIGN PATENT DOCUMENTS

| JP | 2011-526279 A | 10/2011 |
| JP | 2012-519200 A | 8/2012 |
| WO | 2013/133367 A1 | 9/2013 |
| WO | 2013/161848 A1 | 10/2013 |

OTHER PUBLICATIONS

Whang et al., Drug Discovery Today, pp. 1-5, 2014.*
Akinleye et al. Journal of Hematology & Oncology 2013, 6:59.*
Chakravarty et al. Clinical Immunology (2013) 148, 66-78.*
Int'l Search Report issued Oct. 7, 2014 in Int'l Application No. PCT/JP2014/068752.
Int'l Preliminary Report on Patentability issued Feb. 4, 2016 in Int'l Application No. PCT/JP2014/068752.
Halcomb, K. et al., "Btk regulates localization, in vivo activation, and class switching of anti-DNA B cells," Mol. Immunol., vol. 46, No. 2, pp. 233-241 (2008).
Jansson, L. et al., "Genes on the X chromosome affect development of collagen-induced arthritis in mice," Clin. Exp. Immunol., vol. 94, pp. 459-465 (1993).
Ellmeier, W. et al., "Tec family kinases: regulation of FceRI-mediated mast-cell activation," FEBS Journal, vol. 278, pp. 1990-2000 (2011).
Davis, E et al., "Chronic active B-cell-receptor signalling in diffuse large B-cell lymphoma," Nature, vol. 463, pp. 88-92 (2010).
Kurosaki, T., "Functional dissection of BCR signaling pathways," Current Opinion in Immunology, vol. 12, pp. 276-281 (2000).

(Continued)

*Primary Examiner* — Venkataraman Balasubramanian
(74) *Attorney, Agent, or Firm* — Panitch Schwarze Belisario & Nadel LLP

(57) ABSTRACT

The purpose of the present invention is to provide a novel triazine derivative of the formula (I):

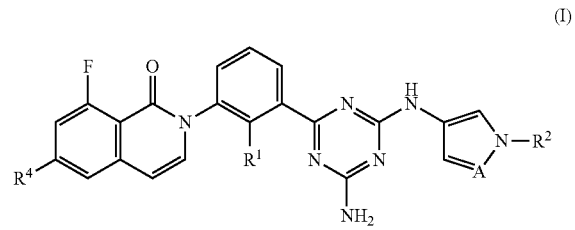

(I)

wherein $R^1$ represents a substituted or unsubstituted lower alkyl group, $R^2$ represents a hydrogen atom or a substituted or unsubstituted lower alkyl group, A represents a nitrogen atom or $C-R^3$, $R^3$ represents a hydrogen atom, a cyano group, a substituted or unsubstituted acyl group, a substituted or unsubstituted sulfonyl group, or a substituted or unsubstituted carbamoyl group, and $R^4$ represents a substituted or unsubstituted lower alkyl group, or a substituted or unsubstituted cycloalkyl group, or a pharmaceutically acceptable salt thereof.

14 Claims, 4 Drawing Sheets

(56) References Cited

OTHER PUBLICATIONS

Satterthwaite, A. et al., "The role of Bruton's tyrosine kinase in B-cell development and function: a genetic perspective," Immunological Reviews, vol. 175, pp. 120-127 (2000).

* cited by examiner

TRIAZINE DERIVATIVE

CROSS-REFERENCE TO RELATED APPLICATION

This application is a Section 371 of International Application No. PCT/JP2014/068752, filed Jul. 15, 2014, which was published in the Japanese language on Jan. 29, 2015 under International Publication No. WO 2015/012149 A1, and the disclosure of which is incorporated herein by reference.

TECHNICAL FIELD

The present invention relates to a pharmaceutical, and particularly to a novel triazine derivative having a BTK inhibitory effect, a prodrug or a pharmaceutically acceptable salt thereof.

BACKGROUND ART

Bruton's tyrosine kinase (BTK) is a member of the Tec family of non-receptor tyrosine kinases, and is an important signaling enzyme which is expressed in all hematopoietic cell types except for T lymphocytes and natural killer cells. BTK is an important control factor associated with survival, differentiation, proliferation and activation of B-cells, and takes an important role in signaling of B-cells (Non-Patent Documents 1 and 2). A B-cell receptor (BCR) of the cell surface signals into cells through BTK existing in the downstream of BCR and, therefore, it is considered that abnormal activation of the signaling pathway of B-cells accelerates proliferation and survival of cancer cells of B-cell lymphoma, chronic lymphocytic leukemia and the like (Non-Patent Document 3). It is known that BTK also plays an important role in the signal pathway of a large number of other cells, and it is said that BTK is involved in allergic diseases, self-immune diseases, inflammatory diseases and the like (Non-Patent Document 1). For example, it is known that BTK plays an important role for signaling of a high affinity IgE receptor (FcεRI) in mast cells, and degranulation decreases and the production of proinflammatory cytokines decreases in BTK-deficient mast cells (Non-Patent Document 4). It is suggested that BTK is involved in systemic lupus erythematosus (SLE) in a test of a BTK-deficient mouse (Non-Patent Document 5). Furthermore, the BTK mutant mouse exhibits resistance to the onset of collagen-induced arthritis (Non-Patent Document 6). Therefore, the compound having a BTK inhibitory activity is useful for the treatment of diseases which are involved in BTK signaling, for example, cancer, B-cell lymphoma, and chronic lymphocytic leukemia, and is also useful for the treatment of allergic diseases, self-immune diseases and inflammatory diseases.

The compounds which having a BTK inhibitory effect mentioned above have been reported. (Patent Document 1)

PRIOR ART DOCUMENTS

Patent Documents

[Patent Document 1] WO 2013/133367

Non-Patent Documents

[Non-Patent Document 1] Satterthwaite, A. B. and Witte, O. N., Immunol. Rev., 2000, 175, 120-127

[Non-Patent Document 2] Kurosaki T., Curr. Opin. Immunol., 2000, 12, 276-281

[Non-Patent Document 3] Davis R. E. et al., Nature, 2010, 463, 88-92

[Non-Patent Document 4] Ellmeier W. et al., FEBS J., 2011, 278, 1990-2000

[Non-Patent Document 5] Halcomb K. E., Mol. Immunol., 2008, 46(2), 233-241

[Non-Patent Document 6] Jansson L. and Holmdahl R., Clin. Exp. Immunol., 1993, 94, 459-465

SUMMARY OF INVENTION

Problems to be Solved by the Invention

An object of the present invention is to provide a pharmaceutical, particularly a novel triazine derivative having a BTK inhibitory effect, its prodrug or a pharmaceutically acceptable salt thereof.

Means of Solving the Problems

The present invention is achieved by the following (1) to (2):

(1) A triazine derivative represented by the following formula (I):

[Chemical Formula 1]

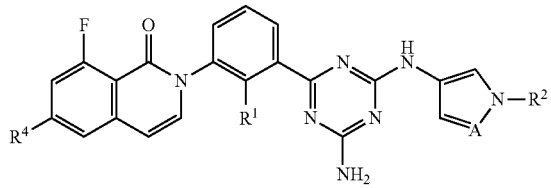

wherein
R$^1$ represents a substituted or unsubstituted lower alkyl group,
R$^2$ represents a hydrogen atom or a substituted or unsubstituted lower alkyl group,
A represents a nitrogen atom or C—R$^1$,
R$^3$ represents a hydrogen atom, cyano group, a substituted or unsubstituted acyl group, a substituted or unsubstituted sulfonyl group, or a substituted or unsubstituted carbamoyl group,
R$^4$ represents a substituted or unsubstituted lower alkyl group, a substituted or unsubstituted cycloalkyl group,
or a pharmaceutically acceptable salt thereof.

(2) A triazine derivative according to (1),
wherein
R$^1$ represents —CH$_2$OR$^5$,
R$^5$ represents a substituted or unsubstituted acyl group,
or a pharmaceutically acceptable salt thereof.

Effect of the Invention

The present inventors have intensively studied so as to achieve the above object and found that a novel triazine derivative represented by formula (I) shown above, its prodrug and a pharmaceutically acceptable salt thereof have an excellent BTK inhibitory effect and an excellent inhibitory effect in an animal model of collagen-induced arthritis, and thus completed the present invention. The compound provided by the present invention is useful as a preventive or therapeutic pharmaceutical (pharmaceutical composition) or its prodrug for diseases which are known to be involved in abnormal cell response through BTK, for example, self-immune diseases, inflammatory diseases, bone diseases, and cancers such as lymphoma. The compound is also useful, as a BTK inhibitor, for reagents to be used in tests and researches.

DESCRIPTION OF EMBODIMENTS

Figure 1:
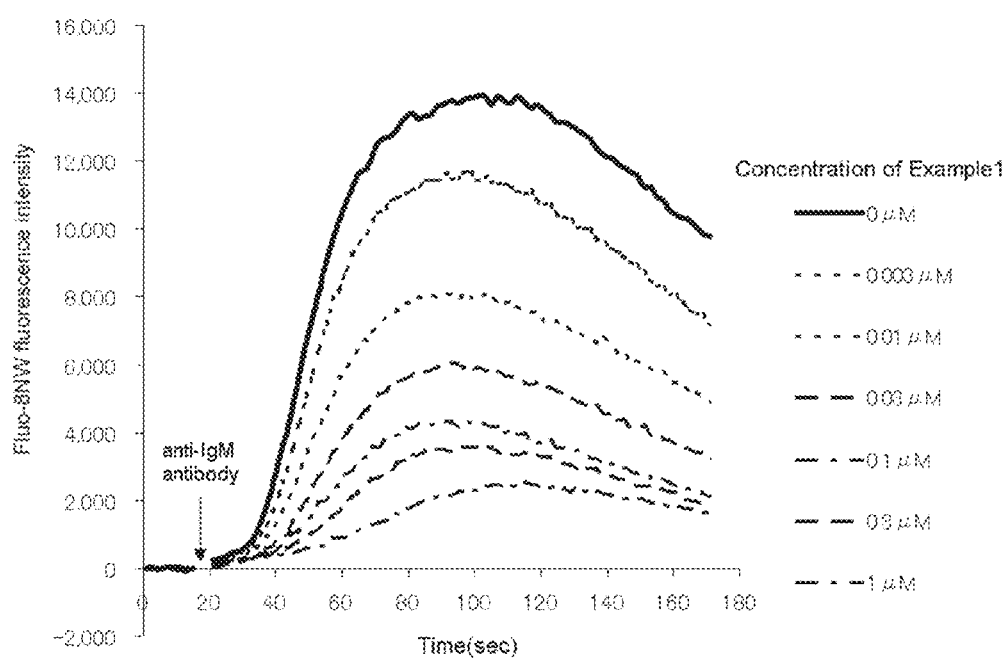
FIG. 1 shows that the compound of Example 1 inhibits the BCR signal in the Ramos cells in a concentration dependent manner and inhibits the flux of calcium into the cells (Test Example 3).

The present invention will be described in detail below.
A novel triazine derivative of the present invention is a compound represented by formula (I) shown below:

[Chemical Formula 2]

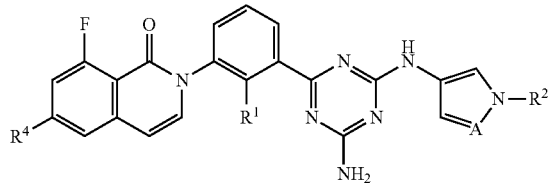

(I)

wherein
$R^1$ represents a substituted or unsubstituted lower alkyl group,
$R^2$ represents a hydrogen atom or a substituted or unsubstituted lower alkyl group,
A represents a nitrogen atom or C—$R^3$,
$R^3$ represents a hydrogen atom, cyano group, a substituted or unsubstituted acyl group, a substituted or unsubstituted sulfonyl group, or a substituted or unsubstituted carbamoyl group,
$R^4$ represents a substituted or unsubstituted lower alkyl group, a substituted or unsubstituted cycloalkyl group.
In formula (I) shown above,
A lower alkyl group moiety of the substituted or unsubstituted lower alkyl group may be any of linear, branched or cyclic alkyl groups having 1 to 3 carbon atoms, and specific examples thereof include a methyl group and an isopropyl group, etc.
A cycloalkyl group moiety of the substituted or unsubstituted cycloalkyl group may be cyclic alkyl groups having 3 to 6 carbon atoms, and specific examples thereof include a cyclopropyl group and a cyclobutyl group, etc.

An acyl group moiety of the substituted or unsubstituted acyl group may be any of linear, branched or cyclic alkyl groups connected to a carbonyl group, and specific examples of the acyl group moiety of the substituted or unsubstituted acyl group include a formyl group, an acetyl group and a propionyl group, a octanoyl group, a dodecanoyl group, a pivaloyl group, a cyclopropylcarbonyl group and a benzoyl group etc.

Examples of the sulfonyl group moiety of the substituted or unsubstituted sulfonyl group include a methylsulfonyl group, an ethylsulfonyl group, etc.

Examples of the carbamoyl group moiety of the substituted or unsubstituted carbamoyl group include a methylcarbamoyl group, an ethylcarbamoyl group and a dimethylcarbamoyl group, etc.

A substituent of the substituted or unsubstituted lower alkyl group, the substituted or unsubstituted cycloalkyl group, the substituted or unsubstituted acyl group, the substituted or unsubstituted sulfonyl group, or the substituted or unsubstituted carbamoyl group may be the same or different when the above group have two or more substituents, and the group may be substituted with one, or two or more of any kind of substituent(s) at any position which is chemically allowable. Examples of the substituent include a halogen atom, a substituted or unsubstituted alkyl group, a substituted or unsubstituted alkoxy group, a substituted or unsubstituted amino group, a nitro group, a cyano group, a hydroxy group, a substituted or unsubstituted alkylamino group, a substituted or unsubstituted carbamoyl group, a carboxyl group, a formyl group, an acetyl group, a mesyl group, a benzoyl group, a substituted or unsubstituted acylamino group, and a substituted or unsubstituted acyloxy group, etc.

Isomers may exist in the compound (I) of the present invention, depending on the kind of the substituent. In the present description, the isomers may be described by a chemical structure of only one form thereof, but the present invention includes all isomers (geometrical isomer, optical isomer, tautomer, etc.) which can be structurally formed, and also includes isomers alone, or a mixture thereof.

Examples of the pharmaceutically acceptable salt of the compound (I) of the present invention include inorganic acid salts with hydrochloric acid, sulfuric acid, carbonic acid, and phosphoric acid; and organic acid salts with fumaric acid, maleic acid, methanesulfonic acid, and p-toluenesulfonic acid. The present invention also includes ammonium salts, in addition to alkali metal salts with sodium and potassium; alkaline earth metal salts with magnesium and calcium; organic amine salts with lower alkylamine and lower alcoholamine; and basic amino acid salts with lysine, arginine, and ornithine.

Unless indicated otherwise, 'the compound (I) of the present invention' also includes its prodrug.

The compound (I) and a pharmaceutically acceptable salt thereof in the present invention can be produced, for example, by methods shown below. When a defined group may be chemically affected under the conditions of an exemplified method in the production method shown below, or is unsuited for use to carry out the method, it is possible to easily produce them by a method which is usually used in organic synthetic chemistry, for example, a method of applying means such as protection or deprotection of a functional group [T. W. Greene, Protective Groups in Organic Synthesis 3rd Edition, John Wiley & Sons, Inc., 1999]. If necessary, the order of a reaction step such as introduction of substituents can also be changed.

Meanings of abbreviations and symbols used in the following description are as follows.
DCM: dichloromethane
THF: tetrahydrofuran
DIEA: N,N-diisopropylethylamine
DMF: N,N-dimethylformamide
DMSO: dimethyl sulfoxide
CDCl$_3$: deuterated chloroform

[Method for Production of the Compound (I) of the Present Invention]

The compound of the present invention represented by formula (I) can be produced, for example, according to Scheme 1:

[Scheme 1]

[Chemical Formula 3]

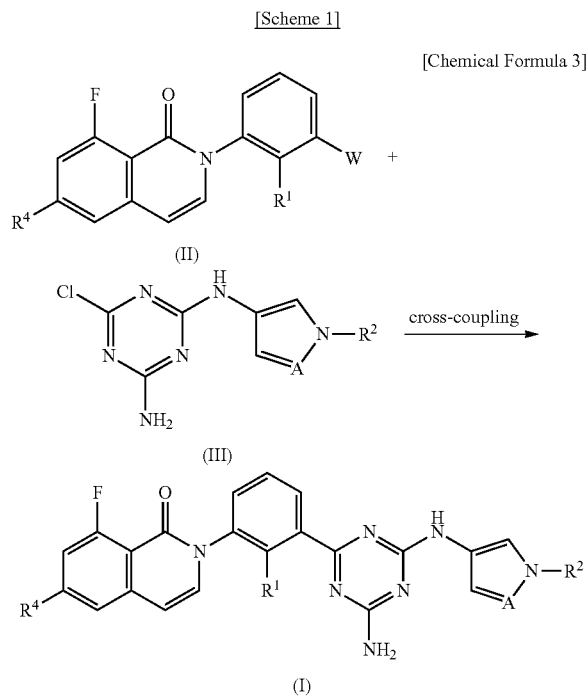

wherein R$^1$, R$^2$, R$^4$, and A are as defined above, and W represents a boronyl group or a boronic acid ester group.

The compound (I) of the present invention can be produced by a cross-coupling reaction such as Suzuki coupling reaction, using a compound (II) and a compound (III) (with respect to the conditions of the Suzuki coupling reaction, see literatures, for example, N. Miyaura et al., J. Am. Chem. Soc., 107, 972 (1985)., N. Miyaura, A. Suzuki, Chem. Rev. 95, 2457 (1995)). That is, the reaction can be carried out in the presence of a metal catalyst such as palladium or nickel, if necessary, using a base and additives. Examples of a solvent used in the reaction include THF, dioxane, toluene, dimethoxyethane, methanol, ethanol, and acetonitrile. It is also suitable to use two or more kinds of these solvents, or to use them in combination with water. The solvent is preferably a mixed solvent of THF and water, or a mixed solvent of toluene, methanol and water, or dioxane. The compound (II) is preferably used in an equivalent or excess amount, and more preferably in an amount of from 1 equivalent to 10 equivalents, based on the compound (III). If necessary, a base may be added so as to accelerate the reaction, and sodium carbonate, cesium carbonate, and potassium carbonate are usually used as the base. The amount of the base to be used is from 1 equivalent to 10 equivalents, and preferably from 1 equivalent to 5 equivalents, based on the compound (III). It is possible to use, as a metal catalyst, a commercially available palladium catalyst (for example, PdCl$_2$(dppf), Pd$_2$(dba)$_3$, Pd(PPh$_3$)$_4$, etc.) which is used in the cross-coupling, and the catalyst is preferably used in a catalytic amount, that is, an amount of from 0.1 equivalent to 0.5 equivalent based on the compound (III).

If necessary, additives can be added so as to accelerate the reaction. The additive includes, for example, rac-BINAP and can be used in the amount of from 0.01 equivalent to 1 equivalent based on the compound (III). It is possible to synthesize the product by reacting at a temperature ranging from 0° C. to 200° C. for several minutes to several days, and preferably from 10° C. to 100° C. for 1 hour to 36 hours. It is also possible to synthesize the product by reacting under the temperature condition of from 60° C. to 150° C. for several minutes to several hours, using a microwave synthesis equipment.

The compound (II) used as a starting material of Scheme 1 can be produced, for example, by the method shown in Scheme 2:

[Scheme 2]

[Chemical Formula 4]

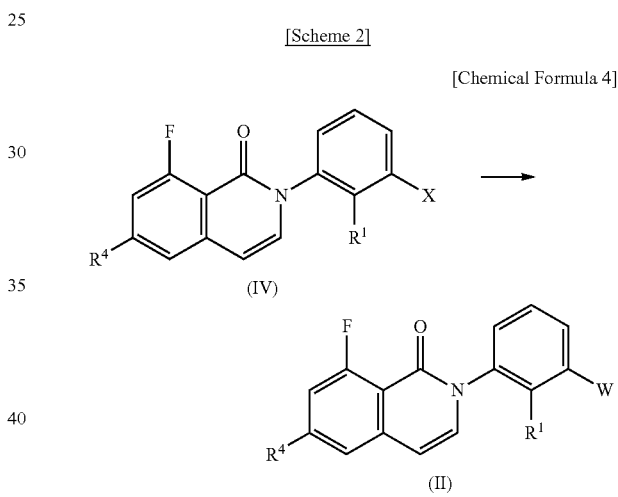

wherein R$^1$, R$^4$ and W are as defined above, and X represents a halogen.

The compound (II) can be produced by activating the compound (IV) with n-butyllithium, and then reacting the activated compound with a boric acid ester. That is, the compound (II) can be obtained by lithiation of the compound (IV) with 1 to 5 molar equivalents, and preferably 1 to 1.5 molar equivalents of n-butyllithium, and reacting the lithiated compound with 1 to 5 molar equivalents, and preferably 1 to 1.5 molar equivalents of a boric acid ester.

Any solvent may be used as long as it is inert to the reaction, and THF can be preferably used though it is not particularly limited.

The reaction temperature is usually from −100° C. to −30° C., and preferably from −80° C. to −60° C. The reaction time is not particularly limited, but is usually exemplified by hours from 0.1 hour to 12 hours, preferably from 0.2 hour to 6 hours.

The compound (II) can also be obtained by reacting the compound (IV) with 1 to 5 molar equivalents, and preferably 1 to 1.5 molar equivalents of metallic magnesium and a catalytic amount of iodine in an ether-based solvent at a temperature of from −10° C. to a boiling point of the solvent to be used to obtain a Grignard reagent, and then reacting the Grignard reagent with 1 to 5 molar equivalents, preferably 1 to 1.5 molar equivalents of a boric acid ester. The reaction temperature is usually from −30° C. to −100° C., preferably from −60° C. to −80° C. The reaction time is not particularly limited, but usually exemplified by hours from 0.1 hour to 12 hours, preferably from 0.2 hour to 6 hours.

Furthermore, the compound (II) can be obtained by subjecting the compound (IV) and 1 to 5 molar equivalents, preferably 1 to 3 molar equivalents of a diboron ester to a coupling reaction in the presence of a metal catalyst such as palladium and nickel and a base in an organic solvent.

It is possible to use, as the metal catalyst, a commercially available palladium catalyst (for example, $PdCl_2(dppf)$, $Pd_2(dba)_3$, $Pd(PPh_3)_4$, etc.) which is used in the cross-coupling, and the catalyst is preferably used in a catalytic amount, that is, an amount of from 0.1 equivalent to 0.5 equivalent based on the compound (IV) to be used in the cross-coupling. Potassium acetate is usually used as the base. The amount of the base to be used is from 1 equivalent to 10 equivalents, preferably from 1 equivalent to 5 equivalents based on the compound (IV).

Any solvent may be used as long as it is inert to the reaction, and dioxane can be preferably used, though it is not particularly limited.

The reaction temperature is usually from 0° C. to 200° C., preferably from 10° C. to 100° C. The reaction time is not particularly limited, but the reaction time of from 0.2 hour to 48 hours, preferably from 1 hour to 36 hours is exemplified as a preferable example.

It is desired that any of these reactions are carried out in an inert gas (argon, nitrogen etc.) atmosphere, under anhydrous conditions.

The compound (IV) to be used as a starting material of Scheme 2 can be produced, for example, by the method shown in Scheme 3:

group of the compound (VI), appropriately combining methods to be usually used in organic synthetic chemistry. For example, it is possible to use protection or deprotection of a functional group, such as hydroxy or amino group of the compound (VI) [T. W. Greene, Protective Groups in Organic Synthesis 3rd Edition, John Wiley & Sons, Inc., 1999] and aldehyde derivative which is a hydroxy group-precursor of the compound (VI).

The reaction can be carried out at a temperature of from 80° C. to 200° C. for 0.5 hour to 200 hours, preferably from 100° C. to 150° C. for 1 hour to 100 hours. It is also possible to perform the reaction using microwave synthesis equipment.

It is possible to use, as the metal catalyst, a commercially available palladium catalyst (for example, $PdCl_2(dppf)$, $Pd_2(dba)_3$, $Pd(PPh_3)_4$, etc.) or copper(I) iodide which is used in the coupling reaction, and the catalyst is preferably used in a catalytic amount, that is, an amount of from 0.01 equivalent to 2 equivalents based on the compound (V) to be used in the coupling.

Examples of the base to be used include potassium carbonate, sodium carbonate, cesium carbonate and sodium hydrogen carbonate, and cesium carbonate and sodium hydrogen carbonate can be preferably used. The amount of the base to be used is from 1 molar equivalent to 10 molar equivalents, preferably from 2 molar equivalents to 5 molar equivalents, based on the compound (V). And if necessary, xantphos can be used as additive to the reaction in the amount of 0.1 equivalent to 0.5 equivalent based on the compound (V).

The compound (VI) can be obtained as a commercially available product, or can be obtained by a well-known procedure or the procedure according to it.

The compound (III) to be used as a starting material of Scheme 1 can be produced, for example, by the method shown in Scheme 4:

[Scheme 3]

[Chemical Formula 5]

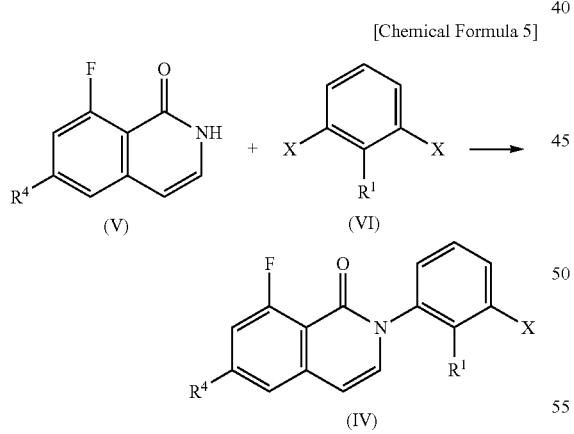

[Scheme 4]

[Chemical Formula 6]

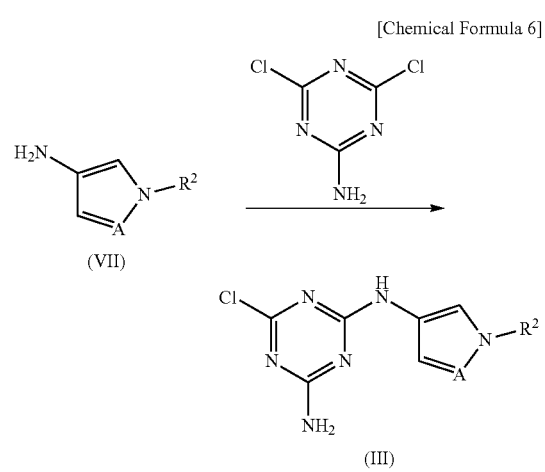

wherein $R^1$, $R^4$ and X are as defined above.

The compound (IV) can be obtained by reacting compound (V) with 1 to 5 molar equivalents, preferably 1.5 to 3 molar equivalents of compound (VI) in a polar solvent in the presence of metal catalyst and base.

Any solvent may be used as long as it is inert to the reaction, but dioxane can be preferably used, though is not particularly limited.

In the coupling reaction, the compound (IV) can also be produced by optionally protecting or deprotecting an $R^1$ wherein $R^2$ and A are as defined above.

The compound (III) can be obtained by reacting an amine (VII) with 1 to 5 molar equivalents, preferably 1 to 1.5 molar equivalents of 2-amino-4,6-dichloro-1,3,5-triazine in a polar solvent and, if necessary, in the presence of a base catalyst.

Any solvent may be used as long as it is inert to the reaction, but DMF and THF can be preferably used, though it is not particularly limited.

The reaction temperature is usually from 0° C. to 200° C., preferably from 10° C. to 100° C. The reaction time is not particularly limited and the reaction time of from 0.2 hour to 48 hours is usually exemplified, and the reaction time of from 1 hour to 36 hours is exemplified as a preferable examples.

2-Amino-4,6-dichloro-1,3,5-triazine, which is starting material of Scheme 4, can be obtained as commercially available product. An amine (VII) can be obtained as a commercially available product, or prepared by a well-known procedure or the procedure according to it.

The compound (V) to be used as a starting material of Scheme 3 can be produced, for example, by the method shown in Scheme 5:

earth metal, and specific examples of the boronic acid ester group include boronic acid ester groups such as a boronic acid dimethyl ester group, a boronic acid diethyl ester group, a boronic acid dibutyl ester group, a boronic acid dicyclohexyl group, a boronic acid ethylene glycol ester group, a boronic acid propylene glycol ester group (a boronic acid 1,2-propanediol ester group, a boronic acid 1,3-propanediol ester group), a boronic acid neopentyl glycol ester group, a boronic acid catechol ester group, a boronic acid glycerin ester group, a boronic acid trimethylolethane ester group, a boronic acid diethanolamine ester group, and a boronic acid triethanolamine ester group; and boronic acid anhydride groups.

[Scheme 5]

[Chemical Formula 7]

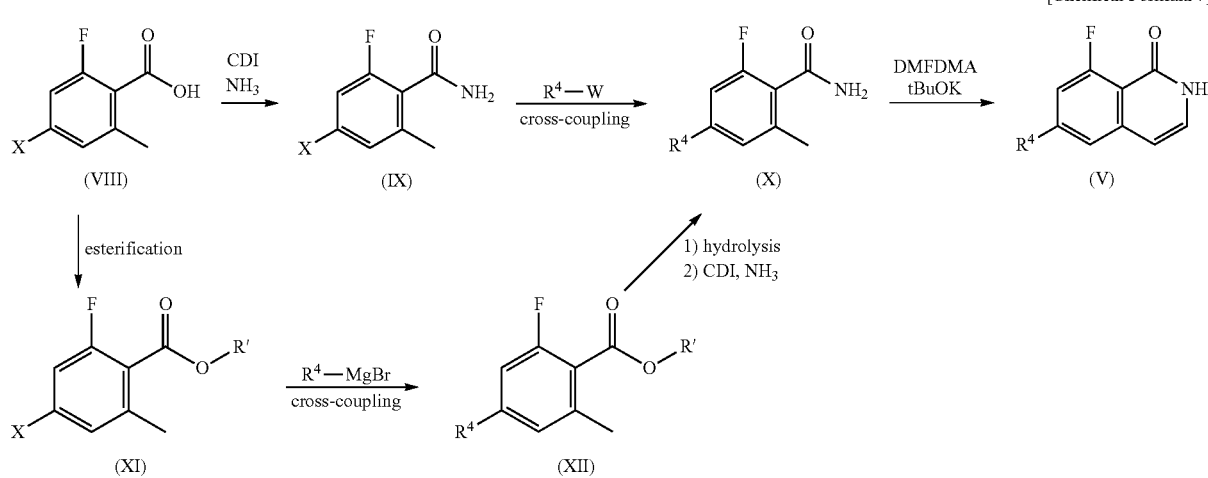

wherein $R^4$, X and W are as defined above, and R' represents a lower alkyl group.

The compound (V) can be produced by a cyclization reaction of the compound (X), which is obtained by a cross-coupling reaction such as Suzuki coupling reaction for introducing $R^4$ group after converting the carboxylic acid group to carbamoyl group, with N,N-dimethylformamide dimethyl acetal.

The compound (V) can also be obtained by a cross-coupling reaction such as Kumada coupling reaction when $R^4$ group is tertiary alkyl group moiety (see a literature of Amruta Joshi-Pangu et al., J. Am. Chem. Soc., 133, 8478-8481 (2011), for example.). That is, the tertiary alkyl compound (XII) can be obtained by stirring the compound (XI), which is obtained by an esterification of the carboxylic acid moiety of the compound (VIII), and tertiary alkyl Grignard reagent ($R^4$MgBr) in the presence of nickel(II) metal catalyst, such as nickel (II) chloride, and N-heterocyclic carbene catalyst, such as 1,3-dicyclohexyl-1H-imidazol-3-ium, at a temperature ranging from ice cold to ambient temperature. The compound (X) can be obtained by hydrolysis of the compound (XII) followed by a converting the carboxylic acid group to the carbamoyl group.

The compound (VIII) to be used as a starting material of Scheme 5 can be obtained as a commercially available product, or prepared by a well-known procedure or the procedure according to it.

In the scheme shown above, a boronyl group represented by W may be in the form of a salt of alkali metal or alkaline It is possible to obtain the compound (I) having the desired functional group at the desired position of the present invention by appropriately using the above methods in combination, and then carrying out a method usually used in organic synthetic chemistry (for example, an alkylation reaction of an amino group, an oxidizing reaction of alkylthio group into a sulfoxide group or a sulfone group, a reaction of converting an alkoxy group into a hydroxyl group, or a reaction of inversely converting the group).

It is possible to obtain the prodrug of the compound (I) of the present invention by esterification reaction of the compound (I) or its intermediate using a method usually used in organic synthetic chemistry including protection or deprotection of a functional group, if necessary.

[Applications of Compound (I) of the Present Invention]

The compound (I) or a pharmaceutically acceptable salt thereof of the present invention can be formulated into a conventional pharmaceutical formulation (pharmaceutical composition), which is suited for oral administration, parenteral administration, or local administration.

Formulations for oral administration include solid formulations such as tablets, granules, powders, and capsules; and liquid formulations such as syrups. These formulations can be prepared by a conventional method. The solid formulations can be prepared by using conventional pharmaceutical carriers, for example, lactose; starches such as corn starch; crystalline celluloses such as microcrystalline cellulose; and hydroxypropyl cellulose, calcium carboxymethyl cellulose, talc, and magnesium stearate. Capsules can be prepared by encapsulating thus prepared granules or powders. Syrups can be prepared by dissolving or suspending the compound (I) or a pharmaceutically acceptable salt thereof of the present invention in an aqueous solution containing sucrose and carboxymethyl cellulose.

Formulations for parenteral administration include injections such as instillation. Injection formulations can also be prepared by a conventional method, and can be appropriately incorporated into isotonic agents (for example, mannitol, sodium chloride, glucose, sorbitol, glycerol, xylitol, fructose, maltose, mannose), stabilizers (for example, sodium sulfite, albumin), and antiseptics (for example, benzyl alcohol, methyl p-oxybenzoate).

The dosage of the compound (I) or a pharmaceutically acceptable salt thereof of the present invention can vary depending on severity of disease, age and body weight of the patient, and dosage form, and is usually within a range from 1 mg to 1,000 mg per day for adults. The compound or a pharmaceutically acceptable salt thereof can be administered once a day, or dividedly administered twice or three times a day according to an oral or parenteral route.

The compound (I) or a pharmaceutically acceptable salt thereof of the present invention can also be used, as a BTK inhibitor, for reagents to be used in experimental tests and/or researches.

EXAMPLES

The present invention will be more specifically described below by way of Examples and Test Examples, but the present invention is not limited to these Examples.

Identification of the compound was carried out by hydrogen nuclear magnetic resonance spectrum ($^1$H-NMR) and mass spectrum (MS). $^1$H-NMR is measured at 400 MHz, unless otherwise specified, and exchangeable hydrogen cannot be sometimes clearly observed depending on the compound and measurement conditions. br. means a broad signal (broad).

HPLC preparative chromatography was carried out by a commercially available ODS column in a gradient mode using water/methanol (containing formic acid) as eluents, unless otherwise specified.

Referential Example 1

2-(6-Cyclopropyl-8-fluoro-1-oxoisoquinolin-2(1H)-yl)-6-(4,4,5,5-tetramethyl-1,3,2-dioxaborolan-2-yl) benzyl acetate

[Chemical Formula 8]

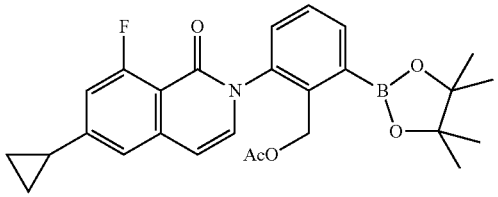

(First Step)

Under nitrogen atmosphere, 4-bromo-2-fluoro-6-methylbenzoic acid (13.0 g, 55.8 mmol) was dissolved in THF (100 mL). To this solution, 1,1'-carbonyldiimidazole (11.8 g, 72.5 mmol) was added at 0° C., and then stirred at 0° C. for 2 h. To this reaction mixture, 28% ammonia solution (10 mL) was added dropwise during a period of 5 min, and then stirred at ambient temperature for further 2 days. The reaction mixture was concentrated to around 50 mL under reduced pressure, and 6M hydrochloric acid aq. solution (30 mL) was added, and then extracted with ethyl acetate (2×100 mL). The combined organic layer was washed with a saturated sodium hydrogen carbonate solution and brine, dried over sodium sulfate, filtered and concentrated to afford 4-bromo-2-fluoro-6-methylbenzamide (11.0 g).

$^1$H NMR (400 MHz, CDCl$_3$) δ7.22 (dt, J=1.8, 0.8 Hz, 1H), 7.15 (dd, J=9.0, 1.9 Hz, 1H), 6.06-5.60 (m, 2H), 2.44 (s, 3H); LCMS (m/z): 231.9 [M+H]$^+$.

(Second Step)

Under nitrogen atmosphere, cyclopropylboronic acid (6.11 g, 71.1 mmol), tricyclohexylphosphine (0.80 g, 2.84 mmol), tris(dibenzylideneacetone)dipalladium (0) (0.43 g, 0.47 mmol) and potassium carbonate (19.65 g, 142.0 mmol) were added to a mixed solution of 4-bromo-2-fluoro-6-methylbenzamide (11.0 g) in toluene (110 mL) and water (11 mL), and stirred at 115° C. for 14 h. After being cooled to ambient temperature, the precipitate was collected by filtration, washed with ether and water, then dried to afford 4-cyclopropyl-2-fluoro-6-methylbenzamide (3.3 g). The filtrate was extracted with ethyl acetate (2×200 mL), and the combined organic layer was washed with brine, dried over sodium sulfate, filtered and concentrated. The crude material was purified by chromatography on silica gel, eluted with hexane/ethyl acetate to afford 4-cyclopropyl-2-fluoro-6-methylbenzamide (5.3 g).

$^1$H NMR (400 MHz, CDCl$_3$) 6.80-6.70 (m, 1H), 6.60 (dd, J=11.3, 1.6 Hz, 1H), 5.99-5.59 (m, 2H), 2.43 (s, 3H), 1.89-1.80 (m, 1H), 1.03-0.98 (m, 2H), 0.73-0.65 (m, 2H); LCMS (m/z): 194.0 [M+H]$^+$.

(Third Step)

Under nitrogen atmosphere, N,N-dimethylformamide dimethyl acetal (7.0 g, 58.8 mmol) was added to a solution of 4-cyclopropyl-2-fluoro-6-methylbenzamide (8.6 g, 44.5 mmol) in 2-methyltetrahydrofuran (100 mL), and stirred at 60° C. for 2 h. The reaction mixture was concentrated under reduced pressure, and 2-methyltetrahydrofuran (10 mL) was added to this crude material. To this solution, 1 mol/L potassium tert-butoxide in THF solution (68.1 mL, 68.1 mmol) was added dropwise, and stirred at 65° C. for 1 day. After being cooled to ambient temperature, the reaction mixture was poured into 1M hydrochloric acid solution (200 mL). To this solution, isopropyl alcohol (300 mL) was added, and then the solvents were removed under reduced pressure. The precipitate was collected by filtration to afford 6-cyclopropyl-8-fluoroisoquinolin-1(2H)-one (7.7 g).

$^1$H NMR (400 MHz, DMSO-d$_6$) δ11.06 (s, 1H), 7.16 (d, J=1.6 Hz, 1H), 7.11 (dd, J=7.1, 5.7 Hz, 1H), 6.88 (dd, J=13.3, 1.7 Hz, 1H), 6.41 (dd, J=7.1, 2.3 Hz, 1H), 2.07-1.95 (m, 1H), 1.08-1.01 (m, 2H), 0.86-0.79 (m, 2H); LCMS (m/z): 204.1 [M+H]$^+$.

(Fourth Step)

Under nitrogen atmosphere, 2-bromo-6-chlorobenzaldehyde (3.65 g, 16.63 mmol), potassium carbonate (3.54 g, 25.6 mmol) and copper(I) iodide (0.49 g, 2.56 mmol) were added to a solution of 6-cyclopropyl-8-fluoroisoquinolin-1 (2H)-one (2.6 g, 12.8 mmol) in DMF (25 mL), and stirred at 110° C. for 1 day. The reaction mixture was diluted with ethyl acetate (200 mL), filtered to remove insoluble material, and then the filtrate was washed with water and brine, dried over sodium sulfate, filtered and concentrated. The crude material was purified by chromatography on silica gel, eluted with hexane/ethyl acetate to afford 2-chloro-6-(6-cyclopropyl-8-fluoro-1-oxoisoquinolin-2(1H)-yl)benzaldehyde (2.7 g).

$^1$H NMR (400 MHz, DMSO-d$_6$) δ10.18 (s, 1H), 7.84-7.78 (m, 1H), 7.75 (dd, J=8.2, 1.3 Hz, 1H), 7.49 (dd, J=7.8, 1.2 Hz, 1H), 7.41 (d, J=7.5 Hz, 1H), 7.27 (d, J=1.6 Hz, 1H), 7.00 (dd, J=13.3, 1.6 Hz, 1H), 6.64 (dd, J=7.5, 2.2 Hz, 1H), 2.14-2.01 (m, 1H), 1.14-1.06 (m, 2H), 0.92-0.83 (m, 2H); LCMS (m/z): 342.1 [M+H]$^+$.

(Fifth Step)

Under nitrogen atmosphere, a mixed solution of 2-chloro-6-(6-cyclopropyl-8-fluoro-1-oxoisoquinolin-2(1H)-yl) benzaldehyde (2.5 g, 7.32 mmol) in DCM (26 mL) and isopropyl alcohol (13 mL) was cooled to 0° C. To this solution, sodium borohydride (0.42 g, 11.0 mmol) was added at 0° C., and then stirred at 0° C. for 2 h. Water (50 mL) was added to the reaction mixture, and extracted with ethyl acetate (2×50 mL). The combined organic layer was washed with water and brine, dried over sodium sulfate, filtered and concentrated to afford 2-[3-chloro-2-(hydroxymethyl)phenyl]-6-cyclopropyl-8-fluoroisoquinolin-1(2H)-one (2.3 g).

$^1$H NMR (400 MHz, CDCl$_3$) δ7.55 (dd, J=8.1, 1.2 Hz, 1H), 7.40 (t, J=8.0 Hz, 1H), 7.15 (dd, J=8.0, 1.2 Hz, 1H), 7.08-7.00 (m, 2H), 6.82 (dd, J=12.7, 1.7 Hz, 1H), 6.51 (dd, J=7.4, 2.1 Hz, 1H), 4.71-4.61 (m, 1H), 4.46 (d, J=11.9 Hz, 1H), 3.43-3.29 (m, 1H), 2.03-1.97 (m, 1H), 1.18-1.10 (m, 2H), 0.88-0.81 (m, 2H); LCMS (m/z): 343.9 [M+H]$^+$.

(Sixth Step)

Under nitrogen atmosphere, pyridine (2.36 mL, 29.3 mmol) and acetyl chloride (1.56 mL, 21.95 mmol) were added to a solution of 2-[3-chloro-2-(hydroxymethyl)phenyl]-6-cyclopropyl-8-fluoroisoquinolin-1(2H)-one (2.26 g, 6.59 mmol) in DCM (30 mL), and stirred at ambient temperature for 1 day. Water (50 mL) was added to the reaction mixture, and extracted with ethyl acetate (2×50 mL). The combined organic layer was washed with water and brine, dried over sodium sulfate, filtered and concentrated. The crude material was purified by chromatography on silica gel, eluted with hexane/ethyl acetate to afford 2-chloro-6-(6-cyclopropyl-8-fluoro-1-oxoisoquinolin-2(1H)-yl) benzyl acetate (2.3 g).

$^1$H NMR (400 MHz, CDCl$_3$) δ7.53 (dd, J=8.2, 1.2 Hz, 1H), 7.46-7.39 (m, 1H), 7.22 (dd, J=7.9, 1.3 Hz, 1H), 7.04-6.98 (m, 2H), 6.80 (dd, J=12.6, 1.7 Hz, 1H), 6.43 (dd, J=7.4, 2.1 Hz, 1H), 5.25 (d, J=12.5 Hz, 1H), 4.98 (d, J=12.4 Hz, 1H), 2.02-1.96 (m, 1H), 1.96 (s, 3H), 1.16-1.10 (m, 2H), 0.86-0.81 (m, 2H); LCMS (m/z): 386.0 [M+H]$^+$.

(Seventh Step)

Under nitrogen atmosphere, bis(pinacolato)diboron (9.48 g, 37.3 mmol), bis(dibenzylideneacetone)palladium (0) (0.36 g, 0.62 mmol), 2,4,6-triisopropyl-2'-(dicyclohexylphosphino)biphenyl (0.59 g, 1.24 mmol) and potassium acetate (3.66 g, 37.3 mmol) were added to a solution of 2-chloro-6-(6-cyclopropyl-8-fluoro-1-oxoisoquinolin-2(1H)-yl) benzyl acetate (4.8 g, 12.44 mmol) in 1,4-dioxane (180 mL), and stirred at 65° C. for 16 h. The reaction mixture was diluted with ethyl acetate (200 mL), filtered through Celite pad to remove insoluble material. Water (200 mL) was added to the filtrate, and extracted with ethyl acetate (2×200 mL). The combined organic layer was washed with brine, dried over sodium sulfate, filtered and concentrated. The crude material was purified by chromatography on silica gel, eluted with hexane/ethyl acetate. To the oily material, hexane was added, and then the precipitate was collected by filtration to afford the titled compound (3.05 g).

$^1$H NMR (400 MHz, CDCl$_3$) δ7.93 (dd, J=7.4, 1.4 Hz, 1H), 7.47 (t, J=7.6 Hz, 1H), 7.35 (dd, J=7.8, 1.5 Hz, 1H), 7.02 (d, J=7.4 Hz, 1H), 7.00 (d, J=1.6 Hz, 1H), 6.78 (dd, J=12.7, 1.7 Hz, 1H), 6.40 (dd, J=7.4, 2.1 Hz, 1H), 5.45 (d, J=11.8 Hz, 1H), 5.03 (d, J=11.9 Hz, 1H), 2.03-1.93 (m, 1H), 1.92 (s, 3H), 1.34 (s, 12H), 1.15-1.08 (m, 2H), 0.87-0.80 (m, 2H); LCMS (m/z): 478.2 [M+H]$^+$.

Referential Example 2

2-[6-(tert-Butyl)-8-fluoro-1-oxoisoquinolin-2(1H)-yl]-6-(4,4,5,5-tetramethyl-1,3,2-dioxaborolan-2-yl) benzyl acetate

[Chemical Formula 9]

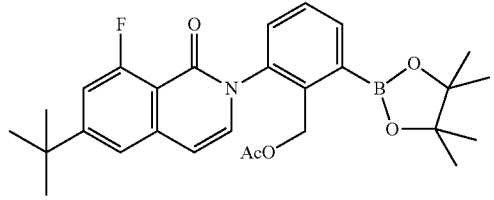

(First Step)

Under nitrogen atmosphere, methyl 4-bromo-2-fluoro-6-methylbenzoate (1.0 g, 4.05 mmol), nickel(II) chloride (0.13 g, 0.81 mmol) and 1,3-dicyclohexyl-1H-imidazol-3-ium (0.26 g, 0.81 mmol) were dissolved in THF (10 mL). This solution was cooled to 0° C., and 1M tert-butylmagnesium bromide (THF solution, 12.1 mL, 12.1 mmol) was added dropwise during a period of 10 min, and then stirred at ambient temperature for 24 h. The reaction mixture was poured into cold water (200 mL), acidified to pH 2 with concentrated hydrochloric acid (ca. 5 mL), and then extracted with ethyl acetate. The organic layer was dried over sodium sulfate, filtered and concentrated. The crude material was purified by chromatography on silica gel, eluted with hexane/ethyl acetate to afford methyl 4-(tert-butyl)-2-fluoro-6-methylbenzoate (0.45 g).

The obtained methyl 4-(tert-butyl)-2-fluoro-6-methylbenzoate (0.35 g) was dissolved in a mixed solution of THF and water (1:1, 10 mL), and 4M lithium hydroxide solution in water (2 mL) was added and then stirred at 60° C. for 6 h. The reaction mixture was diluted with cold water, and the organic solvent was removed under reduced pressure. This aqueous solution was acidified to pH 2 with concentrated hydrochloric acid solution and extracted with ethyl acetate. The organic layer was dried over sodium sulfate, filtered and concentrated to afford crude material of 4-(tert-butyl)-2-fluoro-6-methylbenzoic acid (0.35 g).

LCMS (m/z): 211.0 [M+H]$^+$.

(Second Step)

Under nitrogen atmosphere, 4-(tert-butyl)-2-fluoro-6-methylbenzoic acid (0.21 g, 0.10 mmol) was dissolved in THF (10 mL). To this solution, 1,1'-carbonyldiimidazole (0.21 g, 1.30 mmol) was added at 0° C. and then stirred at 0° C. for 2 h. To this reaction mixture, 28% ammonia solution (10 mL) was added dropwise and then stirred at ambient temperature for further 2 days. The reaction mixture was concentrated under reduced pressure, and 6M hydrochloric acid solution was added, and then extracted with ethyl acetate for 2 times. The combined organic layer was washed with saturated sodium hydrogen carbonate solution and brine, dried over sodium sulfate, filtered and concentrated to afford 4-(tert-butyl)-2-fluoro-6-methylbenzamide (0.20 g).

$^1$H NMR (400 MHz, DMSO-ds) δ 7.85 (s, 1H), 7.58 (s, 1H), 7.10-7.07 (m, 1H), 7.05-7.00 (m, 1H), 2.29 (s, 3H), 1.26 (s, 9H); LCMS (m/z): 210.1 [M+H]$^+$.

(Third Step)

Under nitrogen atmosphere, N,N-dimethylformamide dimethyl acetal (113 mg, 0.95 mmol) was added to a solution of 4-(tert-butyl)-2-fluoro-6-methylbenzamide (150 mg, 0.72 mmol) in 2-methyltetrahydrofuran (10 mL) and stirred at 60° C. for 2 h. The reaction mixture was concentrated under reduced pressure, and 2-methyltetrahydrofuran (10 mL) was added to this crude material. To this solution, 1M potassium tert-butoxide (THF solution, 1.1 mL, 1.1 mmol) was added dropwise, and stirred at 65° C. for 1 day. After being cooled to ambient temperature, the reaction mixture was poured into 1M hydrochloric acid solution (10 mL), and extracted with ethyl acetate for 2 times. The combined organic layer was washed with water and brine, dried over sodium sulfate, filtered and concentrated. The crude material was purified by chromatography on silica gel, eluted with hexane/ethyl acetate to afford 6-(tert-butyl)-8-fluoroisoquinolin-1(2H)-one (85 mg).

$^1$H NMR (400 MHz, CDCl$_3$) δ 10.84 (s, 1H), 7.28 (d, J=1.8 Hz, 1H), 7.18 (dd, J=13.8, 1.8 Hz, 1H), 6.51-6.43 (m, 2H), 1.37 (s, 9H); LCMS (m/z): 220.1 [M+H]$^+$.

(Fourth Step)

Under nitrogen atmosphere, 2-bromo-6-chlorobenzaldehyde (330 mg, 2.01 mmol), potassium carbonate (277 mg, 2.01 mmol) and copper(I) iodide (382 mg, 2.01 mmol) were added to a solution of 6-(tert-butyl)-8-fluoroisoquinolin-1 (2H)-one (220 mg, 1.00 mmol) which similarly prepared according to the procedure described in the Third Step in DMF (10 mL), and stirred at 110° C. for 1 day. The reaction mixture was diluted with ethyl acetate, filtered to remove insoluble material, and then the filtrate was washed with water and brine, dried over sodium sulfate, filtered and concentrated. The crude material was purified by chromatography on silica gel, eluted with hexane/ethyl acetate to afford 2-chloro-6-[6-(tert-butyl)-8-fluoro-1-oxoisoquinolin-2(1H)-yl]benzaldehyde (223 mg).

$^1$H NMR (400 MHz, DMSO-d$_6$) δ 10.20 (s, 1H), 7.87-7.79 (m, 1H), 7.76 (dd, J=8.2, 1.3 Hz, 1H), 7.54 (d, J=1.8 Hz, 1H), 7.49 (dd, J=7.6, 1.2 Hz, 1H), 7.43 (d, J=7.3 Hz, 1H), 7.38-7.26 (m, 1H), 6.74 (dd, J=7.5, 2.2 Hz, 1H), 1.35 (s, 9H); LCMS (m/z): 358.1 [M+H]$^+$.

(Fifth Step)

Under nitrogen atmosphere, a mixed solution of 2-chloro-6-[6-(tert-butyl)-8-fluoro-1-oxoisoquinolin-2(1H)-yl]benzaldehyde (200 mg, 0.56 mmol) in DCM (3.7 mL) and isopropyl alcohol (1.9 mL) was cooled to 0° C. To this solution, sodium borohydride (32 mg, 0.84 mmol) was added at 0° C. then stirred at ambient temperature for 2 h. Water was added to the reaction mixture, and extracted with ethyl acetate for 2 times. The combined organic layer was washed with water and brine, dried over sodium sulfate, filtered and concentrated. The crude material was purified by chromatography on silica gel, eluted with hexane/ethyl acetate to afford 2-[3-chloro-2-(hydroxymethyl)phenyl]-6-(tert-butyl)-8-fluoroisoquinolin-1(2H)-one (160 mg).

$^1$H NMR (400 MHz, CDCl$_3$) δ 7.55 (dd, J=8.1, 1.2 Hz, 1H), 7.43-7.36 (m, 1H), 7.32 (d, J=1.8 Hz, 1H), 7.23 (dd, J=13.5, 1.8 Hz, 1H), 7.17-7.11 (m, 1H), 7.05 (d, J=7.4, 1.7 Hz, 1H), 6.58 (dd, J=7.4, 2.1 Hz, 1H), 4.75-4.61 (m, 1H), 4.54-4.34 (m, 1H), 3.35 (dd, J=10.8, 2.5 Hz, 1H), 1.39 (s, 9H); LCMS (m/z): 360.2 [M+H]$^+$.

(Sixth Step)

Under nitrogen atmosphere, pyridine (180 μL, 2.24 mmol) and acetyl chloride (119 μL, 1.68 mmol) were added to a solution of 2-[3-chloro-2-(hydroxymethyl)phenyl]-6-(tert-butyl)-8-fluoroisoquinolin-1(2H)-one (160 mg, 0.89 mmol) in DCM (5 mL) and stirred at ambient temperature for 1 day. Water was added to the reaction mixture, and extracted with ethyl acetate for 2 times. The combined organic layer was washed with water and brine, dried over sodium sulfate, filtered and concentrated. The crude material was purified by chromatography on silica gel, eluted with hexane/ethyl acetate to afford 2-chloro-6-[6-(tert-butyl)-8-fluoro-1-oxoisoquinolin-2(1H)-yl]benzyl acetate (157 mg).

$^1$H NMR (400 MHz, CDCl$_3$) δ 7.72-7.64 (m, 1H), 7.63-7.57 (m, 1H), 7.54 (d, J=1.8 Hz, 1H), 7.44-7.38 (m, 1H), 7.38-7.30 (m, 2H), 6.71 (dd, J=7.4, 2.1 Hz, 1H), 5.08 (d, J=12.4, 2.4 Hz, 1H), 4.93 (d, J=12.4, 2.5 Hz, 1H), 1.87 (s, 3H), 1.35 (s, 9H); LCMS (m/z): 402.2 [M+H]$^+$.

(Seventh Step)

Under nitrogen atmosphere, bis(pinacolato)diboron (284 mg, 1.12 mmol), bis(dibenzylideneacetone)palladium (0) (10.7 mg, 19.0 mol), 2,4,6-triisopropyl-2'-(dicyclohexylphosphino)biphenyl (17.8 g, 37.0 mol) and potassium acetate (110 mg, 1.12 mmol) were added to a solution of 2-chloro-6-[6-(tert-butyl)-8-fluoro-1-oxoisoquinolin-2(1H)-yl]benzyl acetate (150 mg, 0.37 mmol) in 1,4-dioxane (5.3 mL), and stirred at 65° C. for 16 h. The reaction mixture was diluted with ethyl acetate, filtered through Celite pad to remove insoluble material. Water was added to the filtrate, and extracted with ethyl acetate for 2 times. The combined organic layer was dried over sodium sulfate, filtered and concentrated. The crude material was purified by chromatography on silica gel, eluted with hexane/ethyl acetate to afford the titled compound (105 mg).

$^1$H NMR (400 MHz, CDCl$_3$) δ 7.97-7.87 (m, 1H), 7.48 (t, J=7.6 Hz, 1H), 7.34 (dd, J=7.9, 1.4 Hz, 1H), 7.27 (d, J=1.9 Hz, 1H), 7.18 (dd, J=13.5, 1.8 Hz, 1H), 7.04 (d, J=7.4 Hz, 1H), 6.46 (dd, J=7.4, 2.1 Hz, 1H), 5.46 (d, J=11.8 Hz, 1H), 5.02 (d, J=11.8 Hz, 1H), 1.92 (s, 3H), 1.38 (s, 9H), 1.34 (s, 12H); LCMS (m/z): 494.3 [M+H]$^+$.

Example 1

2-(3-{4-Amino-6-[(1-methyl-1H-pyrazol-4-yl) amino]-1,3,5-triazin-2-yl}-2-(hydroxymethyl)phenyl)-6-cyclopropyl-8-fluoroisoquinolin-1(2H)-one

[Chemical Formula 10]

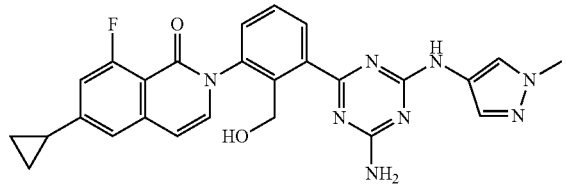

(First Step)

To a solution of 2-amino-4,6-dichloro-1,3,5-triazine (513 mg, 3.11 mmol) in THF (10.3 mL), cooled with ice bath, DIEA (1.08 mL, 6.22 mmol) and 1-methyl-1H-pyrazol-4-amine (332 mg, 3.42 mmol) in THF solution (5.18 mL) were added slowly then stirred at ambient temperature for 2.5 h. The precipitate was collected by filtration, washed with ethyl acetate, water and ethanol, and then dried to afford 6-chloro-$N^2$-(1-methyl-1H-pyrazol-4-yl)-1,3,5-triazine-2,4-diamine (420 mg).

$^1$H NMR (400 MHz, DMSO-$d_6$) δ 9.89 (s, 1H), 7.91 (s, 1H), 7.56-7.49 (m, 3H), 3.79 (s, 3H); LCMS (m/z): 225.9 [M+H]$^+$.

(Second Step)

To a stirred solution of 2-(6-cyclopropyl-8-fluoro-1-oxoisoquinolin-2(1H)-yl)-6-(4,4,5,5-tetramethyl-1,3,2-dioxaborolan-2-yl)benzyl acetate (141 mg, 0.29 mmol) which was afforded in the Referential Example 1 and 6-chloro-$N^2$-(1-methyl-1H-pyrazol-4-yl)-1,3,5-triazine-2,4-diamine (66.7 mg, 0.29 mmol) in dimethoxyethane (5 mL), tetrakis(triphenylphosphine) palladium (0) (17 mg, 0.015 mmol) and potassium carbonate (82 mg, 0.59 mmol) in water solution (1.67 mL) were added, and then heated with the microwave synthesizer at 110° C. for 20 min. Water was added to the reaction mixture, and extracted with ethyl acetate, then the organic layer was washed with saturated sodium hydrogen bicarbonate solution and brine, dried over sodium sulfate, filtered and concentrated. The crude material was purified by chromatography on silica gel, eluted with hexane/ethyl acetate to afford a mixture of 2-(3-{4-amino-6-[(1-methyl-1H-pyrazol-4-yl)amino]-1,3,5-triazin-2-yl}-2-(hydroxymethyl)phenyl)-6-cyclopropyl-8-fluoroisoquinolin-1(2H)-one and its acetylated product. The mixed material was dissolved in methanol (5 mL), potassium carbonate (100 mg, 0.724 mmol) was added and stirred at ambient temperature for 2 h. The reaction mixture was diluted with water, and the precipitate was collected by filtration, washed with water and diethyl ether, and then dried to afford the titled compound (85 mg).

$^1$H NMR (400 MHz, DMSO-$d_6$) δ 9.71 (s, 1H), 8.00 (s, 1H), 7.94-7.82 (m, 1H), 7.61-7.42 (m, 3H), 7.37-7.26 (m, 4H), 7.00 (dd, J=13.3, 1.7 Hz, 1H), 6.62 (dd, J=7.5, 2.1 Hz, 1H), 5.25-5.13 (m, 1H), 4.55-4.44 (m, 1H), 4.16-4.02 (m, 1H), 3.84-3.75 (m, 3H), 2.12-2.04 (m, 1H), 1.14-1.06 (m, 2H), 0.91-0.84 (m, 2H); LCMS (m/z): 499.2 [M+H]$^+$.

Example 2

4-({4-Amino-6-[3-(6-cyclopropyl-8-fluoro-1-oxoisoquinolin-2(1H)-yl)-2-(hydroxymethyl)phenyl]-1,3,5-triazin-2-yl}amino)-1-methyl-1H-pyrrole-2-carbonitrile

[Chemical Formula 11]

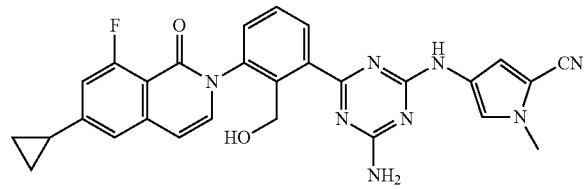

(First Step)

To a suspension of 4-amino-1-methyl-1H-pyrrole-2-carboxamide hydrochloride (350 mg, 1.99 mmol) and DIEA (0.7 mL, 3.99 mmol) in THF (5 mL), cooled with ice bath, DMF (2.5 mL) and 2-amino-4,6-dichloro-1,3,5-triazine (299 mg, 1.81 mmol) were added and stirred at ambient temperature for 5 h. The precipitate was collected by filtration, washed with ethyl acetate and water, and then dried to afford 4-[(4-amino-6-chloro-1,3,5-triazin-2-yl)amino]-1-methyl-1H-pyrrole-2-carboxamide (436 mg).

$^1$H NMR (400 MHz, DMSO-$d_6$) δ 10.00-9.43 (m, 1H), 7.46 (s, 1H), 7.40 (s, 1H), 7.29 (d, J=1.9 Hz, 1H), 7.21-6.79 (m, 2H), 6.77-6.65 (m, 1H), 3.80 (s, 3H); LCMS (m/z): 268.1 [M+H]$^+$.

(Second Step)

To a solution of 4-[(4-amino-6-chloro-1,3,5-triazin-2-yl)amino]-1-methyl-1H-pyrrole-2-carboxamide (130 mg, 0.49 mmol) in DCM (5 mL), cooled with ice bath, TEA (0.1 mL, 0.73 mmol) and trifluoroacetic anhydride (0.075 mL, 0.53 mmol) were added and stirred at ambient temperature for 2 h. To the reaction mixture, supplementary amount of TEA (0.1 mL, 0.73 mmol) and trifluoroacetic anhydride (0.075 mL, 0.53 mmol) were added and stirred at ambient temperature for further 24 h. Water was added to the reaction mixture, and extracted with ethyl acetate, then the organic layer was washed with water and brine, dried over sodium sulfate, filtered and concentrated. The crude material was purified by chromatography on silica gel, eluted with hexane/ethyl acetate to afford 4-[(4-amino-6-chloro-1,3,5-triazin-2-yl)amino]-1-methyl-1H-pyrrole-2-carbonitrile (100 mg).

$^1$H NMR (400 MHz, DMSO-$d_6$) δ 10.05-9.71 (m, 1H), 7.55 (s, 2H), 7.46-7.23 (m, 1H), 7.03-6.76 (m, 1H), 3.72 (s, 3H); LCMS (m/z): 250.1 [M+H]$^+$.

(Third Step)

To a stirred solution of 2-(6-cyclopropyl-8-fluoro-1-oxoisoquinolin-2(1H)-yl)-6-(4,4,5,5-tetramethyl-1,3,2-dioxaborolan-2-yl)benzyl acetate (45 mg, 0.094 mmol) which was afforded in the Referential Example 1 and 4-[(4-amino-6-chloro-1,3,5-triazin-2-yl)amino]-1-methyl-1H-pyrrole-2-carbonitrile (23.5 mg, 0.094 mmol) in dimethoxyethane (2 mL), tetrakis(triphenylphosphine)palladium (0) (5.4 mg, 0.0047 mmol) and potassium carbonate (26 mg, 0.19 mmol) in water solution (0.67 mL) were added and heated with the microwave synthesizer at 110° C. for 20 min. Water was added to the reaction mixture, and extracted with ethyl acetate, then the organic layer was washed with water and brine, dried over sodium sulfate, filtered and concentrated. The crude material was purified by chromatography on silica gel, eluted with hexane/ethyl acetate to afford a mixture of 4-({4-amino-6-[3-(6-cyclopropyl-8-fluoro-1-oxoisoquinolin-2(1H)-yl)-2-(hydroxymethyl)phenyl]-1,3,5-triazin-2-yl}amino)-1-m ethyl-1H-pyrrole-2-carbonitrile and its acetylated product. The mixed material was dissolved in methanol (5 mL), potassium carbonate (100 mg, 0.724 mmol) was added and stirred at 60° C. for 1 h. Water was added to the reaction mixture, and the precipitate was collected by filtration, washed with water and hexane, and then dried to afford the titled compound (18 mg).

$^1$H NMR (400 MHz, DMSO-$d_6$) δ 10.15-9.19 (m, 1H), 7.87 (d, J=7.6 Hz, 1H), 7.65-7.50 (m, 2H), 7.49-7.41 (m, 1H), 7.40-7.30 (m, 3H), 7.28 (d, J=1.7 Hz, 1H), 7.04 (d, J=1.7 Hz, 1H), 7.00 (dd, J=13.3, 1.6 Hz, 1H), 6.62 (dd, J=7.5, 2.1 Hz, 1H), 5.23-4.91 (m, 1H), 4.50 (d, J=9.5 Hz, 1H), 4.19-3.94 (m, 1H), 3.74 (s, 3H), 2.16-2.00 (m, 1H), 1.15-1.03 (m, 2H), 0.95-0.77 (m, 2H); LCMS (m/z): 523.2 [M+H]$^+$.

Example 3-33

Each of the Example compounds shown in the following [Table 1-1] to [Table 1-3] were prepared according to the procedure described in the above Examples or modified procedure well known in the art of organic chemistry if needed, using appropriate starting materials (those materials are obtained from commercial sources, or are prepared by literature procedures or modifications of literature procedures known to persons skilled in the art).

The physicochemical data of each compound were shown in the following [Table 2-1] to [Table 2-2].

TABLE 1-1

| Ex. No. | Structure | Name |
|---|---|---|
| 3 | 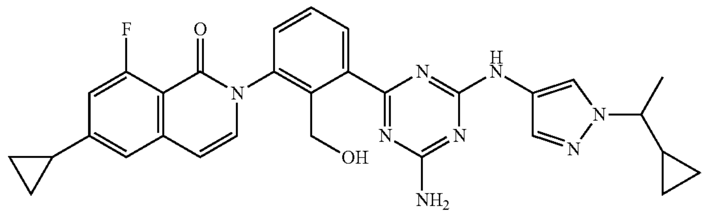 [SMILES: CC(C1CC1)n1cc(Nc2nc(N)nc(-c3cccc(-n4ccc5cc(C6CC6)cc(F)c5c4=O)c3CO)n2)cn1] | 2-[3-(4-Amino-6-{[1-(1-cyclopropyl-ethyl)-1H-pyrazol-4-yl]amino}-1,3,5-triazin-2-yl)-2-(hydroxymethyl)phenyl]-6-cyclopropyl-8-fluoroisoquinolin-1(2H)-one |
| 4 | 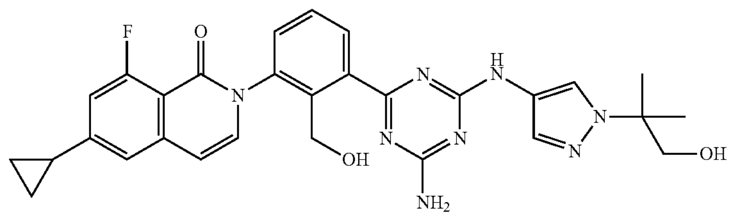 [SMILES: CC(C)(CO)n1cc(Nc2nc(N)nc(-c3cccc(-n4ccc5cc(C6CC6)cc(F)c5c4=O)c3CO)n2)cn1] | 2-[3-(4-Amino-6-{[1-(1-hydroxy-2-methylpropan-2-yl)-1H-pyrazol-4-yl]amino}-1,3,5-triazin-2-yl)-2-(hydroxymethyl)phenyl]-6-cyclopropyl-8-fluoroisoquinolin-1(2H)-one |
| 5 | 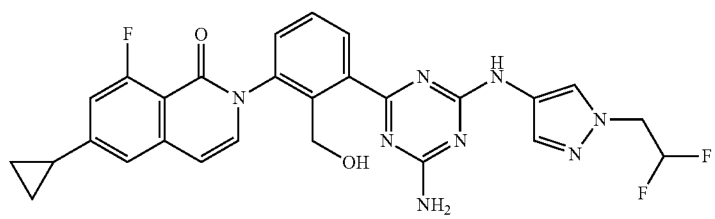 [SMILES: Nc1nc(Nc2cnn(CC(F)F)c2)nc(-c2cccc(-n3ccc4cc(C5CC5)cc(F)c4c3=O)c2CO)n1] | 2-[3-(4-Amino-6-{[1-(2,2-difluoroethyl)-1H-pyrazol-4-yl]amino}-1,3,5-triazin-2-yl)-2-(hydroxymethyl)phenyl]-6-cyclopropyl-8-fluoroisoquinolin-1(2H)-one |
| 6 | 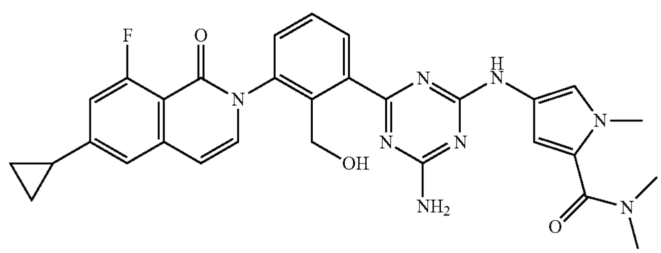 [SMILES: CN(C)C(=O)c1cc(Nc2nc(N)nc(-c3cccc(-n4ccc5cc(C6CC6)cc(F)c5c4=O)c3CO)n2)cn1C] | 4-({4-Amino-6-[3-(6-cyclopropyl-8-fluoro-1-oxoisoquinolin-2(1H)-yl)-2-(hydroxymethyl)phenyl]-1,3,5-triazin-2-yl}amino)-N,N,1-trimethyl-1H-pyrrole-2-carboxamide |
| 7 | 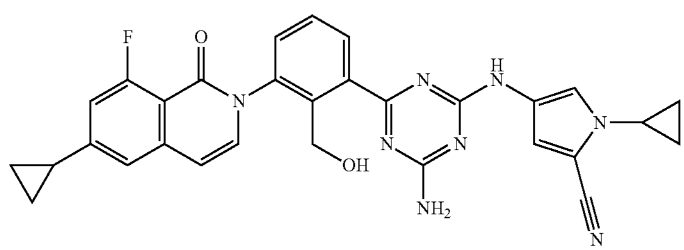 [SMILES: N#Cc1cc(Nc2nc(N)nc(-c3cccc(-n4ccc5cc(C6CC6)cc(F)c5c4=O)c3CO)n2)cn1C1CC1] | 4-({4-Amino-6-[3-(6-cyclopropyl-8-fluoro-1-oxoisoquinolin-2(1H)-yl)-2-(hydroxymethyl)phenyl]-1,3,5-triazin-2-yl}amino)-1-cyclopropyl-1H-pyrrole-2-carbonitrile |
| 8 | 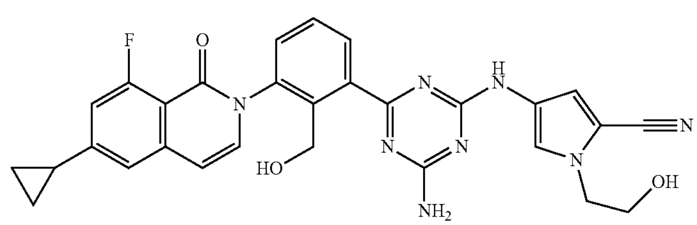 [SMILES: N#Cc1cc(Nc2nc(N)nc(-c3cccc(-n4ccc5cc(C6CC6)cc(F)c5c4=O)c3CO)n2)cn1CCO] | 4-({4-Amino-6-[3-(6-cyclopropyl-8-fluoro-1-oxoisoquinolin-2(1H)-yl)-2-(hydroxymethyl)phenyl]-1,3,5-triazin-2-yl}amino)-1-(2-hydroxyethyl)-1H-pyrrole-2-carbonitrile |

TABLE 1-1-continued

| Ex. No. | Structure | Name |
|---|---|---|
| 9 | 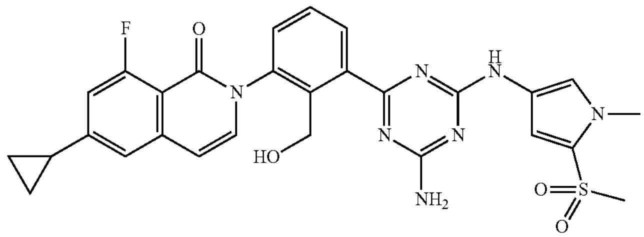 [SMILES: Cn1cc(Nc2nc(N)nc(-c3cccc(-n4ccc5cc(C6CC6)cc(F)c5c4=O)c3CO)n2)cc1S(C)(=O)=O] | 2-[3-(4-Amino-6-{[1-methyl-5-(methylsulfonyl)-1H-pyrrol-3-yl]amino}-1,3,5-triazin-2-yl)-2-(hydroxymethyl)phenyl]-6-cyclopropyl-8-fluoroisoquinolin-1(2H)-one |
| 10 | 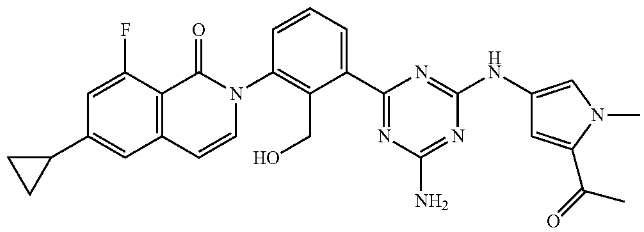 [SMILES: CC(=O)c1cc(Nc2nc(N)nc(-c3cccc(-n4ccc5cc(C6CC6)cc(F)c5c4=O)c3CO)n2)cn1C] | 2-(3-{4-[(5-Acetyl-1-methyl-1H-pyrrol-3-yl)amino]-6-amino-1,3,5-triazin-2-yl}-2-(hydroxymethyl)phenyl)-6-cyclopropyl-8-fluoroisoquinolin-1(2H)-one |
| 11 | 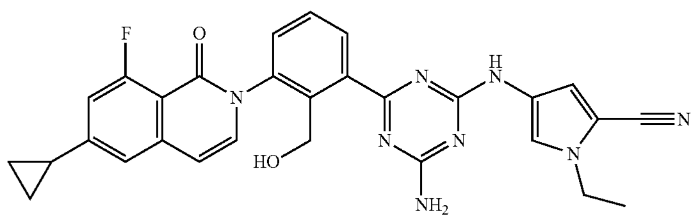 [SMILES: CCn1cc(Nc2nc(N)nc(-c3cccc(-n4ccc5cc(C6CC6)cc(F)c5c4=O)c3CO)n2)cc1C#N] | 4-({4-Amino-6-[3-(6-cyclopropyl-8-fluoro-1-oxoisoquinolin-2(1H)-yl)-2-(hydroxymethyl)phenyl]-1,3,5-triazin-2-yl}amino)-1-ethyl-1H-pyrrole-2-carbonitrile |
| 12 | 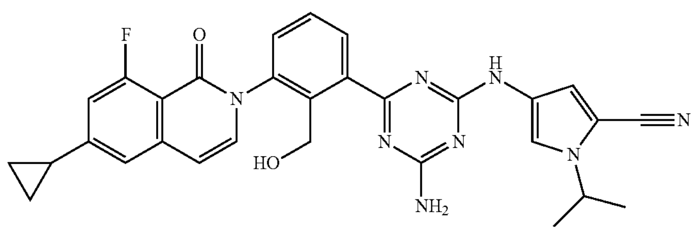 [SMILES: CC(C)n1cc(Nc2nc(N)nc(-c3cccc(-n4ccc5cc(C6CC6)cc(F)c5c4=O)c3CO)n2)cc1C#N] | 4-({4-Amino-6-[3-(6-cyclopropyl-8-fluoro-1-oxoisoquinolin-2(1H)-yl)-2-(hydroxymethyl)phenyl]-1,3,5-triazin-2-yl}amino)-1-isopropyl-1H-pyrrole-2-carbonitrile |

TABLE 1-2

| | | |
|---|---|---|
| 13 |  | 4-({4-Amino-6-[3-(6-cyclopropyl-8-fluoro-1-oxoisoquinolin-2(1H)-yl)-2-(hydroxymethyl)phenyl]-1,3,5-triazin-2-yl}amino)-1-(2-methoxyethyl)-1H-pyrrole-2-carbonitrile |
| 14 |  | 2-(3-{4-[(1H-Pyrazol-4-yl)amino]-6-amino-1,3,5-triazin-2-yl}-2-(hydroxymethyl)phenyl)-6-cyclopropyl-8-fluoroisoquinolin-1(2H)-one |

TABLE 1-2-continued

| | Structure | Name |
|---|---|---|
| 15 | | 2-[4-({4-Amino-6-[3-(6-cyclopropyl-8-fluoro-1-oxoisoquinolin-2(1H)-yl)-2-(hydroxymethyl)phenyl]-1,3,5-triazin-2-yl}amino)-2-cyano-1H-pyrrol-1-yl]acetamide |
| 16 | | 2-[3-(4-Amino-6-{[1-(2-morpholinoethyl)-1H-pyrazol-4-yl]amino}-1,3,5-triazin-2-yl)-2-(hydroxymethyl)phenyl]-6-cyclopropyl-8-fluoroisoquinolin-1(2H)-one |
| 17 | | 2-{3-[4-Amino-6-({1-[2-(dimethylamino)ethyl]-1H-pyrazol-4-yl}amino)-1,3,5-triazin-2-yl]-2-(hydroxymethyl)phenyl}-6-cyclopropyl-8-fluoroisoquinolin-1(2H)-one |
| 18 | | 2-{3-[4-Amino-6-({1-[3-(dimethylamino)propyl]-1H-pyrazol-4-yl}amino)-1,3,5-triazin-2-yl]-2-(hydroxymethyl)phenyl}-6-cyclopropyl-8-fluoroisoquinolin-1(2H)-one |
| 19 | | 2-{3-[4-Amino-6-({1-[2-(pyrrolidin-1-yl)ethyl]-1H-pyrazol-4-yl}amino)-1,3,5-triazin-2-yl]-2-(hydroxymethyl)phenyl}-6-cyclopropyl-8-fluoroisoquinolin-1(2H)-one |
| 20 | | 4-({4-Amino-6-[3-(6-cyclopropyl-8-fluoro-1-oxoisoquinolin-2(1H)-yl)-2-(hydroxymethyl)phenyl]-1,3,5-triazin-2-yl}amino)-1-(cyclopropylmethyl)-1H-pyrrole-2-carbonitrile |

TABLE 1-2-continued

| 21 | 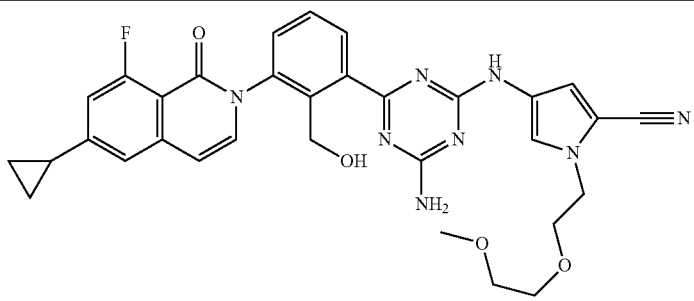 | 4-({4-Amino-6-[3-(6-cyclopropyl-8-fluoro-1-oxoisoquinolin-2(1H)-yl)-2-(hydroxymethyl)phenyl]-1,3,5-triazin-2-yl}amino)-1-[2-(2-methoxyethoxy)ethyl]-1H-pyrrole-2-carbonitrile |
| --- | --- | --- |
| 22 | 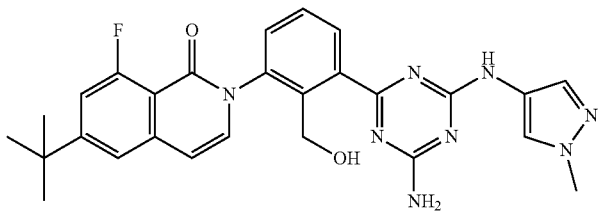 [SMILES: Cn1cc(Nc2nc(N)nc(-c3cccc(-n4ccc5cc(C(C)(C)C)cc(F)c5c4=O)c3CO)n2)cn1] | 2-(3-{4-Amino-6-[(1-methyl-1H-pyrazol-4-yl)amino]-1,3,5-triazin-2-yl}-2-(hydroxymethyl)phenyl)-6-(tert-butyl)-8-fluoroisoquinolin-1(2H)-one |

TABLE 1-3

| 23 | 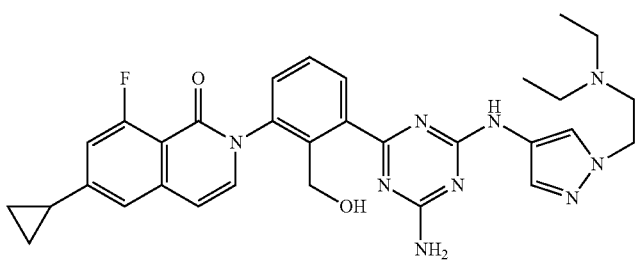 [SMILES: CCN(CC)CCn1cc(Nc2nc(N)nc(-c3cccc(-n4ccc5cc(C6CC6)cc(F)c5c4=O)c3CO)n2)cn1] | 2-{3-[4-Amino-6-({1-[2-(diethylamino)ethyl]-1H-pyrazol-4-yl}amino)-1,3,5-triazin-2-yl]-2-(hydroxymethyl)phenyl}-6-cyclopropyl-8-fluoroisoquinolin-1(2H)-one |
| --- | --- | --- |
| 24 | 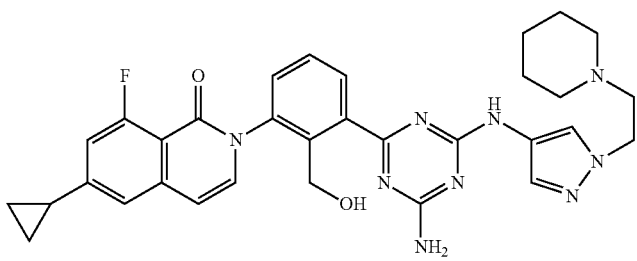 [SMILES: Nc1nc(Nc2cnn(CCN3CCCCC3)c2)nc(-c2cccc(-n3ccc4cc(C5CC5)cc(F)c4c3=O)c2CO)n1] | 2-{3-[4-Amino-6-({1-[2-(piperidin-1-yl)ethyl]-1H-pyrazol-4-yl}amino)-1,3,5-triazin-2-yl]-2-(hydroxymethyl)phenyl}-6-cyclopropyl-8-fluoroisoquinolin-1(2H)-one |
| 25 | 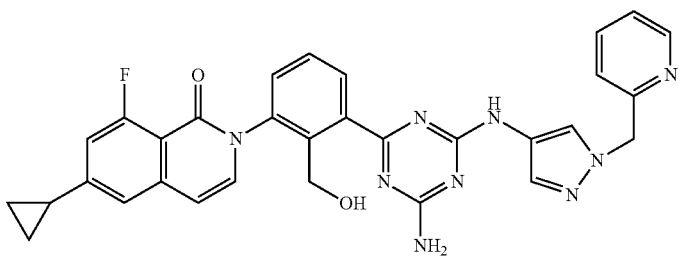 [SMILES: Nc1nc(Nc2cnn(Cc3ccccn3)c2)nc(-c2cccc(-n3ccc4cc(C5CC5)cc(F)c4c3=O)c2CO)n1] | 2-[3-(4-Amino-6-{[1-(pyridin-2-ylmethyl)-1H-pyrazol-4-yl]amino}-1,3,5-triazin-2-yl)-2-(hydroxymethyl)phenyl]-6-cyclopropyl-8-fluoroisoquinolin-1(2H)-one |

TABLE 1-3-continued

| 26 | 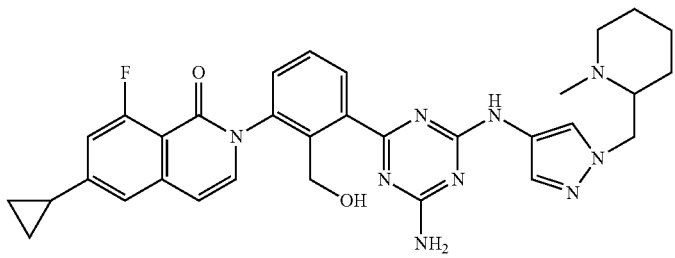 [SMILES: CN1CCCCC1Cn1cc(Nc2nc(N)nc(-c3cccc(-n4ccc5cc(C6CC6)cc(F)c5c4=O)c3CO)n2)cn1] | 2-{3-[4-Amino-6-({1-[(1-methylpiperidin-2-yl)methyl]-1H-pyrazol-4-yl}amino)-1,3,5-triazin-2-yl]-2-(hydroxymethyl)phenyl}-6-cyclopropyl-8-fluoroisoquinolin-1(2H)-one |
| --- | --- | --- |
| 27 | 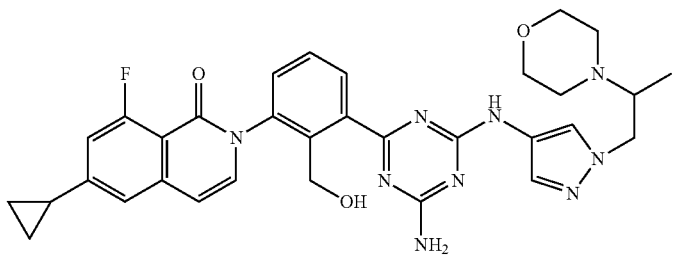 [SMILES: CC(Cn1cc(Nc2nc(N)nc(-c3cccc(-n4ccc5cc(C6CC6)cc(F)c5c4=O)c3CO)n2)cn1)N1CCOCC1] | 2-[3-(4-Amino-6-{[1-(2-morpholinopropyl)-1H-pyrazol-4-yl]amino}-1,3,5-triazin-2-yl)-2-(hydroxymethyl)phenyl]-6-cyclopropyl-8-fluoroisoquinolin-1(2H)-one |
| 28 | 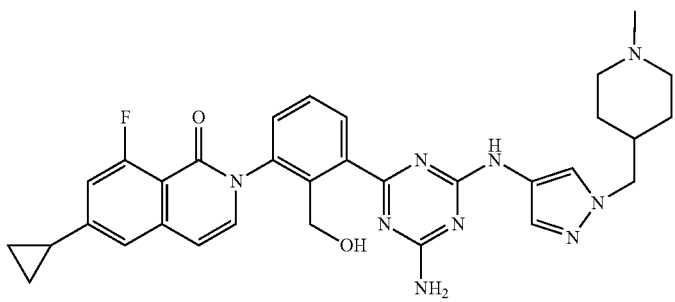 [SMILES: CN1CCC(Cn2cc(Nc3nc(N)nc(-c4cccc(-n5ccc6cc(C7CC7)cc(F)c6c5=O)c4CO)n3)cn2)CC1] | 2-{3-[4-Amino-6-({1-[(1-methylpiperidin-4-yl)methyl]-1H-pyrazol-4-yl}amino)-1,3,5-triazin-2-yl]-2-(hydroxymethyl)phenyl}-6-cyclopropy1-8-fluoroisoquinolin-1(2H)-one |
| 29 | 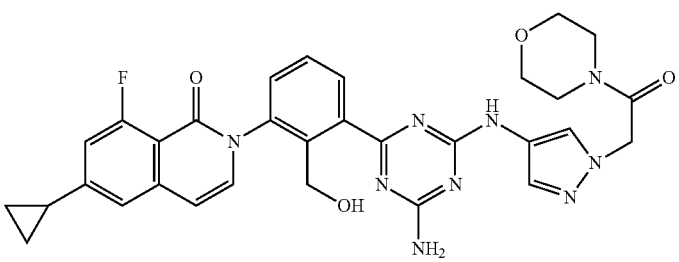 [SMILES: Nc1nc(Nc2cnn(CC(=O)N3CCOCC3)c2)nc(-c2cccc(-n3ccc4cc(C5CC5)cc(F)c4c3=O)c2CO)n1] | 2-[3-(4-Amino-6-{[1-(2-morpholino-2-oxoethyl)-1H-pyrazol-4-yl]amino}-1,3,5-triazin-2-yl)-2-(hydroxymethyl)phenyl]-6-cyclopropyl-8-fluoroisoquinolin-1(2H)-one |
| 30 | 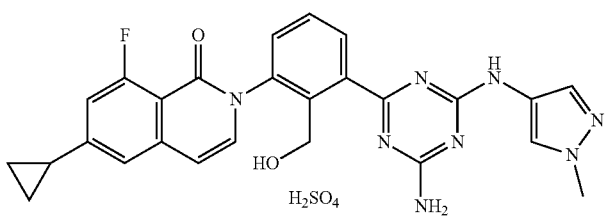 | 2-(3-{4-amino-6-[(1-methyl-1H-pyrazol-4-yl)amino]-1,3,5-triazin-2-yl}-2-(hydroxymethyl)phenyl)-6-cyclopropyl-8-fluoroisoquinolin-1(2H)-one sulfate |
| 31 | 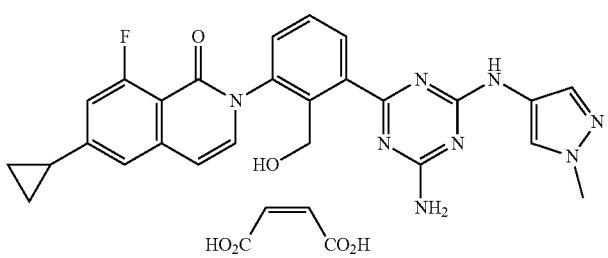 | 2-(3-{4-amino-6-[(1-methyl-1H-pyrazol-4-yl)amino]-1,3,5-triazin-2-yl}-2-(hydroxymethyl)phenyl)-6-cyclopropyl-8-fluoroisoquinolin-1(2H)-one maleate |

TABLE 1-3-continued

| | | |
|---|---|---|
| 32 | 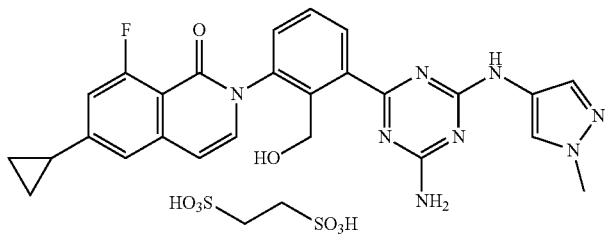 | 2-(3-{4-amino-6-[(1-methyl-1H-pyrazol-4-yl)amino]-1,3,5-triazin-2-yl}-2-(hydroxymethyl)phenyl)-6-cyclopropyl-8-fluoroisoquinolin-1(2H)-one ethane-1,2-disulfonate |
| 33 | 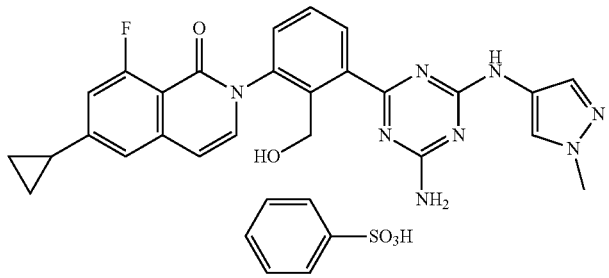 | 2-(3-{4-amino-6-[(1-methyl-1H-pyrazol-4-yl)amino]-1,3,5-triazin-2-yl}-2-(hydroxymethyl)phenyl)-6-cyclopropyl-8-fluoroisoquinolin-1(2H)-one benzenesulfonate |

TABLE 2-1

| Ex. No. | $^1$H-NMR δ (ppm) | LCMS m/z [M + H]$^+$ |
|---|---|---|
| 3 | (DMSO-d6) δ 9.70 (s, 1H), 8.10 (s, 1H), 7.88 (dd, J = 7.7, 1.3 Hz, 1H), 7.62-7.49 (m, 2H), 7.45 (dd, J = 7.8, 1.4 Hz, 1H), 7.38-7.15 (m, 4H), 7.00 (dd, J = 13.2, 1.6 Hz, 1H), 6.62 (dd, J = 7.6, 2.1 Hz, 1H), 5.26-5.00 (m, 1H), 4.61-4.43 (m, 1H), 4.18-4.04 (m, 1H), 3.64-3.52 (m, 1H), 2.13-2.03 (m, 1H), 1.55-1.41 (m, 3H), 1.28-1.15 (m, 1H), 1.14-1.06 (m, 2H), 0.92-0.84 (m, 2H), 0.63-0.52 (m, 1H), 0.49-0.38 (m, 1H), 0.37-0.27 (m, 2H). | 553.2 |
| 4 | (DMSO-d6) δ 9.67 (s, 1H), 8.06 (s, 1H), 7.89 (d, J = 7.7 Hz, 1H), 7.64-7.51 (m, 2H), 7.49-7.42 (m, 1H), 7.39-7.16 (m, 4H), 7.00 (dd, J = 13.2, 1.7 Hz, 1H), 6.62 (dd, J = 7.4, 2.2 Hz, 1H), 5.26-5.10 (m, 1H), 4.99-4.86 (m, 1H), 4.58-4.43 (m, 1H), 4.16-4.03 (m, 1H), 3.62-3.49 (m, 2H), 2.14-2.03 (m, 1H), 1.51-1.39 (m, 6H), 1.14-1.05 (m, 2H), 0.91-0.84 (m, 2H). | 557.2 |
| 5 | (DMSO-d6) δ 9.94-9.43 (m, 1H), 8.14-7.95 (m, 1H), 7.93-7.83 (m, 1H), 7.77 (s, 1H), 7.71-7.51 (m, 2H), 7.50-7.43 (m, 1H), 7.41-7.36 (m, 1H), 7.34 (d, J = 7.4 Hz, 1H), 7.28 (d, J = 1.6 Hz, 1H), 7.00 (dd, J = 13.2, 1.7 Hz, 1H), 6.62 (dd, J = 7.4, 2.1 Hz, 1H), 6.51-6.13 (m, 1H), 5.34-4.90 (m, 1H), 4.72-4.31 (m, 3H), 4.09 (dd, J = 12.0, 9.2 Hz, 1H), 2.14-2.02 (m, 1H), 1.15-1.04 (m, 2H), 0.91-0.84 (m, 2H). | 549.2 |
| 6 | (DMSO-d6) δ 9.68-9.17 (m, 1H), 8.01-7.82 (m, 1H), 7.66-7.59 (m, 1H), 7.59-7.51 (m, 1H), 7.44 (dd, J = 7.8, 1.4 Hz, 1H), 7.34 (s, 1H), 7.32 (d, J = 1.9 Hz, 1H), 7.31-7.24 (m, 2H), 7.00 (dd, J = 13.2, 1.7 Hz, 1H), 6.62 (dd, J = 7.5, 2.0 Hz, 1H), 6.48 (d, J = 1.8 Hz, 1H), 5.33-5.02 (m, 1H), 4.60-4.41 (m, 1H), 4.19-4.01 (m, 1H), 3.64 (s, 3H), 3.04 (s, 6H), 2.15-1.99 (m, 1H), 1.14-1.05 (m, 2H), 0.95-0.81 (m, 2H). | 569.2 |
| 7 | (DMSO-d6) δ 9.92-9.33 (m, 1H), 7.87 (d, J = 7.5 Hz, 1H), 7.62-7.49 (m, 2H), 7.45 (d, J = 7.8 Hz, 1H), 7.40 (s, 1H), 7.33 (d, J = 7.4 Hz, 1H), 7.28 (d, J = 1.6 Hz, 1H), 7.06-6.94 (m, 2H), 6.62 (dd, J = 7.5, 2.1 Hz, 1H), 5.24-4.92 (m, 1H), 4.64-4.35 (m, 1H), 4.13-4.04 (m, 1H), 3.64-3.44 (m, 1H), 2.16-1.94 (m, 1H), 1.15-0.93 (m, 6H), 0.92-0.81 (m, 2H). | 549.2 |
| 8 | (DMSO-d6) δ9.80 (s, 1H), 7.96-7.84 (m, 1H), 7.59-7.50 (m, 2H), 7.45 (d, J = 7.8 Hz, 1H), 7.43-7.25 (m, 4H), 7.07 (s, 1H), 7.00 (dd, J = 13.2, 1.7 Hz, 1H), 6.62 (dd, J = 7.5, 2.1 Hz, 1H), 5.21-5.10 (m, 1H), 5.10-4.94 (m, 1H), 4.66-4.40 (m, 1H), 4.26-3.96 (m, 3H), 3.79-3.58 (m, 2H), 2.14-2.02 (m, 1H), 1.15-1.05 (m, 2H), 0.96-0.83 (m, 2H). | 553.0 |
| 9 | (DMSO-d6) δ9.75 (s, 1H), 7.88 (d, J = 7.7 Hz, 1H), 7.67-7.63 (m, 1H), 7.58-7.53 (m, 2H), 7.50-7.40 (m, 1H), 7.39-7.16 (m, 4H), 7.00 (dd, J = 13.2, 1.7 Hz, 1H), 6.81-6.77 (m, 1H), 6.62 (dd, J = 7.5, 2.1 Hz, 1H), 5.19-5.13 (m, 1H), 4.58-4.47 (m, 1H), 4.19-4.05 (m, 1H), 3.83 (s, 3H), 3.23 (s, 3H), 2.12-2.04 (m, 1H), 1.14-1.07 (m, 2H), 0.91-0.84 (m, 2H). | 576.1 |
| 10 | (DMSO-d6) δ9.72 (s, 1H), 7.88 (d, J = 7.8 Hz, 1H), 7.64-7.48 (m, 2H), 7.45 (dd, J = 7.8, 1.4 Hz, 1H), 7.40-7.25 (m, 4H), 7.06 (d, J = 1.9 Hz, 1H), 7.04-6.94 (m, 1H), 6.66-6.57 (m, 1H), 5.29-5.12 (m, 1H), 4.55-4.45 (m, 1H), 4.14-4.01 (m, 1H), 3.84 (s, 3H), 2.35 (s, 3H), 2.12-2.04 (m, 1H), 1.15-1.06 (m, 2H), 0.91-0.84 (m, 2H). | 540.3 |
| 11 | (DMSO-d6) δ 9.81 (s, 1H), 7.88 (d, J = 7.7 Hz, 1H), 7.68-7.50 (m, 2H), 7.49-7.41 (m, 1H), 7.44-7.25 (m, 4H), 7.12-6.81 (m, 2H), 6.62 (dd, J = 7.5, 2.1 Hz, 1H), 5.29-4.89 (m, 1H), 4.54-4.46 (m, 2H), 4.06 (q, J = 7.3 Hz, 2H), 2.14-2.00 (m, 1H), 1.40 (t, J = 7.2 Hz, 3H), 1.15-1.05 (m, 2H), 0.92-0.83 (m, 2H). | 537.1 |
| 12 | (DMSO-d6) δ 9.80 (s, 1H), 7.96-7.84 (m, 1H), 7.67 (d, J = 1.7 Hz, 1H), 7.59-7.50 (m, 1H), 7.45 (dd, J = 7.9, 1.4 Hz, 1H), 7.43-7.36 (m, 2H), 7.37-7.25 (m, 2H), 7.11-6.78 (m, 2H), 6.62 (dd, J = 7.5, 2.0 Hz, 1H), 5.29-4.89 (m, 1H), 4.70-4.31 (m, 2H), 4.18-4.04 (m, 1H), 2.14-2.02 (m, 1H), 1.48 (d, J = 6.7 Hz, 6H), 1.15-1.05 (m, 2H), 0.92-0.82 (m, 2H). | 551.6 |
| 13 | (DMSO-d6) δ 9.80 (s, 1H), 7.94-7.84 (m, 1H), 7.68-7.50 (m, 3H), 7.50-7.41 (m, 1H), 7.41-7.25 (m, 3H), 7.15-6.81 (m, 2H), 6.62 (dd, J = 7.5, 2.1 Hz, 1H), 5.27-4.92 (m, 1H), 4.55-4.45 (m, 1H), 4.25-4.13 (m, 2H), 4.14-4.03 (m, 1H), 3.69-3.58 (m, 2H), 3.24 (s, 3H), 2.14-2.02 (m, 1H), 1.15-1.03 (m, 2H), 0.98-0.81 (m, 2H). | 567.6 |
| 14 | (DMSO-d6) δ 12.58 (s, 1H), 9.71 (s, 1H), 8.07 (s, 1H), 7.88 (dd, J = 7.6, 1.3 Hz, 1H), 7.69-7.51 (m, 2H), 7.45 (dd, J = 7.8, 1.4 Hz, 1H), 7.38- | 485.2 |

TABLE 2-1-continued

| Ex. No. | $^1$H-NMR δ (ppm) | LCMS m/z [M + H]$^+$ |
|---|---|---|
|  | 7.14 (m, 4H), 7.00 (dd, J = 13.2, 1.6 Hz, 1H), 6.62 (dd, J = 7.5, 2.1 Hz, 1H), 5.27-5.00 (m, 1H), 4.57-4.42 (m, 1H), 4.16-4.01 (m, 1H), 2.13-2.02 (m, 1H), 1.13-1.05 (m, 2H), 0.91-0.83 (m, 2H). |  |
| 15 | (DMSO-d6) δ 9.82 (s, 1H), 7.91-7.84 (m, 1H), 7.64 (s, 1H), 7.59-7.41 (m, 3H), 7.41-7.25 (m, 5H), 7.13-7.07 (m, 1H), 7.04-6.91 (m, 1H), 6.62 (dd, J = 7.5, 2.1 Hz, 1H), 5.20-5.11 (m, 1H), 4.67 (s, 2H), 4.55-4.46 (m, 1H), 4.17-4.04 (m, 1H), 2.15-2.01 (m, 1H), 1.15-1.01 (m, 2H), 0.92-0.81 (m, 2H). | 566.5 |
| 16 | (DMSO-d6) δ 9.71 (s, 1H), 8.04 (s, 1H), 7.95-7.85 (m, 1H), 7.63 (s, 1H), 7.55 (t, J = 7.7 Hz, 1H), 7.45 (dd, J = 7.9, 1.4 Hz, 1H), 7.33 (d, J = 7.4 Hz, 2H), 7.28 (d, J = 1.7 Hz, 2H), 7.00 (dd, J = 13.2, 1.7 Hz, 1H), 6.62 (dd, J = 7.2, 2.3 Hz, 1H), 5.24-4.97 (m, 1H), 4.57-4.43 (m, 1H), 4.23-4.04 (m, 3H), 3.58-3.52 (m, 4H), 2.76-2.62 (m, 2H), 2.43-2.36 (m, 4H), 2.13-2.04 (m, 1H), 1.14-1.07 (m, 2H), 0.91-0.84 (m, 2H). | 598.4 |
| 17 | (DMSO-d6) δ 9.70 (s, 1H), 8.38 (s, 1H), 8.05-7.85 (m, 1H), 7.65-7.41 (m, 3H), 7.33 (d, J = 7.4 Hz, 2H), 7.28 (d, J = 1.7 Hz, 1H), 7.00 (dd, J = 13.2, 1.8 Hz, 1H), 6.62 (d, J = 7.1 Hz, 1H), 5.24-5.00 (m, 1H), 4.58-4.41 (m, 1H), 4.18-4.04 (m, 3H), 2.56-2.54 (m, 2H), 2.20-2.12 (m, 6H), 2.10-2.04 (m, 1H), 1.14-1.06 (m, 2H), 0.92-0.85 (m, 2H). | 556.2 |

TABLE 2-2

| Ex. No. | $^1$H-NMR δ (ppm) | LCMS m/z [M + H]$^+$ |
|---|---|---|
| 18 | (DMSO-d6) δ 9.71 (s, 1H), 8.28 (s, 1H), 8.03 (s, 1H), 7.96-7.82 (m, 1H), 7.64-7.49 (m, 2H), 7.45 (d, J = 7.4 Hz, 1H), 7.38-7.25 (m, 3H), 7.00 (dd, J = 13.1, 1.7 Hz, 1H), 6.66-6.58 (m, 1H), 5.24-4.98 (m, 1H), 4.60-4.44 (m, 1H), 4.16-4.01 (m, 3H), 2.21-2.04 (m, 9H), 1.95-1.81 (m, 2H), 1.14-1.06 (m, 2H), 0.91-0.84 (m, 2H). | 570.2 |
| 19 | (DMSO-d6) δ 9.70 (s, 1H), 8.34 (s, 1H), 8.05 (s, 1H), 7.97-7.83 (m, 1H), 7.64-7.41 (m, 3H), 7.38-7.24 (m, 3H), 7.00 (dd, J = 13.2, 1.7 Hz, 1H), 6.65-6.59 (m, 1H), 5.24-4.98 (m, 1H), 4.57-4.44 (m, 1H), 4.20-4.02 (m, 3H), 2.85-2.74 (m, 2H), 2.47-2.41 (m, 4H), 2.13-2.03 (m, 1H), 1.85-1.60 (m, 4H), 1.14-1.05 (m, 2H), 0.91-0.84 (m, 2H). | 582.3 |
| 20 | (DMSO-d6) δ 9.80 (s, 1H), 7.88 (d, J = 7.6 Hz, 1H), 7.67-7.50 (m, 1H), 7.49-7.42 (m, 1H), 7.40-7.25 (m, 4H), 7.10-7.04 (m, 1H), 7.00 (dd, J = 13.2, 1.6 Hz, 1H), 6.62 (dd, J = 7.4, 2.1 Hz, 1H), 5.16 (br.s, 1H), 4.54-4.46 (m, 1H), 4.15-4.03 (m, 1H), 3.89 (d, J = 7.1 Hz, 2H), 2.14-2.02 (m, 1H), 1.30-1.13 (m, 1H), 1.17-1.01 (m, 2H), 0.92-0.81 (m, 2H), 0.63-0.53 (m, 2H), 0.46-0.37 (m, 2H). | 563.5 |
| 21 | (DMSO-d6) δ 9.81 (s, 1H), 7.94-7.84 (m, 1H), 7.62-7.50 (m, 1H), 7.49-7.41 (m, 1H), 7.40-7.25 (m, 4H), 7.11-6.95 (m, 2H), 6.62 (dd, J = 7.4, 2.1 Hz, 1H), 5.20-5.11 (m, 1H), 4.55-4.45 (m, 1H), 4.20-4.04 (m, 3H), 3.78-3.67 (m, 2H), 3.56-3.46 (m, 2H), 3.46-3.35 (m, 2H), 3.22 (s, 3H), 2.14-2.03 (m, 1H), 1.15-1.03 (m, 2H), 0.92-0.81 (m, 2H). | 611.6 |
| 22 | (DMSO-d6) δ 9.71 (s, 1H), 8.00 (s, 1H), 7.96-7.81 (m, 1H), 7.65-7.42 (m, 4H), 7.40-7.08 (m, 4H), 6.77-6.69 (m, 1H), 5.25-4.98 (m, 1H), 4.56-4.45 (m, 1H), 4.18-4.03 (m, 3H), 3.81 (s, 3H), 1.36 (s, 9H). | 515.2 |
| 23 | (DMSO-d6) δ 9.71 (s, 1H), 8.02 (s, 1H), 7.92-7.84 (m, 1H), 7.63 (s, 1H), 7.59-7.42 (m, 2H), 7.40-7.31 (m, 2H), 7.31-7.22 (m, 2H), 7.05-6.94 (m, 1H), 6.62 (d, J = 7.3 Hz, 1H), 5.26-5.00 (m, 1H), 4.60-4.41 (m, 1H), 4.21-3.96 (m, 3H), 2.83-2.68 (m, 2H), 2.56-2.42 (m, 4H), 2.14-2.00 (m, 1H), 1.17-1.03 (m, 2H), 0.97-0.80 (m, 8H). | 584.6 |
| 24 | (DMSO-d6) δ 9.71 (s, 1H), 8.03 (s, 1H), 7.91-7.85 (m, 1H), 7.63 (s, 1H), 7.60-7.41 (m, 3H), 7.41-7.22 (m, 3H), 7.04-6.96 (m, 1H), 6.67-6.57 (m, 1H), 5.25-4.98 (m, 1H), 4.58-4.44 (m, 1H), 4.21-4.03 (m, 3H), 2.72-2.59 (m, 2H), 2.43-2.29 (m, 4H), 2.13-2.03 (m, 1H), 1.53-1.29 (m, 6H), 1.14-1.06 (m, 2H), 0.93-0.82 (m, 2H). | 596.6 |
| 25 | (DMSO-d6) δ 9.80 (s, 1H), 8.54 (s, 1H), 8.20 (s, 1H), 7.93-7.84 (m, 1H), 7.81-7.73 (m, 1H), 7.71 (t, J = 7.6 Hz, 1H), 7.55 (t, J = 7.6 Hz, 1H), 7.45 (d, J = 7.1 Hz, 1H), 7.39-7.24 (m, 5H), 7.03-6.94 (m, 1H), 6.62 (d, J = 7.3 Hz, 1H), 5.38 (s, 2H), 5.23-5.02 (m, 1H), 4.55-4.45 (m, 1H), 4.21-4.13 (m, 1H), 2.11-2.04 (m, 1H), 1.13-1.07 (m, 2H), 0.90-0.84 (m, 2H). | 576.4 |
| 26 | (DMSO-d6) δ 9.72 (s, 1H), 8.02 (s, 1H), 7.92-7.85 (m, 1H), 7.62 (s, 1H), 7.59-7.51 (m, 1H), 7.49-7.43 (m, 1H), 7.40-7.25 (m, 4H), 7.03-6.97 (m, 1H), 6.65-6.58 (m, 1H), 5.23-5.14 (m, 1H), 4.54-4.45 (m, 1H), 4.38-4.29 (m, 1H), 4.15-4.04 (m, 1H), 3.99-3.88 (m, 1H), 2.80-2.70 (m, 1H), 2.31-2.22 (m, 4H), 2.13-1.98 (m, 1H), 1.67-1.55 (m, 1H), 1.54-1.45 (m, 1H), 1.28-1.06 (m, 6H), 0.90-0.84 (m, 2H). | 596.4 |
| 27 | (DMSO-d6) δ 9.72 (s, 1H), 8.02 (s, 1H), 7.92-7.85 (m, 1H), 7.64 (s, 1H), 7.58-7.52 (m, 1H), 7.47-7.42 (m, 1H), 7.39-7.20 (m, 4H), 7.00 (d, J = 13.4 Hz, 1H), 6.62 (d, J = 7.4 Hz, 1H), 5.22-5.17 (m, 1H), 4.56-4.45 (m, 1H), 4.21-4.14 (m, 1H), 4.13-4.06 (m, 1H), 3.98-3.90 (m, 1H), 3.57-3.46 (m, 5H), 2.62-2.37 (m, 4H), 2.12-2.04 (m, 1H), 1.13-1.06 (m, 2H), 0.90-0.85 (m, 5H). | 612.1 |
| 28 | (DMSO-d6) δ 10.17-9.92 (m, 1H), 8.09 (s, 1H), 7.88-7.83 (m, 1H), 7.70-7.65 (m, 1H), 7.63-7.38 (m, 4H), 7.33 (d, J = 7.5 Hz, 1H), 7.29 (s, 1H), 7.00 (d, J = 13.1 Hz, 1H), 6.63 (d, J = 7.4 Hz, 1H), 4.56-4.48 (m, 1H), 4.17-4.04 (m, 3H), 3.23-2.94 (m, 4H), 2.82-2.75 (m, 3H), 2.13-2.04 (m, 2H), 2.01-1.85 (m, 1H), 1.75-1.63 (m, 1H), 1.61-1.45 (m, 5H), 1.15-1.07 (m, 2H), 0.91-0.84 (m, 2H). | 596.6 |
| 29 | (DMSO-d6) δ 9.75 (s, 1H), 7.96 (s, 1H), 7.92-7.85 (m, 1H), 7.67 (s, 1H), 7.60-7.51 (m, 1H), 7.49-7.41 (m, 1H), 7.41-7.14 (m, 4H), 7.00 (d, J = 13.1 Hz, 1H), 6.61 (d, J = 8.0 Hz, 1H), 5.26-5.14 (m, 1H), 5.08 (s, 2H), 4.58-4.42 (m, 1H), 4.20-4.03 (m, 1H), 3.63-3.42 (m, 8H), 2.15-2.03 (m, 1H), 1.12-1.05 (m, 2H), 0.94-0.80 (m, 2H). | 612.4 |
| 30 | (DMSO-d6) δ 10.55 (s, 1H), 8.23 (s, 1H), 8.06 (s, 1H), 7.93-7.75 (m, 1H), 7.72-7.67 (m, 1H), 7.66-7.48 (m, 3H), 7.37-7.26 (m, 1H), 7.01 (dd, J = 13.2, 1.7 Hz, 1H), 6.64 (dd, J = 7.4, 2.1 Hz, 1H), 4.64-4.50 (m, 1H), 4.23-4.16 (m, 1H), 3.84 (s, 3H), 2.14-2.03 (m, 1H), 1.17-1.05 (m, 2H), 0.92-0.83 (m, 2H). | 499.2 |
| 31 | (DMSO-d6) δ 9.86 (s, 1H), 8.01 (s, 1H), 7.97-7.79 (m, 1H), 7.67-7.51 (m, 2H), 7.52-7.36 (m, 3H), 7.37-7.31 (m, 1H), 7.31-7.25 (m, 1H), 7.00 (dd, J = 13.3, 1.7 Hz, 1H), 6.62 (dd, J = 7.5, 2.1 Hz, 1H), 6.26 (s, 2H), 4.60-4.41 (m, 1H), 4.23-4.01 (m, 1H), 3.80 (s, 3H), 2.17-2.00 (m, 1H), 1.19-1.01 (m, 2H), 0.95-0.78 (m, 2H). | 499.2 |
| 32 | (DMSO-d6) δ 10.81 (s, 1H), 8.54 (s, 1H), 8.14-8.04 (m, 1H), 7.91-7.48 (m, 5H), 7.37-7.31 (m, 1H), 7.31-7.28 (m, 1H), 7.01 (dd, J = 13.2, 1.7 Hz, 1H), 6.65 (dd, J = 7.5, 2.1 Hz, 1H), 4.66-4.52 (m, 1H), 4.28-4.17 (m, 1H), 3.84 (s, 3H), 2.66-2.61 (m, 1H), 2.14-2.02 (m, 1H), 1.16-1.05 (m, 2H), 0.93-0.82 (m, 2H). | 499.2 |
| 33 | (DMSO-d6) δ 10.57 (s, 1H), 8.28 (s, 1H), 8.06 (s, 1H), 7.93-7.76 (m, 1H), 7.70 (s, 1H), 7.67-7.48 (m, 5H), 7.40-7.25 (m, 1H), 7.01 (dd, J = 13.2, 1.7 Hz, 1H), 6.64 (dd, J = 7.5, 2.1 Hz, 1H), 4.62-4.52 (m, 1H), 4.23-4.16 (m, 1H), 3.84 (s, 3H), 2.14-2.03 (m, 1H), 1.15-1.06 (m, 2H), 0.92-0.83 (m, 2H). | 499.2 |

Example 34

[Method for Production of the Compound (I) Corresponding to the Prodrug of the Example Compound 1]

2-{4-Amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl octate

[Chemical Formula 12]

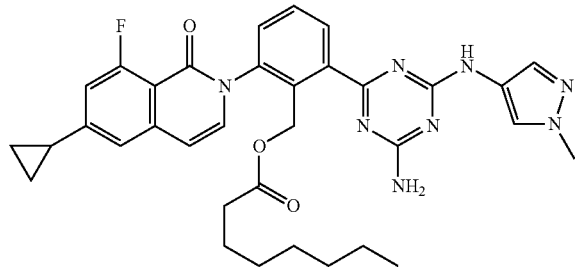

To a solution of 2-(3-{4-amino-6-[(1-methyl-1H-pyrazol-4-yl)amino]-1,3,5-triazin-2-yl}-2-(hydroxymethyl)phenyl)-6-cyclopropyl-8-fluoroisoquinolin-1(2H)-one (0.2 g, 0.4 mmol) which was afforded in the Example 1 in DMF (8 mL), pyridine (0.13 mL, 1.6 mmol) and n-octanoyl chloride (0.14 mL, 0.8 mmol) were added dropwise and stirred at ambient temperature for 16 hours. Water (50 mL) was added to the reaction mixture, and extracted with ethyl acetate (3×50 mL). The combined organic layer was washed with water, 1M hydrochloric acid solution, saturated sodium hydrogen carbonate solution and brine, dried over sodium sulfate, filtered and concentrated. The crude material was purified by chromatography on silica gel, eluted with chloroform/methanol to afford the titled compound (201 mg).

$^1$H NMR (400 MHz, DMSO-$d_6$) δ 9.58 (s, 1H), 7.99 (s, 1H), 7.88-7.73 (m, 1H), 7.69-7.55 (m, 2H), 7.52-7.42 (m, 1H), 7.37 (dd, J=20.5, 7.4 Hz, 1H), 7.26 (d, J=1.6 Hz, 1H), 7.20-7.10 (m, 2H), 6.99 (dd, J=13.2, 1.6 Hz, 1H), 6.60 (dd, J=7.5, 2.0 Hz, 1H), 5.51-5.37 (m, 1H), 5.17-5.04 (m, 1H), 3.79 (s, 3H), 2.12-2.02 (m, 1H), 1.94 (t, J=7.5 Hz, 2H), 1.27-1.00 (m, 10H), 1.02-0.90 (m, 2H), 0.91-0.76 (m, 5H); LCMS (m/z): 625.15 [M+H]$^+$.

Example 35-84

Each of the corresponding Example compounds (I) as a prodrug of the Example compound 1 shown in the following [Table 3-1] to [Table 3-6] was prepared according to the procedure described in the above Example 34 or modified procedure well known in the art of organic chemistry if needed, using appropriate starting materials (those materials are obtained from commercial sources, or are prepared by literature procedures or modifications of literature procedures known to persons skilled in the art).

The physicochemical data of each compound were shown in the following [Table 4-1] to [Table 4-4].

TABLE 3-1

| Ex. No. | Structure | Name |
|---|---|---|
| 35 | 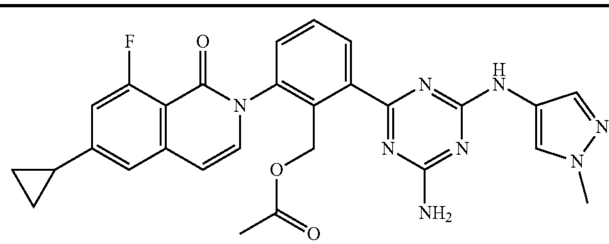 | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl acetate |
| 36 | 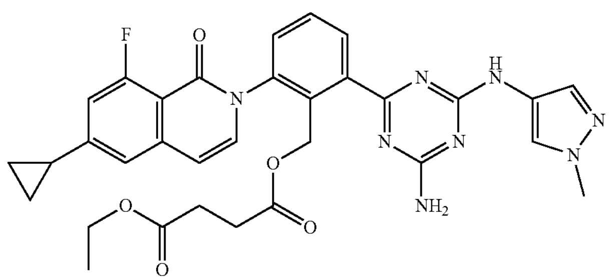 [SMILES: CCOC(=O)CCC(=O)OCc1c(-c2nc(N)nc(Nc3cnn(C)c3)n2)cccc1-n1ccc2cc(C3CC3)cc(F)c2c1=O] | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl ethyl succinate |
| 37 | 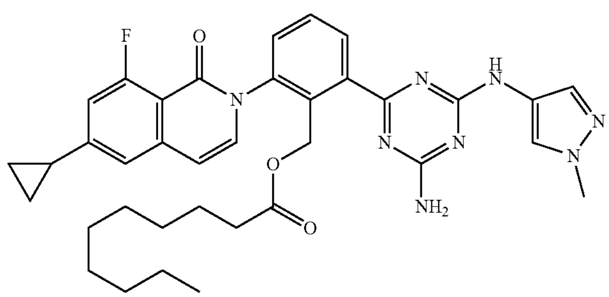 [SMILES: CCCCCCCCCC(=O)OCc1c(-c2nc(N)nc(Nc3cnn(C)c3)n2)cccc1-n1ccc2cc(C3CC3)cc(F)c2c1=O] | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl decanoate |

TABLE 3-1-continued

| Ex. No. | Structure | Name |
|---|---|---|
| 38 | 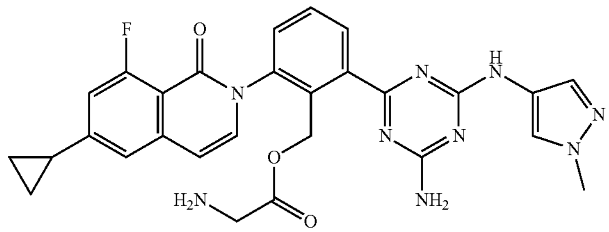 [SMILES: Cn1cc(Nc2nc(N)nc(-c3cccc(-n4ccc5cc(C6CC6)cc(F)c5c4=O)c3COC(=O)CN)n2)cn1] | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-aminoacetate |
| 39 | 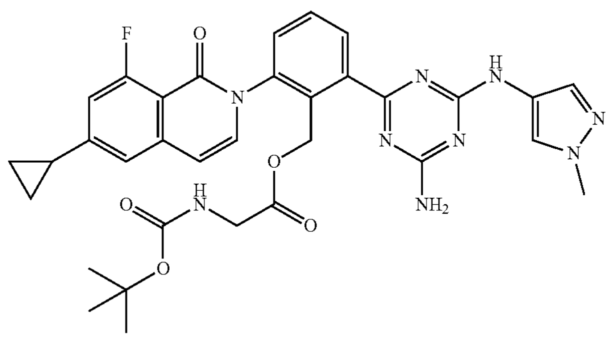 [SMILES: Cn1cc(Nc2nc(N)nc(-c3cccc(-n4ccc5cc(C6CC6)cc(F)c5c4=O)c3COC(=O)CNC(=O)OC(C)(C)C)n2)cn1] | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-[(tert-butoxycarbonyl)amino]acetate |
| 40 | 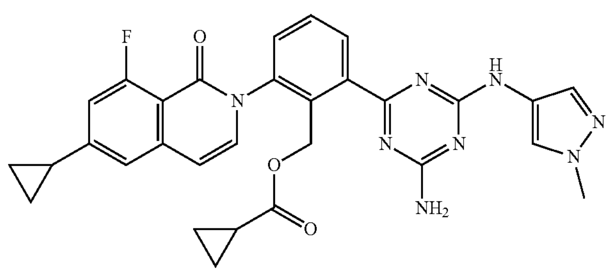 [SMILES: Cn1cc(Nc2nc(N)nc(-c3cccc(-n4ccc5cc(C6CC6)cc(F)c5c4=O)c3COC(=O)C3CC3)n2)cn1] | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl cyclopropanecarboxylate |
| 41 | 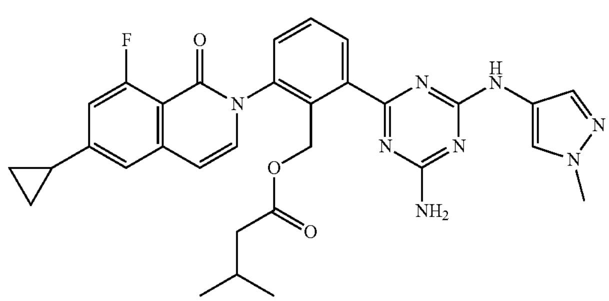 [SMILES: CC(C)CC(=O)OCc1c(-c2nc(N)nc(Nc3cnn(C)c3)n2)cccc1-n1ccc2cc(C3CC3)cc(F)c2c1=O] | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 3-methylbutanoate |
| 42 | 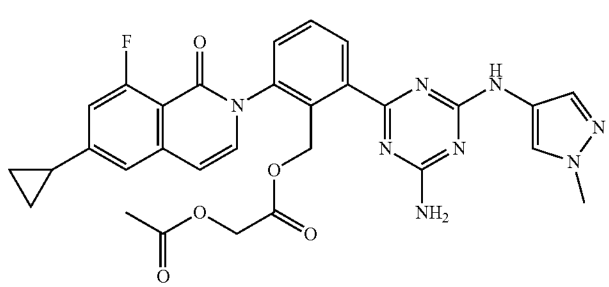 [SMILES: CC(=O)OCC(=O)OCc1c(-c2nc(N)nc(Nc3cnn(C)c3)n2)cccc1-n1ccc2cc(C3CC3)cc(F)c2c1=O] | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-acetoxyacetate |

TABLE 3-1-continued

| Ex. No. | Structure | Name |
|---|---|---|
| 43 | 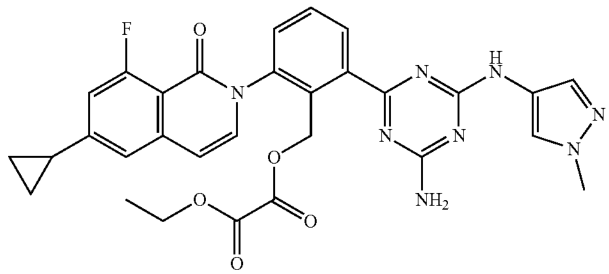 [SMILES: CCOC(=O)C(=O)OCc1c(-c2nc(N)nc(Nc3cnn(C)c3)n2)cccc1-n1ccc2cc(C3CC3)cc(F)c2c1=O] | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl ethyl oxalate |
| 44 | 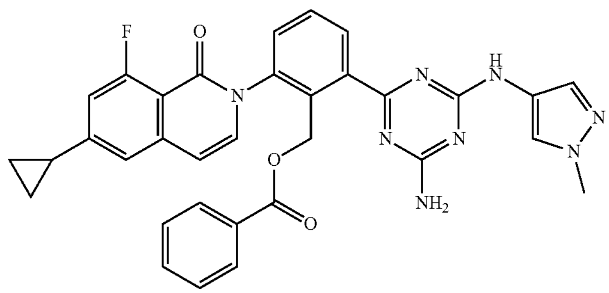 [SMILES: Cn1cc(Nc2nc(N)nc(-c3cccc(-n4ccc5cc(C6CC6)cc(F)c5c4=O)c3COC(=O)c3ccccc3)n2)cn1] | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl benzoate |

TABLE 3-2

| Ex. No. | Structure | Name |
|---|---|---|
| 45 | 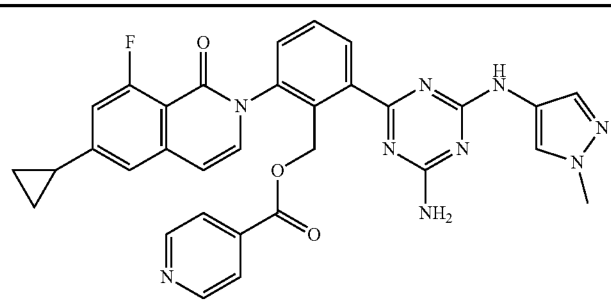 | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl isonicotinate |
| 46 | 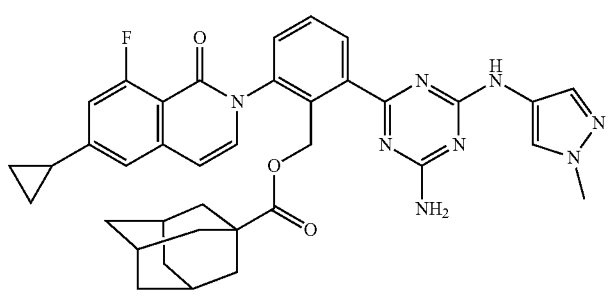 [SMILES: Cn1cc(Nc2nc(N)nc(-c3cccc(-n4ccc5cc(C6CC6)cc(F)c5c4=O)c3COC(=O)C34CC5CC(CC(C5)C3)C4)n2)cn1] | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl adamantane-1-carboxylate |
| 47 | 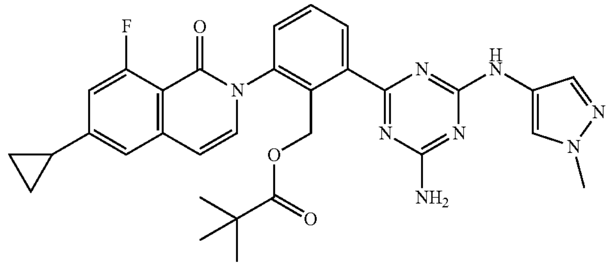 [SMILES: Cn1cc(Nc2nc(N)nc(-c3cccc(-n4ccc5cc(C6CC6)cc(F)c5c4=O)c3COC(=O)C(C)(C)C)n2)cn1] | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl pivalate |

TABLE 3-2-continued

| 48 | 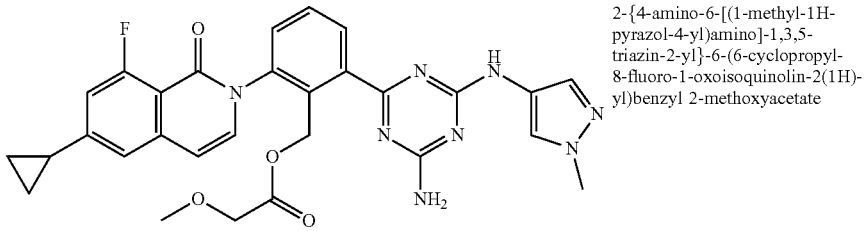 | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-methoxyacetate |
| 49 | 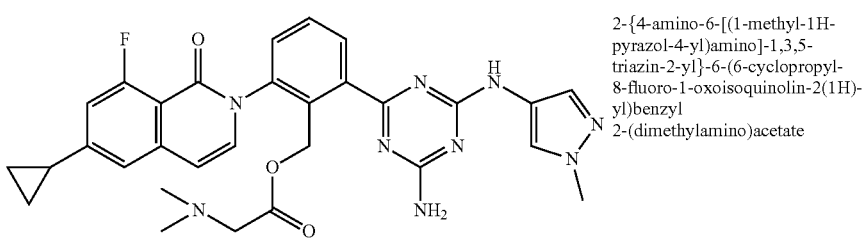 | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-(dimethylamino)acetate |
| 50 | 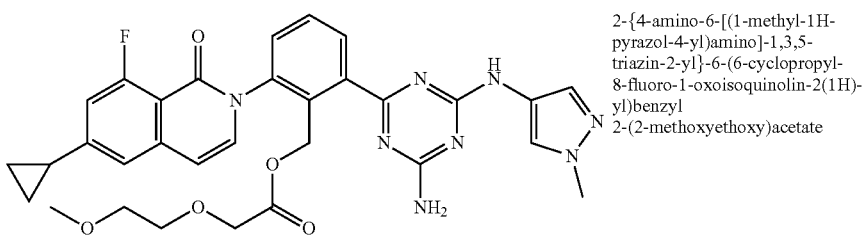 | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-(2-methoxyethoxy)acetate |
| 51 | 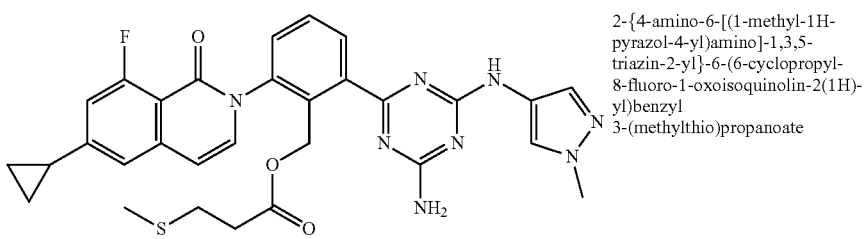 | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 3-(methylthio)propanoate |
| 52 | 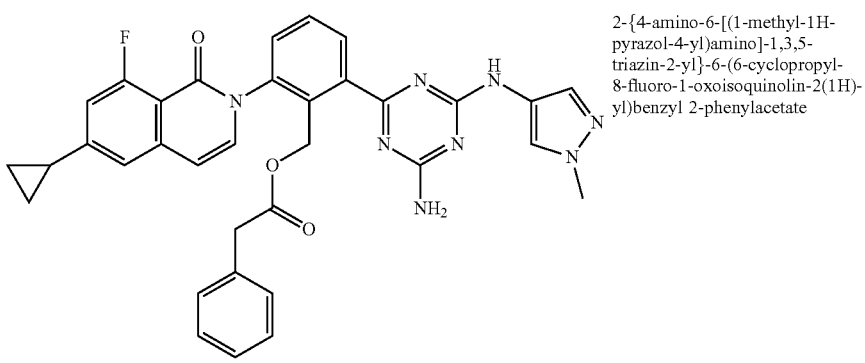 | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-phenylacetate |

TABLE 3-2-continued

| | | |
|---|---|---|
| 53 | 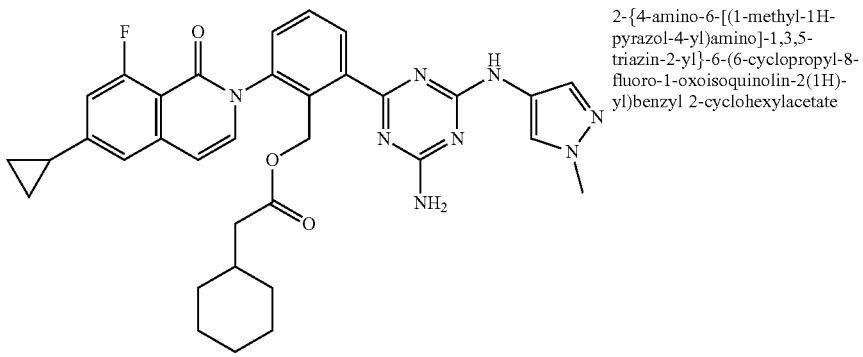 | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-cyclohexylacetate |

TABLE 3-3

| | | |
|---|---|---|
| 54 | 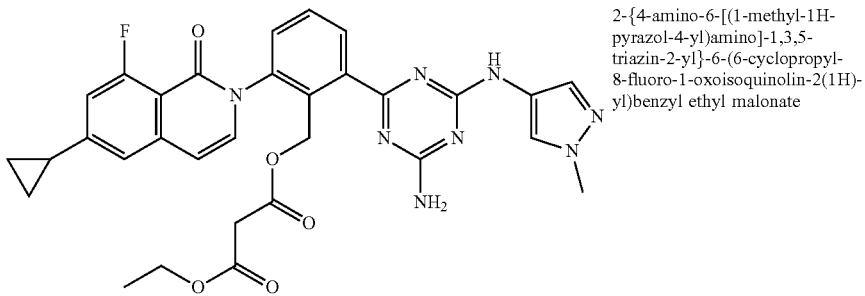 | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl ethyl malonate |
| 55 | 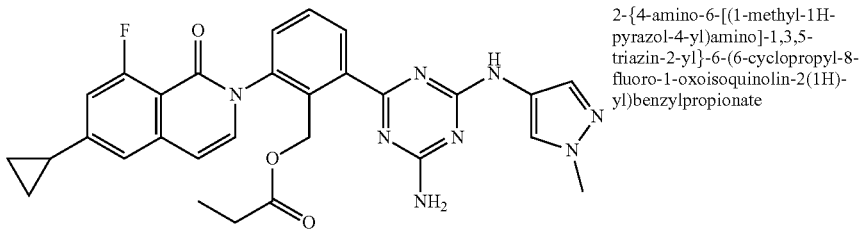 | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzylpropionate |
| 56 | 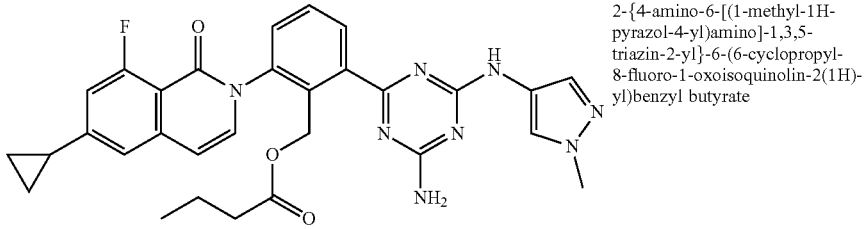 | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl butyrate |
| 57 | 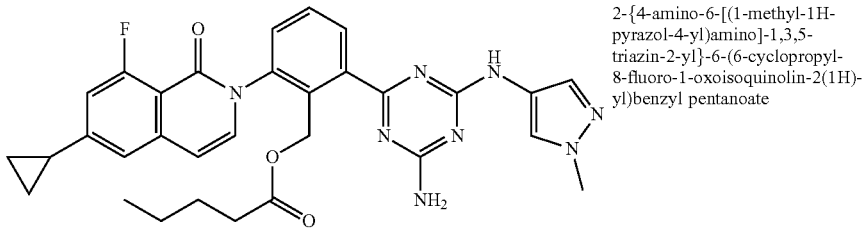 | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl pentanoate |

TABLE 3-3-continued

| | | |
|---|---|---|
| 58 | | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl hexanoate |
| 59 | | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl heptanoate |
| 60 | | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl nonanoate |
| 61 | | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl isobutyrate |
| 62 | | (S)-2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-[(tert-butoxycarbonyl)amino]propanoate |

TABLE 3-4

| 63 | 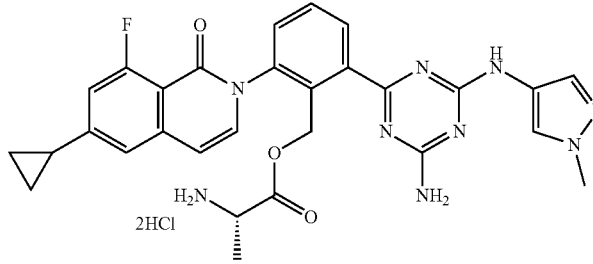 | (S)-2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-aminopropanoate dihydrochloride |
| --- | --- | --- |
| 64 | 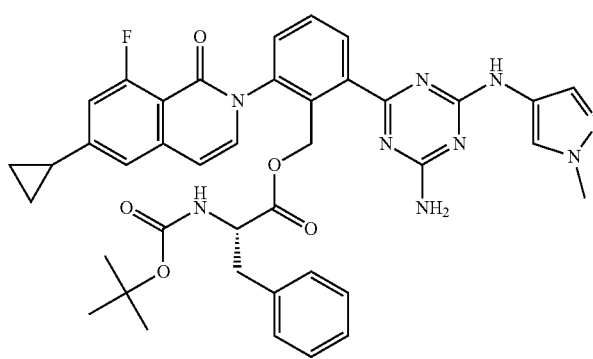 | (S)-2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-[(tert-butoxycarbonyl)amino]-3-phenylpropanoate |
| 65 | 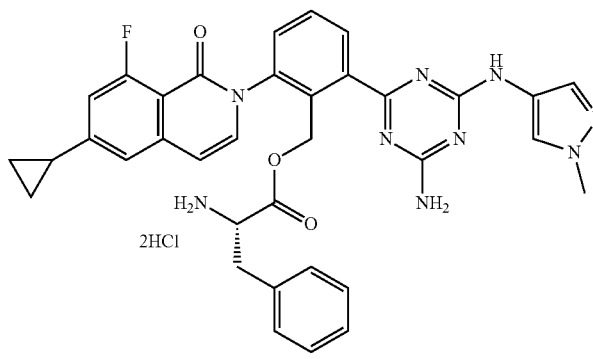 | (S)-2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-amino-3-phenylpropanoate dihydrochloride |
| 66 | 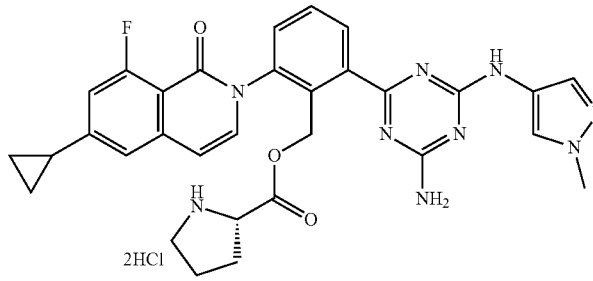 | (S)-2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl pyrrolidine-2-carboxylate dihydrochloride |
| 67 | 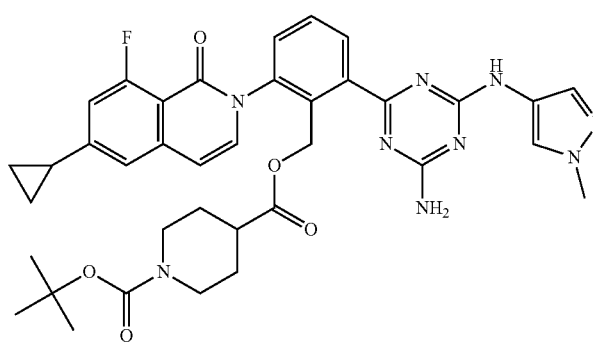 | 4-(2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl) 1-tert-butyl piperidine-1,4-dicarboxylate |

TABLE 3-4-continued

| | | |
|---|---|---|
| 68 | | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl piperidine-4-carboxylate dihydrochloride |
| 69 | | (R)-2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-[(tert-butoxycarbonyl)amino]propanoate |
| 70 | | (R)-2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-aminopropanoate dihydrochloride |
| 71 | | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-ethoxyacetate |

TABLE 3-5

| | | |
|---|---|---|
| 72 | | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-phenoxyacetate |

TABLE 3-5-continued

| 73 | 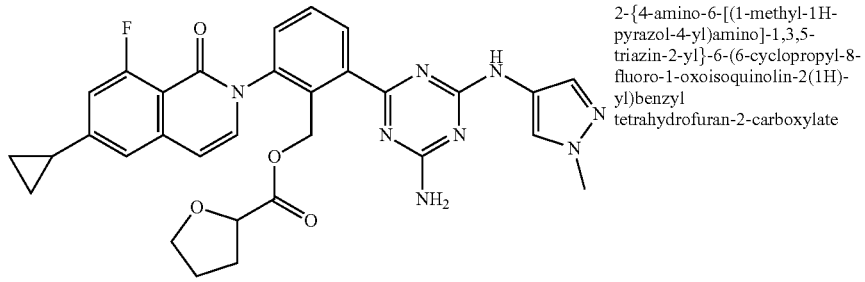 | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl tetrahydrofuran-2-carboxylate |
| 74 | 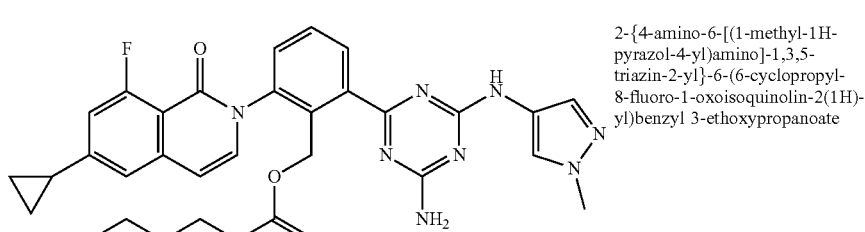 | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 3-ethoxypropanoate |
| 75 | 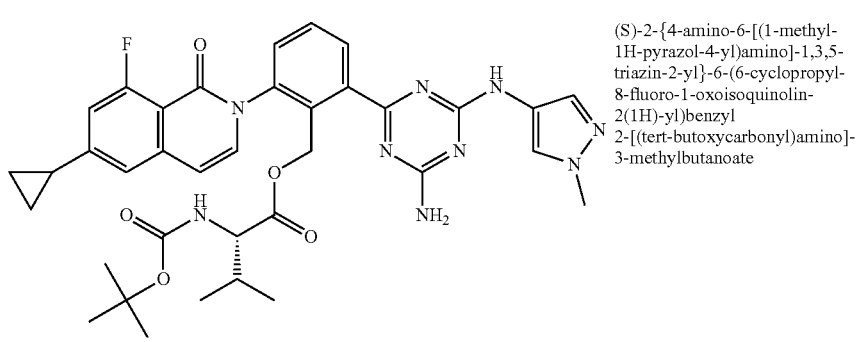 | (S)-2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-[(tert-butoxycarbonyl)amino]-3-methylbutanoate |
| 76 | 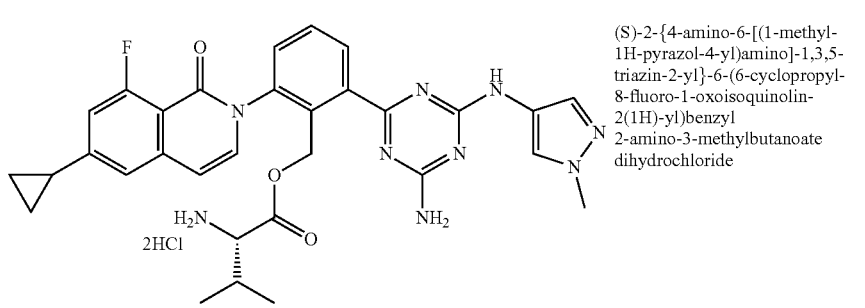 | (S)-2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-amino-3-methylbutanoate dihydrochloride |
| 77 | 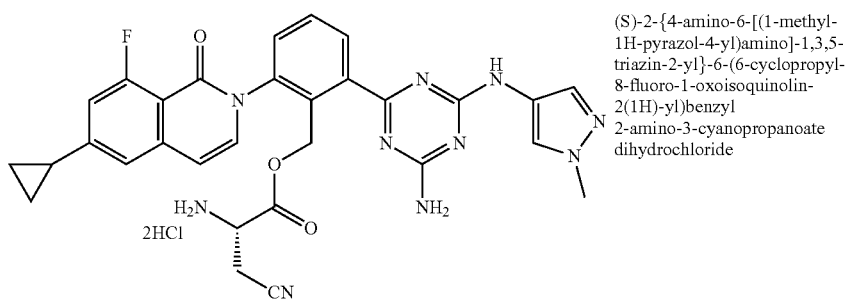 | (S)-2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-amino-3-cyanopropanoate dihydrochloride |

TABLE 3-5-continued

| 78 | 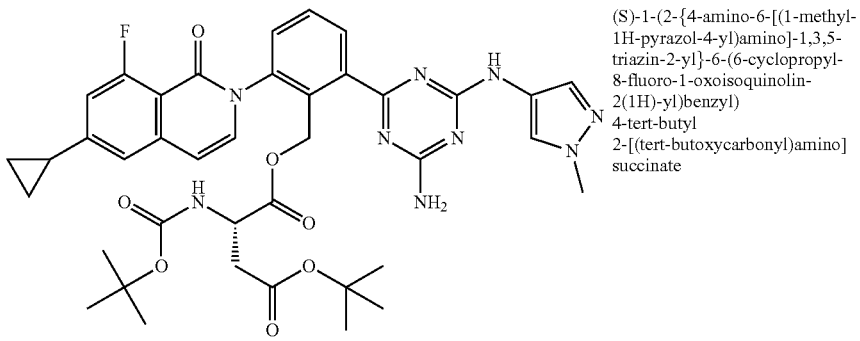 | (S)-1-(2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl) 4-tert-butyl 2-[(tert-butoxycarbonyl)amino]succinate |
|---|---|---|
| 79 | 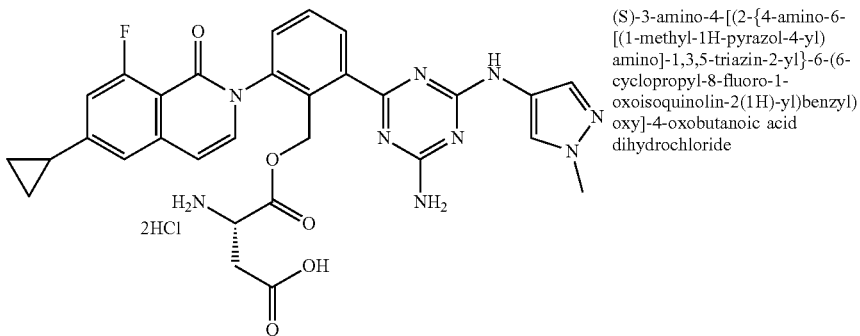 | (S)-3-amino-4-[(2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl)oxy]-4-oxobutanoic acid dihydrochloride |
| 80 | 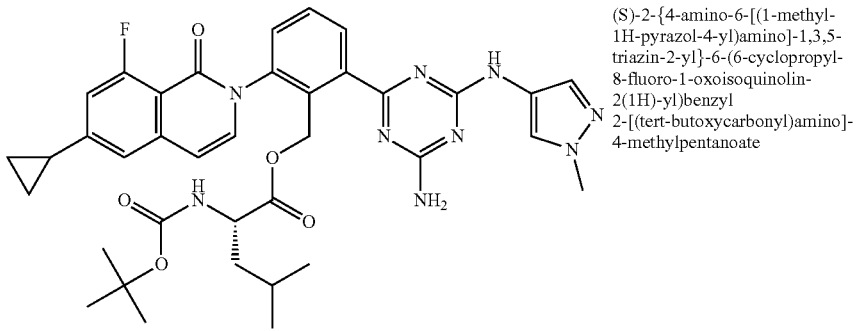 | (S)-2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-[(tert-butoxycarbonyl)amino]-4-methylpentanoate |

TABLE 3-6

| 81 | 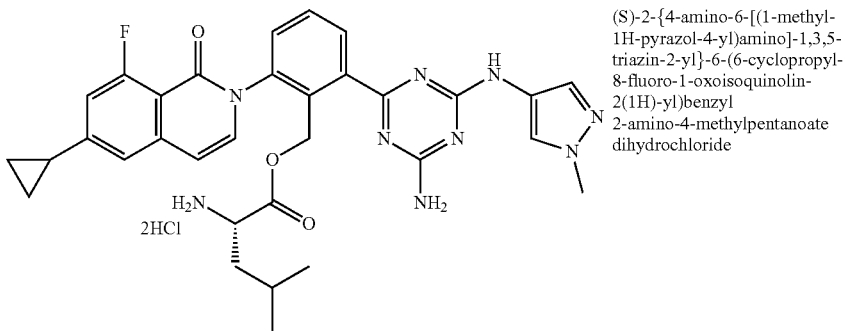 | (S)-2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-amino-4-methylpentanoate dihydrochloride |
|---|---|---|

TABLE 3-6-continued

| | | |
|---|---|---|
| 82 | 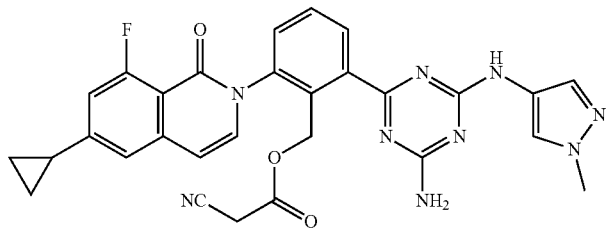 | 2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2-cyanoacetate |
| 83 | 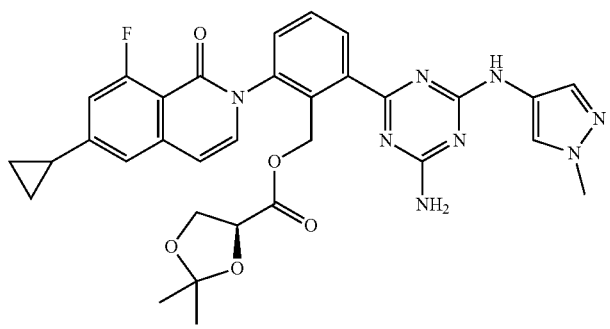 | (S)-2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2,2-dimethyl-1,3-dioxolane-4-carboxylate |
| 84 | 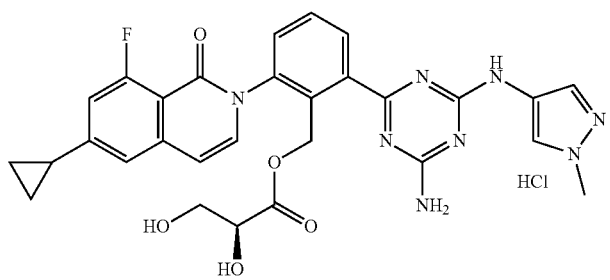 | (S)-2-{4-amino-6-[(1-methyl-1H-pyrazol-4-yl)amino]-1,3,5-triazin-2-yl}-6-(6-cyclopropyl-8-fluoro-1-oxoisoquinolin-2(1H)-yl)benzyl 2,3-dihydroxypropanoate hydrochloride |

TABLE 4-1

| Ex. No. | $^1$H-NMR δ (ppm) | LCMS m/z [M + H]$^+$ |
|---|---|---|
| 35 | (DMSO-d6) δ 9.59 (s, 1H), 7.99 (s, 1H), 7.89-7.72 (m, 1H), 7.70-7.42 (m, 3H), 7.42-7.30 (m, 1H), 7.27 (d, J = 1.7 Hz, 1H), 7.24-7.08 (m, 2H), 6.99 (dd, J = 13.2, 1.7 Hz, 1H), 6.61 (dd, J = 7.5, 2.1 Hz, 1H), 5.50-5.37 (m, 1H), 5.14-5.03 (m, 1H), 3.79 (s, 3H), 2.13-2.02 (m, 1H), 1.69 (s, 3H), 1.09 (dt, J = 9.4, 3.2 Hz, 2H), 0.87 (qd, J = 4.7, 2.5 Hz, 2H). | 541.4 |
| 36 | (DMSO-d6) δ 9.48 (s, 1H), 7.99 (s, 1H), 7.90-7.74 (m, 1H), 7.69-7.55 (m, 2H), 7.51-7.42 (m, 1H), 7.42-7.31 (m, 1H), 7.26 (d, J = 1.6 Hz, 1H), 7.23-7.05 (m, 2H), 7.03-6.95 (m, 1H), 6.61 (dd, J = 7.5, 2.0 Hz, 1H), 5.57-5.43 (m, 1H), 5.16-5.04 (m, 1H), 3.92 (q, J = 7.1 Hz, 2H), 3.79 (s, 3H), 2.32-2.19 (m, 4H), 2.13-2.02 (m, 1H), 1.13-1.08 (m, 2H), 1.05 (t, J = 7.1 Hz, 3H), 0.92-0.82 (m, 2H). | 627.2 |
| 37 | (DMSO-d6) δ 9.49 (s, 1H), 7.98 (s, 1H), 7.87-7.73 (m, 1H), 7.68-7.54 (m, 2H), 7.51-7.31 (m, 2H), 7.25 (d, J = 1.6 Hz, 1H), 7.19-7.10 (m, 2H), 6.99 (dd, J = 13.2, 1.7 Hz, 1H), 6.60 (dd, J = 7.5, 2.1 Hz, 1H), 5.50-5.37 (m, 1H), 5.16-5.03 (m, 1H), 3.79 (s, 3H), 2.12-2.01 (m, 1H), 1.94 (t, J = 7.5 Hz, 2H), 1.34-0.89 (m, 16H), 0.91-0.80 (m, 5H). | 653.2 |
| 38 | (DMSO-d6) δ 10.52 (s, 1H), 8.40-8.27 (m, 2H), 8.12 (s, 1H), 7.98-7.88 (m, 1H), 7.82-7.67 (m, 2H), 7.65-7.52 (m, 1H), 7.41 (d, J = 7.4 Hz, 1H), 7.29 (s, 1H), 7.01 (dd, J = 13.2, 1.6 Hz, 1H), 6.67 (dd, J = 7.4, 2.0 Hz, 1H), 5.58 (dd, J = 12.4, 4.7 Hz, 1H), 5.20 (d, J = 12.2 Hz, 1H), 3.82 (s, 3H), | 556.1 |

TABLE 4-1-continued

| Ex. No. | ¹H-NMR δ (ppm) | LCMS m/z [M + H]⁺ |
|---|---|---|
| | 3.67-3.47 (m, 2H), 2.14-2.03 (m, 1H), 1.18-1.01 (m, 2H), 0.97-0.82 (m, 2H). | |
| 39 | (DMSO-d6) δ 9.61-9.34 (m, 1H), 8.13-6.82 (m, 11H), 6.61 (dd, J = 7.5, 2.0 Hz, 1H), 5.68-5.50 (m, 2H), 5.15-5.01 (m, 1H), 3.79 (s, 3H), 3.42 (d, J = 6.1 Hz, 2H), 2.13-2.01 (m, 1H), 1.30 (s, 9H), 1.15-1.03 (m, 2H), 0.93-0.79 (m, 2H). | 656.1 |
| 40 | (DMSO-d6) δ 9.57 (s, 1H), 8.03-7.93 (m, 1H), 7.92-7.75 (m, 1H), 7.69-7.54 (m, 2H), 7.46 (d, J = 8.6 Hz, 1H), 7.42-7.30 (m, 1H), 7.27 (d, J = 1.7 Hz, 1H), 7.23-7.05 (m, 2H), 7.03-6.92 (m, 1H), 6.61 (dd, J = 7.4, 2.1 Hz, 1H), 5.56-5.43 (m, 1H), 5.17-5.05 (m, 1H), 3.79 (s, 3H), 2.13-2.01 (m, 1H), 1.33-1.20 (m, 1H), 1.15-1.03 (m, 2H), 0.92-0.78 (m, 2H), 0.70-0.56 (m, 2H), 0.56-0.42 (m, 2H). | 567.5 |
| 41 | (DMSO-d6) δ 9.56 (s, 1H), 7.98 (s, 1H), 7.86-7.74 (m, 1H), 7.70-7.54 (m, 2H), 7.52-7.43 (m, 1H), 7.42-7.30 (m, 1H), 7.26 (d, J = 1.7 Hz, 1H), 7.22-7.06 (m, 2H), 7.00 (dd, J = 13.2, 1.7 Hz, 1H), 6.61 (dd, J = 7.5, 2.0 Hz, 1H), 5.53-5.39 (m, 1H), 5.12-5.01 (m, 1H), 3.79 (s, 3H), 2.13-2.01 (m, 1H), 1.90-1.79 (m, 2H), 1.71-1.56 (m, 1H), 1.15-1.03 (m, 2H), 0.92-0.78 (m, 2H), 0.64 (dd, J = 6.7, 3.8 Hz, 6H). | 583.5 |
| 42 | (DMSO-d6) δ 9.55 (s, 1H), 7.99 (s, 1H), 7.92-7.81 (m, 1H), 7.71-7.55 (m, 2H), 7.50-7.43 (m, 1H), 7.40-7.30 (m, 1H), 7.27 (d, J = 1.6 Hz, 1H), 7.25-7.04 (m, 2H), 7.00 (dd, J = 13.2, 1.7 Hz, 1H), 6.61 (dd, J = 7.4, 2.0 Hz, 1H), 5.68-5.60 (m, 1H), 5.24-5.11 (m, 1H), 4.34 (s, 2H), 3.79 (s, 3H), 2.14-2.02 (m, 1H), 1.95 (s, 3H), 1.15-1.05 (m, 2H), 0.92-0.82 (m, 2H). | 599.5 |
| 43 | (DMSO-d6) δ 9.57 (s, 1H), 8.00-7.72 (m, 2H), 7.70-7.61 (m, 1H), 7.57 (s, 1H), 7.51-7.44 (m, 1H), 7.39-7.24 (m, 2H), 7.23-7.04 (m, 2H), 7.00 (dd, J = 13.2, 1.7 Hz, 1H), 6.59 (dd, J = 7.4, 2.0 Hz, 1H), 5.83-5.69 (m, 1H), 5.36-5.25 (m, 1H), 4.07 (q, J = 7.1 Hz, 2H), 3.83-3.75 (m, 3H), 2.13-1.97 (m, 1H), 1.17-1.05 (m, 5H), 0.91-0.81 (m, 2H). | 599.1 |
| 44 | (DMSO-d6) δ9.58 (s, 1H), 8.02-7.74 (m, 3H), 7.72-7.57 (m, 3H), 7.57-7.39 (m, 4H), 7.38-7.25 (m, 2H), 7.26-7.18 (m, 1H), 7.13 (s, 1H), 7.06-6.93 (m, 1H), 6.56 (dd, J = 7.4, 2.0 Hz, 1H), 5.76-5.61 (m, 1H), 5.39-5.29 (m, 1H), 3.87-3.65 (m, 3H), 2.13-2.00 (m, 1H), 1.15-1.04 (m, 2H), 0.93-0.81 (m, 2H). | 603.1 |
| 45 | (DMSO-d6) δ 9.58 (s, 1H), 8.69-8.54 (m, 2H), 7.94 (s, 1H), 7.91-7.61 (m, 2H), 7.61-7.40 (m, 5H), 7.26-7.17 (m, 1H), 7.17-7.12 (m, 2H), 6.96 (d, J = 13.1 Hz, 1H), 6.55 (dd, J = 7.5, 2.0 Hz, 1H), 5.79-5.65 (m, 1H), 5.47-5.36 (m, 1H), 3.76 (s, 3H), 2.11-1.99 (m, 1H), 1.14-1.04 (m, 2H), 0.90-0.81 (m, 2H). | 604.0 |
| 46 | (DMSO-d6) δ 9.56 (s, 1H), 7.95 (s, 1H), 7.82-7.71 (m, 2H), 7.68-7.53 (m, 1H), 7.52-7.34 (m, 2H), 7.28 (d, J = 1.6 Hz, 1H), 7.19-7.06 (m, 2H), 7.01 (dd, J = 13.2, 1.6 Hz, 1H), 6.64 (dd, J = 7.4, 2.0 Hz, 1H), 5.53-5.39 (m, 1H), 4.98-4.88 (m, 1H), 3.79 (s, 3H), 2.13-2.02 (m, 1H), 1.83-1.67 (m, 3H), 1.60-1.36 (m, 12H), 1.15-1.05 (m, 2H), 0.91-0.82 (m, 2H). | 661.1 |
| 47 | (DMSO-d6) δ 9.54 (s, 1H), 8.01-7.92 (m, 1H), 7.86-7.74 (m, 1H), 7.71-7.34 (m, 4H), 7.28 (d, J = 1.7 Hz, 1H), 7.19-6.89 (m, 3H), 6.63 (d, J = 7.5 Hz, 1H), 5.62-5.47 (m, 1H), 5.02-4.88 (m, 1H), 3.80 (s, 3H), 2.13-2.02 (m, 1H), 1.11-1.07 (m, 2H), 0.89-0.86 (m, 2H), 0.86-0.79 (m, 9H). | 582.8 |
| 48 | (DMSO-d6) δ 9.59 (s, 1H), 7.98 (s, 1H), 7.90-7.69 (m, 1H), 7.70-7.44 (m, 3H), 7.44-7.30 (m, 1H), 7.30-7.23 (m, 1H), 7.24-7.09 (m, 2H), 7.00 (dd, J = 13.2, 1.7 Hz, 1H), 6.62 (dd, J = 7.4, 2.0 Hz, 1H), 5.64-5.43 (m, 1H), 5.27-5.10 (m, 1H), 3.79 (s, 3H), 3.71 (s, 2H), 3.04 (s, 3H), 2.13-2.01 (m, 1H), 1.16-1.04 (m, 2H), 0.93-0.80 (m, 2H). | 571.6 |
| 49 | (DMSO-d6) δ 9.58 (s, 1H), 8.00-7.89 (m, 1H), 7.90-7.73 (m, 1H), 7.70-7.53 (m, 2H), | 584.4 |

TABLE 4-1-continued

| Ex. No. | ¹H-NMR δ (ppm) | LCMS m/z [M + H]⁺ |
|---|---|---|
|  | 7.53-7.40 (m, 1H), 7.44-7.31 (m, 1H), 7.30-7.23 (m, 1H), 7.23-7.08 (m, 2H), 7.00 (dd, J = 13.2, 1.7 Hz, 1H), 6.62 (dd, J = 7.4, 2.0 Hz, 1H), 5.57-5.41 (m, 1H), 5.19-5.07 (m, 1H), 3.79 (s, 3H), 2.89 (s, 2H), 2.12-2.04 (m, 1H), 2.02 (s, 6H), 1.16-1.03 (m, 2H), 0.92-0.79 (m, 2H). |  |
| 50 | (DMSO-d6) δ 9.59 (s, 1H), 7.99 (s, 1H), 7.91-7.73 (m, 1H), 7.70-7.55 (m, 2H), 7.53-7.43 (m, 1H), 7.42-7.30 (m, 1H), 7.26 (d, J = 1.6 Hz, 1H), 7.22-7.13 (m, 2H), 7.00 (dd, J = 13.2, 1.7 Hz, 1H), 6.62 (dd, J = 7.4, 2.0 Hz, 1H), 5.61-5.46 (m, 1H), 5.25-5.12 (m, 1H), 3.85-3.75 (m, 5H), 3.30-3.23 (m, 4H), 3.14 (s, 3H), 2.13-2.01 (m, 1H), 1.15-1.03 (m, 2H), 0.91-0.79 (m, 2H). | 615.1 |

TABLE 4-2

| Ex. No. | ¹H-NMR δ (ppm) | LCMS m/z [M + H]⁺ |
|---|---|---|
| 51 | (DMSO-d6) δ 9.57 (s, 1H), 7.98 (s, 1H), 7.91-7.72 (m, 1H), 7.70-7.53 (m, 2H), 7.54-7.43 (m, 1H), 7.43-7.31 (m, 1H), 7.27 (d, J = 1.6 Hz, 1H), 7.24-7.06 (m, 2H), 6.99 (dd, J = 13.2, 1.7 Hz, 1H), 6.61 (dd, J = 7.4, 2.0 Hz, 1H), 5.65-5.35 (m, 1H), 5.23-5.01 (m, 1H), 3.79 (s, 3H), 2.39-2.30 (m, 2H), 2.30-2.23 (m, 2H), 2.15-2.00 (m, 1H), 1.89 (s, 3H), 1.17-1.02 (m, 1H), 0.94-0.78 (m, 2H). | 601.5 |
| 52 | (DMSO-d6) δ 9.59 (s, 1H), 7.99 (s, 1H), 7.91-7.74 (m, 1H), 7.69-7.56 (m, 1H), 7.54-7.43 (m, 1H), 7.41-7.20 (m, 2H), 7.19-7.10 (m, 5H), 7.04-6.89 (m, 4H), 6.60 (dd, J = 7.5, 2.0 Hz, 1H), 5.58-5.44 (m, 1H), 5.20-5.08 (m, 1H), 3.79 (s, 3H), 3.36-3.27 (m, 2H), 2.14-2.02 (m, 1H), 1.18-1.04 (m, 2H), 0.92-0.83 (m, 2H). | 617.0 |
| 53 | (DMSO-d6) δ 9.56 (s, 1H), 7.98 (s, 1H), 7.87-7.74 (m, 2H), 7.67-7.55 (m, 1H), 7.53-7.42 (m, 1H), 7.42-7.30 (m, 1H), 7.29-7.23 (m, 1H), 7.23-7.05 (m, 2H), 7.00 (dd, J = 13.2, 1.7 Hz, 1H), 6.61 (dd, J = 7.4, 2.0 Hz, 1H), 5.52-5.38 (m, 1H), 5.14-5.01 (m, 1H), 3.79 (s, 3H), 2.13-2.01 (m, 1H), 1.83 (d, J = 6.7 Hz, 2H), 1.50-1.43 (m, 3H), 1.40-1.18 (m, 4H), 1.13-1.06 (m, 2H), 1.06-0.95 (m, 2H), 0.93-0.81 (m, 2H), 0.68-0.57 (m, 2H). | 623.5 |
| 54 | (DMSO-d6) δ 9.56 (s, 1H), 7.99 (s, 1H), 7.91-7.80 (m, 1H), 7.68-7.55 (m, 1H), 7.52-7.43 (m, 2H), 7.40-7.22 (m, 2H), 7.24-7.05 (m, 2H), 7.00 (dd, J = 13.2, 1.7 Hz, 1H), 6.60 (dd, J = 7.5, 2.0 Hz, 1H), 5.67-5.58 (m, 1H), 5.19-5.07 (m, 1H), 3.94 (q, J = 7.1 Hz, 2H), 3.79 (s, 3H), 3.26-3.13 (m, 2H), 2.13-2.02 (m, 1H), 1.13-1.06 (m, 2H), 1.04 (t, J = 7.1 Hz, 3H), 0.92-0.83 (m, 2H). | 613.4 |
| 55 | (DMSO-d6) δ 9.57 (s, 1H), 7.98 (s, 1H), 7.88-7.73 (m, 1H), 7.70-7.53 (m, 2H), 7.52-7.31 (m, 2H), 7.30-7.24 (m, 1H), 7.23-7.06 (m, 2H), 6.99 (dd, J = 13.2, 1.7 Hz, 1H), 6.61 (dd, J = 7.5, 2.0 Hz, 1H), 5.53-5.39 (m, 1H), 5.16-5.04 (m, 1H), 3.79 (s, 3H), 2.12-2.02 (m, 1H), 1.98 (q, J = 7.5 Hz, 2H), 1.15-1.01 (m, 2H), 0.92-0.76 (m, 2H), 0.73 (t, J = 7.5 Hz, 3H). | 555.0 |
| 56 | (DMSO-d6) δ 9.57 (s, 1H), 7.98 (s, 1H), 7.87-7.74 (m, 1H), 7.70-7.53 (m, 2H), 7.53-7.43 (m, 1H), 7.43-7.30 (m, 1H), 7.29-7.24 (m, 1H), 7.13 (s, 2H), 6.99 (dd, J = 13.1, 1.6 Hz, 1H), 6.61 (dd, J = 7.4, 2.0 Hz, 1H), 5.52-5.38 (m, 1H), 5.14-5.02 (m, 1H), 3.79 (s, 3H), 2.13-2.02 (m, 1H), 1.93 (t, J = 7.3 Hz, 2H), 1.29-1.15 (m, 2H), 1.15-0.99 (m, 2H), 0.91-0.82 (m, 2H), 0.62 (t, J = 7.4 Hz, 3H). | 569.0 |
| 57 | (DMSO-d6) δ 9.57 (s, 1H), 7.98 (s, 1H), 7.87-7.74 (m, 1H), 7.71-7.54 (m, 2H), 7.53-7.42 (m, 1H), 7.42-7.30 (m, 1H), 7.29-7.24 (m, 1H), 7.23-7.06 (m, 2H), 6.99 (dd, J = 13.2, 1.7 Hz, 1H), 6.61 (dd, J = 7.4, 2.0 Hz, 1H), 5.51-5.38 (m, 1H), 5.15-5.03 (m, 1H), 3.79 (s, 3H), 2.13-2.01 (m, 1H), 1.94 (t, J = 7.5 Hz, 2H), 1.22-1.06 (m, 4H), 1.05-0.94 (m, 2H), 0.91-0.82 (m, 2H), 0.69 (t, J = 7.3 Hz, 3H). | 583.5 |
| 58 | (DMSO-d6) δ 9.57 (s, 1H), 7.98 (s, 1H), 7.87-7.73 (m, 1H), 7.67-7.54 (m, 2H), 7.51-7.31 (m, 2H), 7.29-7.23 (m, 1H), 7.23-7.06 (m, 2H), 6.99 (dd, J = 13.1, 1.7 Hz, 1H), 6.60 (dd, J = 7.5, 2.0 Hz, 1H), 5.51-5.37 (m, 1H), 5.16-5.03 (m, 1H), 3.79 (s, 3H), 2.13-1.96 (m, 1H), 1.94 (t, J = 7.5 Hz, 2H), 1.26-0.82 (m, 10H), 0.78-0.68 (m, 3H). | 597.1 |
| 59 | (DMSO-d6) δ 9.57 (s, 1H), 7.98 (s, 1H), 7.89-7.71 (m, 1H), 7.69-7.53 (m, 2H), 7.53-7.42 (m, 1H), 7.42-7.30 (m, 1H), 7.29-7.23 (m, 1H), 7.23-7.06 (m, 2H), 6.99 (dd, J = 13.2, 1.7 Hz, 1H), 6.60 (dd, J = 7.5, 2.0 Hz, 1H), 5.53-5.36 (m, 1H), 5.18-5.01 (m, 1H), 3.79 (s, 3H), 2.12-2.02 (m, 1H), 1.94 (t, J = 7.5 Hz, 2H), 1.21-0.92 (m, 10H), 0.91-0.83 (m, 2H), 0.83-0.72 (m, 3H). | 611.5 |
| 60 | (DMSO-d6) δ 9.57 (s, 1H), 7.98 (s, 1H), 7.87-7.73 (m, 1H), 7.67-7.54 (m, 2H), 7.51-7.31 (m, 2H), 7.28-7.23 (m, 1H), 7.22-7.05 (m, 2H), 6.99 (dd, J = 13.2, 1.7 Hz, 1H), 6.60 (dd, J = 7.5, 2.1 Hz, 1H), 5.51-5.37 (m, 1H), 5.16-5.03 (m, 1H), 3.79 (s, 3H), 2.12-1.98 (m, 1H), 1.94 (t, J = 7.5 Hz, 2H), 1.32-0.90 (m, 14H), 0.90-0.79 (m, 5H). | 639.5 |
| 61 | (DMSO-d6) δ 9.55 (s, 1H), 7.98 (s, 1H), 7.88-7.75 (m, 1H), 7.67-7.54 (m, 2H), 7.50-7.33 (m, 2H), 7.30-7.25 (m, 1H), 7.21-7.04 (m, 2H), 7.00 (dd, J = 13.2, 1.7 Hz, 1H), 6.62 (dd, J = 7.5, 2.0 Hz, 1H), 5.58-5.43 (m, 1H), 5.09-4.98 (m, 1H), 3.79 (s, 3H), 2.25-2.13 (m, 1H), 2.13-2.02 (m, 1H), 1.16-1.01 (m, 2H), 0.90-0.84 (m, 2H), 0.79 (d, J = 6.7 Hz, 6H). | 569.4 |
| 62 | (DMSO-d6) δ 9.58-9.31 (m, 1H), 8.03-7.74 (m, 2H), 7.72-7.44 (m, 3H), 7.42-7.31 (m, 1H), 7.30-7.23 (m, 1H), 7.23-6.87 (m, 4H), 6.60 (d, J = 7.3 Hz, 1H), 5.70-5.50 (m, 1H), 5.06-4.82 (m, 1H), 3.84-3.72 (m, 4H), 2.12-2.02 (m, 1H), 1.28 (s, 9H), 1.14-1.03 (m, 2H), 1.00-0.82 (m, 5H). | 670.2 |
| 63 | (DMSO-d6) δ 10.10 (s, 1H), 8.35-8.14 (m, 3H), 8.09-7.99 (m, 1H), 7.95-7.83 (m, 1H), 7.81-7.49 (m, 4H), 7.48-7.35 (m, 1H), 7.30 (dd, J = 2.7, 1.6 Hz, 1H), 7.07-6.97 (m, 1H), 6.71-6.61 (m, 1H), 5.69-5.53 (m, 1H), 5.34-5.15 (m, 1H), 3.83-3.80 (m, 4H), 2.13-2.03 (m, 1H), 1.16-1.04 (m, 5H), 0.91-0.84 (m, 2H). | 570.4 |
| 64 | (DMSO-d6) δ 9.61-9.36 (m, 1H), 8.00-7.74 (m, 2H), 7.73-7.61 (m, 1H), 7.58-7.31 (m, 3H), 7.30-6.89 (m, 10H), 6.60 (d, J = 7.2 Hz, 1H), 5.75-5.60 (m, 1H), 5.08-4.88 (m, 1H), 4.00-3.86 (m, 1H), 3.83-3.73 (m, 3H), 2.66-2.53 (m, 2H), 2.11-2.01 (m, 1H), 1.26-0.95 (m, 11H), 0.90-0.80 (m, 2H). | 746.4 |
| 65 | (DMSO-d6) δ 10.14 (s, 1H), 8.51-8.17 (m, 3H), 8.08-7.87 (m, 2H), 7.81-7.47 (m, 3H), 7.45-7.38 (m, 1H), 7.26 (dd, J = 11.5, 1.6 Hz, 1H), 7.20-6.86 (m, 7H), 6.68-6.57 (m, 1H), 5.84-5.64 (m, | 646.4 |

TABLE 4-2-continued

| | | |
|---|---|---|
| | 1H), 5.32-5.05 (m, 1H), 3.80-4.20 (m, 4H), 2.97-2.76 (m, 2H), 2.11-2.02 (m, 1H), 1.13-1.08 (m, 2H), 0.90-0.80 (m, 2H). | |
| 66 | (DMSO-d6) δ 10.41-9.51 (m, 2H), 8.89-8.60 (m, 1H), 8.04 (t, J = 6.4 Hz, 1H), 7.96-7.50 (m, 5H), 7.42 (dd, J = 7.3, 3.5 Hz, 1H), 7.33-7.26 (m, 1H), 7.07-6.97 (m, 1H), 6.73-6.62 (m, 1H), 5.75-5.57 (m, 1H), 5.38-5.18 (m, 1H), 4.23-4.14 (m, 1H), 3.82 (s, 3H), 3.14-2.99 (m, 2H), 2.13-2.04 (m, 1H), 2.04-1.91 (m, 1H), 1.83-1.59 (m, 3H), 1.15-1.08 (m, 2H), 0.92-0.84 (m, 2H). | 596.7 |

TABLE 4-3

| | | |
|---|---|---|
| 67 | (DMSO-d6) δ 9.62-9.36 (m, 1H), 7.97 (s, 1H), 7.86-7.73 (m, 1H), 7.67-7.57 (m, 1H), 7.56 (s, 1H), 7.51-7.32 (m, 1H), 7.27 (d, J = 1.6 Hz, 1H), 7.21-6.91 (m, 3H), 6.62 (dd, J = 7.4, 2.0 Hz, 1H), 5.53-5.40 (m, 1H), 5.15-5.02 (m, 1H), 3.83-3.75 (m, 3H), 3.72-3.57 (m, 2H), 2.65-2.55 (m, 2H), 2.20-2.02 (m, 1H), 1.51-1.39 (m, 1H), 1.34 (s, 9H), 1.15-1.00 (m, 4H), 0.91-0.83 (m, 2H). | 710.4 |
| 68 | (DMSO-d6) δ 10.37-9.50 (m, 1H), 8.86-8.60 (m, 1H), 8.57-8.33 (m, 1H), 8.11-7.98 (m, 1H), 7.89-7.74 (m, 2H), 7.73-7.61 (m, 2H), 7.60-7.49 (m, 1H), 7.46-7.34 (m, 1H), 7.28 (d, J = 1.5 Hz, 1H), 7.01 (dd, J = 13.2, 1.6 Hz, 1H), 6.66 (d, J = 7.4 Hz, 1H), 5.50-5.38 (m, 1H), 5.22-5.09 (m, 1H), 3.83-3.81 (m, 3H), 3.10-2.99 (m, 2H), 2.81-2.68 (m, 2H), 2.43-2.34 (m, 1H), 2.14-2.02 (m, 1H), 1.77-1.63 (m, 2H), 1.55-1.39 (m, 2H), 1.15-1.06 (m, 2H), 0.92-0.83 (m, 2H). | 610.3 |
| 69 | (DMSO-d6) δ 9.57-9.32 (m, 1H), 8.04-7.74 (m, 2H), 7.72-7.42 (m, 3H), 7.41-7.30 (m, 1H), 7.29-7.24 (m, 1H), 7.22-6.87 (m, 4H), 6.64-6.56 (m, 1H), 5.80-5.48 (m, 1H), 5.07-4.81 (m, 1H), 3.86-3.72 (m, 4H), 2.11-2.03 (m, 1H), 1.28 (s, 9H), 1.14-1.02 (m, 2H), 1.01-0.83 (m, 5H). | 670.4 |
| 70 | (DMSO-d6) δ 10.52-9.49 (m, 1H), 8.43-8.14 (m, 3H), 8.05 (s, 1H), 7.96-7.85 (m, 1H), 7.83-7.50 (m, 4H), 7.49-7.37 (m, 1H), 7.34-7.27 (m, 1H), 6.98-7.07 (m, 1H), 6.66 (d, J = 7.4 Hz, 1H), 5.68-5.54 (m, 1H), 5.33-5.14 (m, 1H), 3.90-3.80 (m, 4H), 2.14-2.03 (m, 1H), 1.20-1.06 (m, 5H), 0.93-0.83 (m, 2H). | 570.4 |
| 71 | (DMSO-d6) δ 9.60 (s, 1H), 8.02-7.94 (m, 1H), 7.90-7.32 (m, 5H), 7.29-7.24 (m, 1H), 7.23-7.14 (m, 2H), 7.00 (dd, J = 13.2, 1.7 Hz, 1H), 6.62 (dd, J = 7.5, 2.0 Hz, 1H), 5.60-5.45 (m, 1H), 5.24-5.12 (m, 1H), 3.79 (s, 3H), 3.74 (s, 2H), 3.25-3.07 (m, 2H), 2.13-2.01 (m, 1H), 1.15-1.05 (m, 2H), 0.94 (t, J = 7.0 Hz, 3H), 0.90-0.82 (m, 2H). | 585.0 |
| 72 | (DMSO-d6) δ 9.62 (s, 1H), 8.02-7.94 (m, 1H), 7.94-7.80 (m, 1H), 7.79-7.32 (m, 5H), 7.33-7.24 (m, 1H), 7.26-7.21 (m, 1H), 7.21-7.11 (m, 2H), 7.01 (dd, J = 13.2, 1.7 Hz, 1H), 6.94-6.85 (m, 1H), 6.70-6.59 (m, 3H), 5.66-5.52 (m, 1H), 5.26-5.14 (m, 1H), 4.47 (s, 2H), 3.78 (s, 3H), 2.14-2.02 (m, 1H), 1.15-1.01 (m, 2H), 0.92-0.82 (m, 2H). | 633.1 |
| 73 | (DMSO-d6) δ 9.57 (s, 1H), 8.01-7.94 (m, 1H), 7.90-7.75 (m, 1H), 7.75-7.32 (m, 4H), 7.31-7.24 (m, 1H), 7.24-7.06 (m, 2H), 7.00 (dd, J = 13.2, 1.7 Hz, 1H), 6.62 (dd, J = 7.4, 1.9 Hz, 1H), 5.69-5.51 (m, 1H), 5.12-4.98 (m, 1H), 4.16-4.07 (m, 1H), 3.80 (s, 3H), 3.66-3.50 (m, 2H), 2.13-2.02 (m, 1H), 1.94-1.80 (m, 1H), 1.67-1.49 (m, 3H), 1.15-1.01 (m, 2H), 0.92-0.79 (m, 2H). | 597.4 |
| 74 | (DMSO-d6) δ 9.58 (s, 1H), 7.99 (s, 1H), 7.89-7.31 (m, 5H), 7.30-7.24 (m, 1H), 7.24-7.04 (m, 2H), 7.00 (dd, J = 13.2, 1.7 Hz, 1H), 6.61 (dd, J = 7.5, 2.0 Hz, 1H), 5.57-5.43 (m, 1H), 5.15-5.02 (m, 1H), 3.79 (s, 3H), 3.28 (t, J = 6.5 Hz, 2H), 3.22 (q, J = 7.0 Hz, 2H), 2.22 (t, J = 6.7 Hz, 2H), 2.13-2.01 (m, 1H), 1.14-1.05 (m, 2H), 0.94 (t, J = 7.0 Hz, 3H), 0.90-0.83 (m, 2H). | 599.4 |

TABLE 4-3-continued

| | | |
|---|---|---|
| 75 | (DMSO-d6) δ 9.61-9.34 (m, 1H), 8.04-7.75 (m, 2H), 7.72-7.44 (m, 3H), 7.42-7.14 (m, 3H), 7.09-6.83 (m, 3H), 6.67-6.55 (m, 1H), 5.71-5.55 (m, 1H), 5.02-4.83 (m, 1H), 3.80 (s, 3H), 3.75-3.66 (m, 1H), 2.12-2.02 (m, 1H), 1.83-1.66 (m, 1H), 1.36-1.23 (m, 9H), 1.14-1.06 (m, 2H), 0.92-0.82 (m, 2H), 0.67-0.47 (m, 6H). | 698.5 |
| 76 | (DMSO-d6) δ 10.53-10.22 (m, 1H), 8.44-8.17 (m, 3H), 8.06 (d, J = 6.7 Hz, 1H), 7.90 (d, J = 7.9 Hz, 1H), 7.81-7.48 (m, 4H), 7.40 (dd, J = 7.4, 2.4 Hz, 1H), 7.34-7.27 (m, 1H), 7.08-6.98 (m, 1H), 6.71-6.63 (m, 1H), 5.78-5.61 (m, 1H), 5.34-5.13 (m, 1H), 3.84-3.78 (m, 4H), 2.14-2.03 (m, 1H), 1.98-1.81 (m, 1H), 1.16-1.06 (m, 2H), 0.92-0.84 (m, 2H), 0.79-0.54 (m, 6H). | 598.3 |
| 77 | (DMSO-d6) δ 10.27-9.94 (m, 1H), 8.96-8.57 (m, 3H), 8.05 (s, 1H), 8.00-7.88 (m, 1H), 7.81-7.52 (m, 4H), 7.42 (dd, J = 7.3, 2.3 Hz, 1H), 7.30-7.26 (m, 1H), 7.06-6.97 (m, 1H), 6.67 (dt, J = 7.5, 2.4 Hz, 1H), 5.80-5.46 (m, 1H), 5.40-5.13 (m, 1H), 4.43-4.29 (m, 1H), 3.82 (s, 3H), 3.09-2.90 (m, 2H), 2.13-2.03 (m, 1H), 1.14-1.06 (m, 2H), 0.91-0.83 (m, 2H). | 595.2 |
| 78 | (DMSO-d6) δ 9.59-9.38 (m, 1H), 7.99 (d, J = 2.5 Hz, 1H), 7.90-7.77 (m, 1H), 7.71-7.60 (m, 1H), 7.58-7.45 (m, 2H), 7.34 (t, J = 7.3 Hz, 1H), 7.29-7.15 (m, 2H), 7.11-6.89 (m, 3H), 6.64-6.56 (m, 1H), 5.69-5.53 (m, 1H), 5.11-4.92 (m, 1H), 4.23-4.13 (m, 1H), 3.80 (s, 3H), 2.45-2.19 (m, 2H), 2.12-2.02 (m, 1H), 1.33-1.21 (m, 18H), 1.15-1.05 (m, 2H), 0.91-0.84 (m, 2H). | 770.4 |
| 79 | (DMSO-d6) δ 13.40-12.52 (m, 1H), 10.54-10.04 (m, 1H), 8.55-8.19 (m, 3H), 8.08 (s, 1H), 7.99-7.87 (m, 1H), 7.82-7.49 (m, 4H), 7.47-7.36 (m, 1H), 7.29 (dd, J = 6.6, 1.5 Hz, 1H), 7.06-6.97 (m, 1H), 6.71-6.58 (m, 1H), 5.81-5.43 (m, 1H), 5.36-4.96 (m, 1H), 3.85-3.81 (m, 4H), 2.79-2.61 (m, 1H), 2.14-2.03 (m, 1H), 1.15-1.08 (m, 2H), 0.92-0.84 (m, 2H). | 614.2 |
| 80 | (DMSO-d6) δ 9.59-9.34 (m, 1H), 8.02-7.75 (m, 2H), 7.73-7.44 (m, 3H), 7.42-7.31 (m, 1H), 7.29-6.87 (m, 5H), 6.68-6.55 (m, 1H), 5.78-5.53 (m, 1H), 5.09-4.79 (m, 1H), 3.85-3.67 (m, 4H), 2.13-2.02 (m, 1H), 1.51-1.34 (m, 1H), 1.34-1.14 (m, 9H), 1.12-0.92 (m, 4H), 0.91-0.83 (m, 2H), 0.76-0.60 (m, 6H). | 712.3 |
| 81 | (DMSO-d6) δ 10.69-10.38 (m, 1H), 8.44-8.18 (m, 3H), 8.08 (d, J = 7.1 Hz, 1H), 8.00-7.90 (m, 1H), 7.82-7.50 (m, 4H), 7.44 (t, J = 7.7 Hz, 1H), 7.30 (t, J = 1.3 Hz, 1H), 7.03 (d, J = 13.2 Hz, 1H), 6.67 (dd, J = 7.5, 2.1 Hz, 1H), 5.76-5.63 (m, 1H), 5.24-5.09 (m, 1H), 3.84-3.82 (m, 4H), 2.14-2.04 (m, 1H), 1.59-1.43 (m, 1H), 1.40-1.29 (m, 1H), 1.28-1.16 (m, 1H), 1.15-1.07 (m, 2H), 0.91-0.83 (m, 2H), 0.75-0.64 (m, 6H). | 612.4 |

TABLE 4-4

| | | |
|---|---|---|
| 82 | (DMSO-d6) δ 9.58 (s, 1H), 8.03-7.73 (m, 2H), 7.71-7.43 (m, 3H), 7.33 (d, J = 7.4 Hz, 1H), 7.28 (d, J = 1.6 Hz, 1H), 7.25-6.96 (m, 3H), 6.62 (dd, J = 7.5, 2.0 Hz, 1H), 5.73-5.60 (m, 1H), 5.26-5.13 (m, 1H), 3.80 (s, 3H), 3.73 (s, 2H), 2.14-2.02 (m, 1H), 1.14-1.06 (m, 2H), 0.93-0.83 (m, 2H). | 566.4 |
| 83 | (DMSO-d6) δ 9.56 (d, J = 7.5 Hz, 1H), 8.03-7.95 (m, 1H), 7.93-7.73 (m, 1H), 7.71-7.60 (m, 1H), 7.57 (s, 1H), 7.47 (d, J = 8.9 Hz, 1H), 7.43-7.32 (m, 1H), 7.28 (d, J = 1.6 Hz, 1H), 7.24-7.06 (m, 1H), 7.05-6.93 (m, 2H), 6.62 (dt, J = 7.5, 2.0 Hz, 1H), 5.70-5.53 (m, 1H), 5.20-5.03 (m, 1H), 4.38-4.25 (m, 1H), 3.97-3.87 (m, 1H), 3.80 (s, 3H), 3.71-3.59 (m, 1H), 2.13-2.02 (m, 1H), 1.21-1.17 (m, 3H), 1.17-1.13 (m, 3H), 1.13-1.07 (m, 2H), 0.91-0.82 (m, 2H). | 627.2 |
| 84 | (DMSO-d6) δ 10.78-10.37 (m, 1H), 8.61-8.17 (m, 1H), 8.15-8.04 (m, 1H), 7.94-7.47 (m, 5H), 7.36 (d, J = 7.4 Hz, 1H), 7.29 (s, 1H), 7.02 (d, J = 13.2 Hz, 1H), 6.70-6.59 (m, 3H), 5.59-5.42 (m, 1H), | 587.2 |

TABLE 4-4-continued 5.13-4.89 (m, 1H), 3.89-3.79 (m, 4H),
3.45-3.26 (m, 2H), 2.13-2.03 (m, 1H), 1.15-1.05 (m,
2H), 0.92-0.84 (m, 2H).

Test Example 1

BTK Activity Inhibition Test
(Preparation of Dephosphorylated BTK)

Dephosphorylated BTK was obtained by adding λ protein phosphatase (manufactured by New England BioLabs Inc., Code No. P0753S) and $MnCl_2$ at 10 U/μg and 2 mM, respectively to biotinylated BTK protein BTN-BTK (Manufactured by Carna Biosciences, Inc.) enzyme solution, reacting the mixture at 4° C. overnight, and removing of λ protein phosphatase by anti DYKDDDDK-tag antibody agarose gel chromatography, followed by buffer exchange using a 10DG Desalting Column.
(Kinase Activity Measuring Method)

The kinase activity was measured using QuickScout Screening Assist (trade mark) MSA (commercially available kit manufactured by Carna Biosciences, Inc.) by mobility shift assay (MSA) method. The substrate of the kinase reaction was an FITC-labeled SRCtide peptide included in the kit. An assay buffer [20 mM HEPES, 0.01% Triton X-100 (Trade mark), 2 mM dithiothreitol, pH7.5] was used and adjusted at 4 μM substrate, 20 mM $MgCl_2$ and 200 μm ATP to obtain a substrate mixture solution. The enzyme solution was also prepared by diluting the dephosphorylated BTK to 0.6 nM using the assay buffer. The 10 mM solution of the test compound in DMSO was further diluted with DMSO to 10 levels of the concentration (0.00003 mM, 0.0001 mM, 0.0003 mM, 0.001 mM, 0.003 mM, 0.01 mM, 0.03 mM, 0.1 mM, 0.3 mM, 1 mM), each of which was subjected to a 25-fold dilution with the assay buffer to obtain the drug solutions (4% DMSO solutions). 5 μL of the drug solution or a control solution (4% DMSO-assay buffer), 5 μL of the substrate mixture solution, and 10 μL of the enzyme solution were mixed in the wells of a polypropylene 384-well plate and allowed to react at room temperature for 1 hour, and then quenched by adding 60 μL of the termination buffer included in the kit. Subsequently, the quantities of the substrates (S) and the phosphorylated substrate (P) in the reaction solution were measured using LabChip EZ Reader II system (manufactured by Caliper Life Sciences) according to the protocol of the assay kit.
(BTK Inhibiting Activity Evaluation Method)

The heights of the peaks of the isolated substrate and the phosphorylated substrate were represented as S and P, respectively, and a blank which contained the assay buffer instead of the enzyme solution was also measured.

The inhibition rate (%) of the test compound was calculated according to the following equation;

$$\text{Inhibition rate (\%)} = (1-(C-A)/(B-A)) \times 100$$

wherein, A, B and C represent P/(P+S) of the blank well, P/(P+S) of the control well and P/(P+S) of the compound-containing well, respectively.

The $IC_{50}$ value was calculated via a regression analysis of the inhibition rate (%) and the test compound concentration (logarithmic value).
(Evaluation Results)

Since the group of the compounds of the Examples showed the $IC_{50}$ values of 10 nM or less against dephosphorylated BTK, Compound (I) of the invention was revealed to have a potent BTK inhibiting effect.

Test Example 2

Intracellular BTK Auto-Phosphorylation Activity Inhibition Test
(Culture of Cells to be Used)

Ramos cells (2G6.4C10, ATCC No. CRL-1923) were cultured in a T75 flask containing RPMI-1640 medium (GIBCO, #A10491-01) supplemented with 10% FBS (AusGene) and 5% penicillin-streptomycin (Nacalai Tesque, Inc.) (hereinafter referred to as growth medium) in a 5% $CO_2$ incubator.
(Addition of the Compound to be Tested)

The cultured Ramos cells were diluted to a cell density of $7.5 \times 10^6$ cells/mL with a serum-free RPMI-1640 (hereinafter referred to as medium) and kept at 37° C. for 45 minutes. The cell suspension was dispensed in 1 mL aliquots into 2.0 mL tubes. The 0.3 mM solution of the test substance in DMSO was diluted with the medium to make a 0.9 μM test compound solution, 500 μL of which was then added to the tubes and the incubation was conducted at 37° C. for 1 hour in the presence of the test compound at a final concentration of 0.3 μM. Thereafter, the anti-IgM antibody (Invitrogen, H15100) which had been diluted with the medium was added at a final concentration of 10 μg/mL, and the incubation was conducted at 37° C. for 10 minutes.
(Extraction of Proteins)

To the pellets obtained by recovering the cells via centrifugation, 100 μL of a lysis buffer [RIPA Buffer(×1) (Cell Signaling Technology, Inc.) supplemented with 1% Phosphatase inhibitor Cacktail 3 (Sigma Corporation, No. P0044), 1% Phosphatase inhibitor Cacktail (Nacalai Tesque, Inc., No. 07575) and 1 mM phenylmethylsulfonyl fluoride (PMSF)] was added and stirred gently and then allowed to stand for 10 minutes. The supernatant was recovered by centrifugation (15,000 rpm, 15 minutes) and the protein level was quantified. The portion was mixed with the SDS-sample buffer, allowed to react for 5 minutes at 95° C. to denature the protein, thereby obtaining a sample solution. Each 5 μL of the sample solutions was applied to each well containing a 4 to 20% gradient acrylamide gel (COSMO BIO Co., Ltd., No. 414879) and electrophoresis was conducted. Thereafter, iBlot gel transfer system (Life Technologies Corporation) was used to transfer the proteins in the gel onto a PVDF membrane.
(Detection of BTK or Phosphorylated BTK)

The PVDF membrane after transfer was blocked with 2% ECL prime blocking Reagent (GE Healthcare) and thereafter the reaction was conducted overnight at 4° C. using anti-BTK mouse antibody (BD transduction laboratory, No. 611116) or anti-phosphorylated BTK rabbit antibody (pY223, EPITOMICS, No. 2207-1) as a primary antibody. The unreacted primary antibody was washed with a TBST buffer (10 mM Tris-HCl (pH7.5), 150 mM NaCl, 0.1% Tween 20) and then the reaction was conducted for 1 hour at room temperature in a TBST buffer supplemented with 2% ECL prime blocking Reagent using HRP-labeled anti-mouse IgG goat antibody (Life Technologies Corporation, No. 62-6520) or anti-rabbit IgG goat antibody (Life Technologies Corporation, No. 65-6120) as a secondary antibody. After washing the unreacted secondary antibody with the TBST buffer, ECL Prime Western Blotting Detection System (GE Healthcare) was used to conduct a reaction in accordance with the attached protocol, and then the respective bands as chemiluminescences were detected with a CCD camera (ATTO, Light-Capture II). The detected bands were subjected to densitometry (ATTO CS Analyzer ver3.0) to be represented as numerical values, and the inhibition rate (%) was calculated based on the intensity of the band in each group, while taking the luminescence of the phosphorylated BTK band in the group without added compound with IgM stimulation as 100% and the luminescence of the phosphorylated BTK band in the group without added compound without IgM stimulation as 0%. Each phosphorylated BTK band was corrected based on the total BTK.

The combinations of the primary antibodies and the secondary antibodies employed in this test and the dilution magnitudes thereof are shown below.

TABLE 5

| | Primary antibody (dilution magnitude) | Secondary antibody (dilution magnitude) |
|---|---|---|
| 1 | Anti-BTK mouse antibody (1/4000) | Anti-mouse IgG goat antibody (1/5000) |
| 2 | Anti-phosphorylated BTK rabbit antibody (1/500) | Anti-rabbit IgG goat antibody (1/5000) |

The results obtained at a test compound concentration of 0.3 µM are shown in Table 6. The intracellular BTK autophosphorylation inhibiting activity was indicated with the mark "*" when 70% or more, with the mark "" when 50% or more and less than 70%, and with the mark "*" when 30% or more and less than 50%.

In this test, the compounds of the present invention inhibited the intracellular BTK autophosphorylation activity potently at a concentration of 0.3 µM as shown in Table 6.

TABLE 6

| Test compound (Example No.) | BTK Phosphorylation inhibiting activity |
|---|---|
| 1 | *** |
| 2 | *** |

The results of Test Example 2 indicate that the compounds of the invention have potent inhibitory effects also on "the intracellular BTK autophosphorylation activity".

Test Example 3

Inhibition Test on the Change of Ramos Intracellular Calcium Ion

The intracellular BTK inhibition by the compounds of the invention was verified by measuring the effects of the compounds of the invention on "anti-IgM antibody BCR stimulation-induced intracellular calcium influx".
(Addition of Cell Suspension and Calcium Indicator)

One day before measurement, the Ramos cells were cultured after suspended again at a cell density of $1.0 \times 10^6$ cells/mL in a fresh growth medium (growth medium as used in Test Example 2), and the cells were recovered next day by centrifugation and washed with RPMI-1640 medium supplemented with 5% penicillin-streptomycin (Nacalai Tesque, Inc.) (Medium 1). These cells were suspended again at a cell density of $2.0 \times 10^6$ cells/mL in RPMI-1640 medium supplemented with 1% Ultra Low IgG FBS (GIBCO, #16250) and 5% penicillin-streptomycin (Nacalai Tesque, Inc.) (Medium 2), and thereafter each 100 µL of the cell suspension was added to each well of a poly lysine-coated microplate (BD BioCoat™, #356692), centrifuged (700 rpm, 3 minutes) and then incubated for 1 hour in a 5% $CO_2$ incubator at 37° C. Each 100 µL of a calcium indicator Fluo-8NW dye-loading solution (AAT Bioquest, #36315) was added to each well, and incubation was continued further for 30 minutes in the 5% $CO_2$ incubator at 37° C.
(Addition of the Compound to be Tested)

A 10 mM stock solution of a test compound in DMSO was further diluted with DMSO to 6 concentrations (1, 0.3, 0.1, 0.03, 0.01, 0.003 mM), and a test compound-free DMSO solution was employed as a control. Then each was subjected to a 47.6-fold dilution with Medium 2 and each 10 µL was added to each well of the aforementioned plate, which was incubated at 37° C. for 10 minutes (final concentrations of the test compound: 1, 0.3, 0.1, 0.03, 0.01, 0.003, and 0 µM).
(Measurement of Calcium Ion Concentration)

Concentration of the Ramos intracellular calcium ion was measured as a fluorescent intensity of the calcium indicator Fluo-8NW using a microplate reader (SynergyH1) (Ex/Em=490/525 nm). After measuring the baseline for 15 seconds, 50 µL of the anti-IgM antibody (Invitrogen, #H15100) diluted with Medium 2 to 10.4 µg/mL was added to each well described above (final concentration of 2.0 µg/mL) to effect BCR stimulation, and then the measurement was continued further for 150 seconds.

FIG. 1 shows the results of the compound of Example 1 as a representative. As shown in FIG. 1, the compound of the invention inhibited "a change of intracellular calcium ion induced by BCR-stimulation" in a concentration-dependent manner from a low concentration, indicating that the BCR signal was inhibited effectively.

Test Example 4

Test of Passive Cutaneous Anaphylaxis Reaction in Mouse

Since BTK plays an important role in FcεRI signal transmission in a mast cell, it was investigated whether a mast cell-involving immediate allergic reaction, namely, passive cutaneous anaphylaxis reaction (PCA reaction), which is an immediate allergic reaction involving mast cell, was inhibited by the administration of the compound.
(Preparation of Test Compound Solution)

DMSO, polyethylene glycol 400 (PEG#400, Nacalai Tesque, Inc. #28215-95), and 30% (w/v) hydroxypropyl-β-cyclodextrin aqueous solution (HP-β-CD, Sigma Corporation, #332607-500) were successively added to the test compound in this order, and mixed thoroughly to prepare a test compound solution (solvent composition: 5% solution of test compound in DMSO, 30% PEG#400, 65% HP-β-CD [30% (w/v) aqueous solution]). In the solvent control group, a DMSO solution was used instead of the solution of the test compound in DMSO.
(PCA Reaction)

An anti DNP-IgE monoclonal antibody (50 µg/mL, Santa Cruz Biotechnology, Inc., #sc-69695) was intradermally administered to both auricles in an ICR mouse under systemic anesthesia (10 µL/site). After 46 hours, the solvent or the solution of a test compound dissolved in a solvent to achieve the test dosage (3.0 mg/mL) was given orally (10 mL/mouse body weight (kg)). After 2 hours, 0.5% Evans Blue dye (Wako Pure Chemical Industries, Ltd., #054-04062)-containing DNP-BSA (1 mg/mL, LSL, #LG-3017) was given intravenously (0.25 mL/mouse) to induce an allergic reaction. After 30 minutes, the animal was euthanized under systemic anesthesia by cervical dislocation and the both auricles were collected. The pair of auricles collected was impregnated with 1M KOH solution (0.7 mL) and allowed to stand overnight at 37° C. to dissolve the auricles. To the suspension thus obtained, 9.3 mL of acetone-0.2M phosphoric acid (13:5) mixture solution was added and the resultant insolubles were removed by centrifugation (3000 rpm, 10 minutes) and 0.2 μm filtration. The absorbance of the resultant filtrate at 620 nm was measured, and used as an index of the dye leakage level. The aforementioned experiment was conducted using 5 mice in each group, the mean value of which then served as a basis for the evaluation of the dye leakage level.

Figure 2:
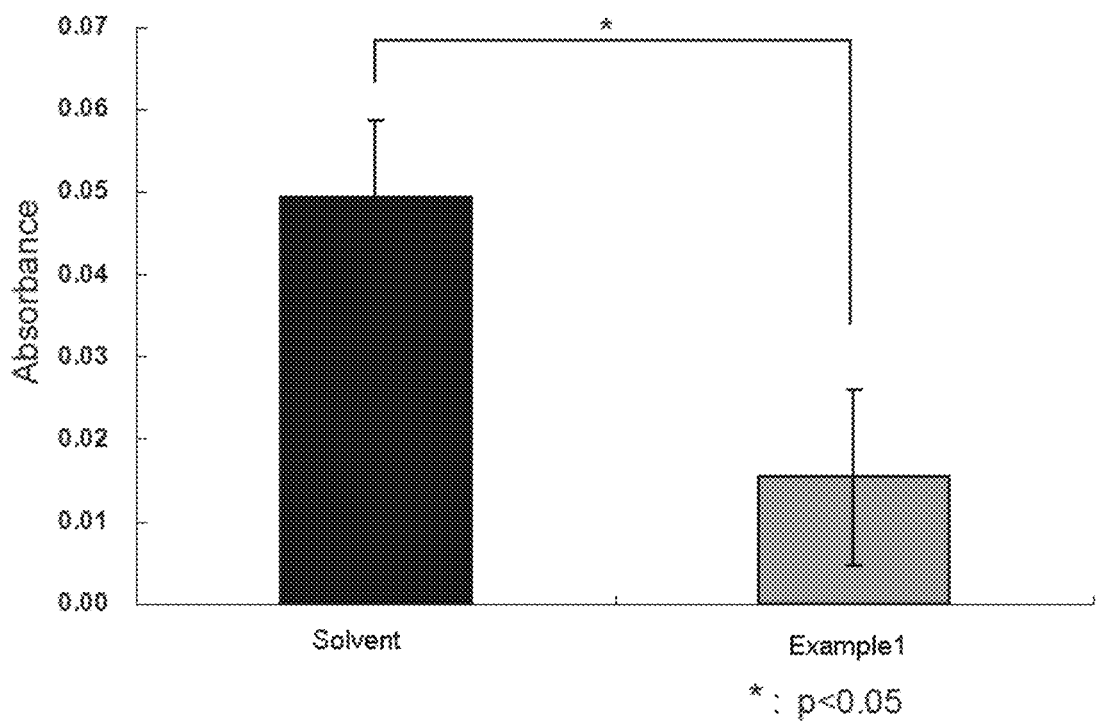
FIG. 2 shows that the compound of Example 1, in the PCA reaction test, inhibited the leakage of the dye in blood into the auricles significantly when compared with the solvent group (Test Example 4).

The results are shown in FIG. 2. As shown in FIG. 2, the compound of Example 1 inhibited the leakage of the dye into the auricles significantly as compared with the solvent group. Thus, the inhibitory effect on the passive cutaneous anaphylaxis reaction (PCA reaction) was confirmed.

Test Example 5

Effect in Mouse Collagen-Induced Arthritis Model

Incomplete Freund's Adjuvant (Chondrex, Inc., #7002) supplemented with *M. Tuberculosis* H37 Ra, Desiccated (Beckton Dickinson and Company, #231141) at 2.5 mg/mL and Bovine Type II Collagen, 2 mg/mL Solution (Chondrex, Inc., #20022) were mixed in a 1:1 ratio to form an emulsion. Three groups of DBA/1J mice (10 animals/group) (6-week old, male) received 0.1 mL per animal of the emulsion which was given in small portions on Day 0 and Day 21 by intradermal injection at the base of the tail, thereby accomplishing the immunization. The solvent or the test compound solution was given twice a day orally every day from Day 18 to Day 36 (test compound doses in the respective groups: 0 mg/kg, 30 mg/kg, 60 mg/kg). The treatment solution was prepared with the similar solvent in the similar manner as Test Example 4.

After the boost on Day 21, the state of the arthritis onset in each extremity was scored visually once in 2 or 3 days according to the criteria shown in Table 7. The scores of all four extremities were summed up on each mouse basis, and the mean value of 10 animals in each group was represented as an arthritis score (normal "0" up to maximum "16").

TABLE 7

| Score | State |
|---|---|
| 0 | Normal |
| 1 | Swelling and/or redness of paw or one finger |
| 2 | Swelling of 2 or more joints |
| 3 | Swelling of entire paw covering more than two joints |
| 4 | Severe arthritis of paw and entire fingers |

Figure 3:
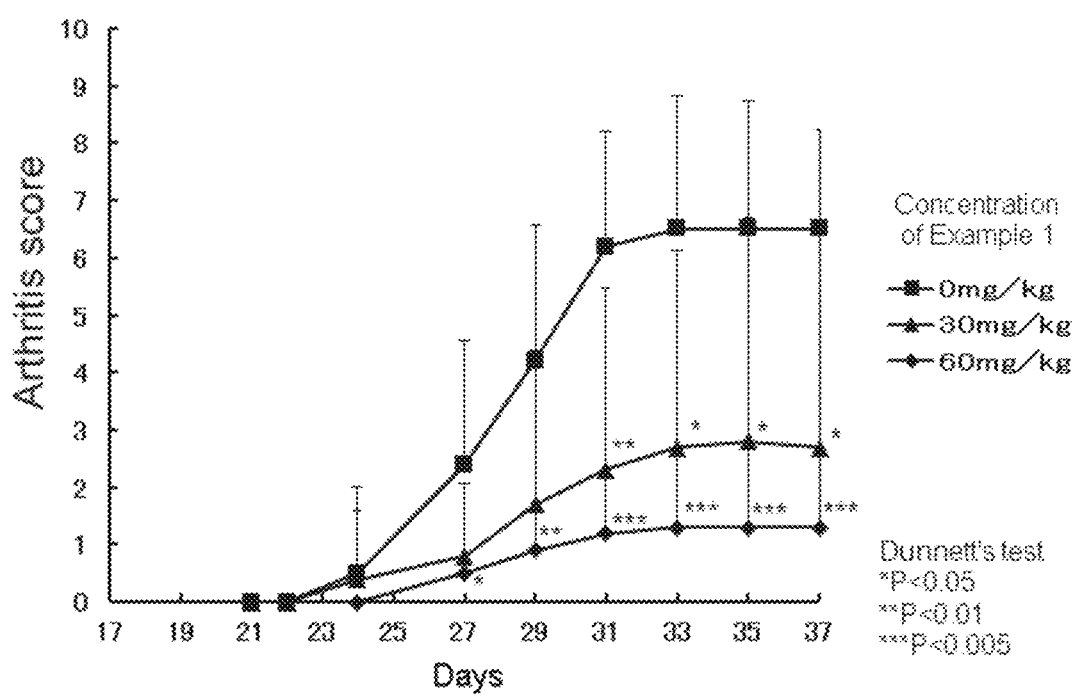
FIG. 3 shows the effect of the compound of Example 1 on the mouse model of collagen-induced arthritis (Test Example 5).

The compound of Example 1 which is a compound of the invention inhibited the onset of the arthritis in a dose dependent manner as shown in FIG. 3. At the same time, it was able to circumvent any toxic signs such as weight loss. Based on these results, the compound of the invention was proven to have an excellent anti-inflammatory effect and also to be highly possible to have an excellent safety.

Test Example 6

Effect in Rat Collagen-Induced Arthritis Model

Incomplete Freund's Adjuvant (Sigma-Aldrich, #F5506) and Bovine Type II Collagen, 4 mg/mL Solution (Sichuan University, Lot.08H0497) were mixed in a 1:1 ratio to form an emulsion. Three groups of Lewis rat (10 animals/group) (5-6 week old, female) received 0.5 mL per animal of the emulsion which was given in small portions on Day 0 and Day 7 by intradermal injection at 3 sites, one site at the base of the tail (0.1 mL), and the rest of two sites (0.2 mL/site) were on the back of the rat near to the base of the tail, thereby accomplishing the immunization. The solvent or the test compound solution was given twice a day orally every day from Day 0 to Day 20 (test compound doses in the respective groups: 0 mg/kg, 30 mg/kg, 60 mg/kg). The treatment solution was prepared with the similar solvent in the similar manner as Test Example 4.

After the boost on Day 7, the state of the arthritis onset in each extremity was scored visually twice in a week according to the criteria shown in Table 8. The scores of all four extremities were summed up on each rat basis, and the mean value of 10 animals in each group was represented as an arthritis score (normal "0" up to maximum "16").

TABLE 8

| Score | State |
|---|---|
| 0 | Normal |
| 1 | Erythema and mild swelling confined to the mid-foot(tarsals) or ankle joint |
| 2 | Erythema and mild swelling extending from the ankle to the mid-foot |
| 3 | Erythema and moderate swelling extending from the ankle to the metatarsal joints |
| 4 | Erythema and severe swelling encompass the ankle, foot, and digits |

Figure 4:
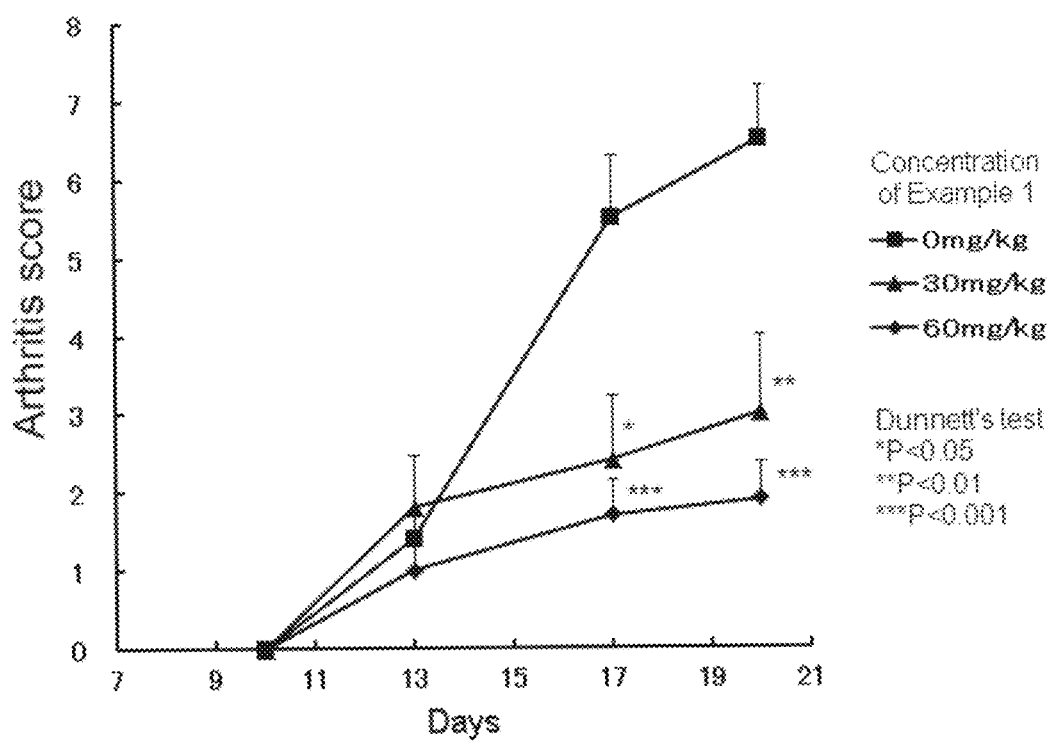
FIG. 4 shows the effect of the compound of Example 1 on the rat model of collagen-induced arthritis (Test Example 6).

The compound of Example 1 which is a compound of the invention inhibited the onset of the arthritis in a dose dependent manner as shown in FIG. 4. At the same time, it was able to circumvent any toxic signs such as weight loss. Based on these results, the compound of the invention was proven to have an excellent anti-inflammatory effect and also to be highly possible to have an excellent safety.

Test Example 7

Blood Plasma Concentration after Oral Administration to Mouse
(Metabolite Verification Test of the Prodrug)

Generally, it is preferable that prodrugs are metabolized to active drugs quickly after oral administration followed by absorption from gastrointestinal tract. Therefore it is investigated whether the compound (I) of the present invention, which is corresponding to prodrug, was metabolized to active form quickly in the body.

An ICR mouse (3 animals/group) (6-week old, male) was received the suspension of a test compound suspended in a solvent (0.5% aqueous methylcellulose solution) to achieve the test dosage (30 mg/kg) by oral administration. After 1 hour, under a systemic anesthesia, blood samples were collected via cardiac puncture using heparin-coated syringe, then the samples were centrifuged (4° C., 10000 rpm, 10 min.) to collect plasma samples. Plasma samples (5 μL) and methanol solution which contains internal standard (495 μL) were transferred to well plate with filter and mixed. Then centrifuged (4° C., 3000 rpm, 3 min.) to remove denatured protein and then the filtrates (extracts) were collected. For the calibration curve, methanol solution of metabolite that contains internal standard was prepared, then mixed with plasma samples of untreated mouse, and then treated in similar manner with well plate with filter. For the calibration curve of prodrug (unchanged drug), standard calibration solution, which mixed methanol solution of prodrug and methanol solution of internal standard, was used.

The concentrations of prodrug and its metabolite, Example compound 1, of the extract were determined by LC/MS (liquid chromatography-mass spectrometry), using standard curves of the peak area ratio of internal standard.

TABLE 9

| Test compound | plasma concentration after po, 1 hour (ng/mL) | |
| --- | --- | --- |
| | Prodrug (unchanged drug) | Metabolite (Example compound 1) |
| Example 35 | ND | 1451 |
| Example 36 | ND | 942 |

ND: Not Detected

As shown in Table 9, the prodrug compounds of the present invention were not observed in the blood after oral administration, but Example compound 1, its corresponding metabolite was observed. Based on these results, the prodrug compounds of the present invention were verified that those compounds were metabolized quickly in the body to active form.

INDUSTRIAL APPLICABILITY

The compound provided by the present invention is useful as a preventive or therapeutic pharmaceutical (pharmaceutical composition) or its prodrug for diseases which are known to be involved in abnormal cell response through BTK, for example, self-immune diseases, inflammatory diseases, bone diseases, and cancers such as lymphoma. The compound is also useful, as a BTK inhibitor, for reagents to be used in tests and researches.

The invention claimed is:

1. A compound of formula (I):

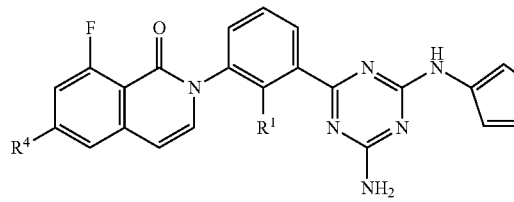

wherein
R$^1$ is a substituted or unsubstituted lower alkyl group,
R$^2$ is a hydrogen atom or a substituted or unsubstituted lower alkyl group,
A is a nitrogen atom or C—R$^3$,
R$^3$ is a hydrogen atom, cyano group, a substituted or unsubstituted acyl group, a substituted or unsubstituted sulfonyl group, or a substituted or unsubstituted carbamoyl group, and
R$^4$ is a substituted or unsubstituted lower alkyl group, a substituted or unsubstituted cycloalkyl group,
or a pharmaceutically acceptable salt thereof.

2. The compound according to claim 1, wherein R$^1$ is —CH$_2$OR$^5$, and
R$^5$ is a substituted or unsubstituted acyl group,
or a pharmaceutically acceptable salt thereof.

3. The compound according to claim 1, wherein R$^1$ is a hydroxymethyl group,
or a pharmaceutically acceptable salt thereof.

4. The compound according to claim 1, wherein R$^4$ is a substituted or unsubstituted cycloalkyl group,
or a pharmaceutically acceptable salt thereof.

5. The compound according to claim 4, wherein R$^4$ is a cyclopropyl group,
or a pharmaceutically acceptable salt thereof.

6. The compound according to claim 1, wherein R$^2$ is a methyl group,
or a pharmaceutically acceptable salt thereof.

7. The compound according to claim 1, wherein R$^2$ is a hydrogen atom,
or a pharmaceutically acceptable salt thereof.

8. The compound according to claim 1, wherein A is a nitrogen atom,
or a pharmaceutically acceptable salt thereof.

9. The compound according to claim 1, wherein A is C—R$^3$,
or a pharmaceutically acceptable salt thereof.

10. A compound selected from the group consisting of:

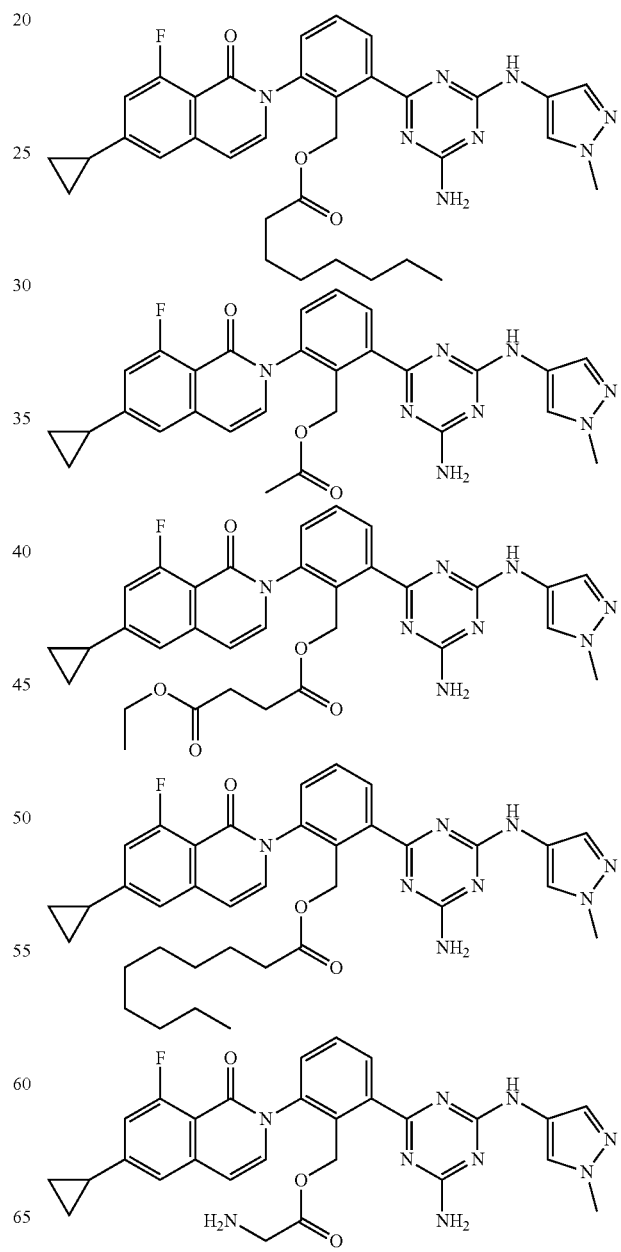

69
-continued
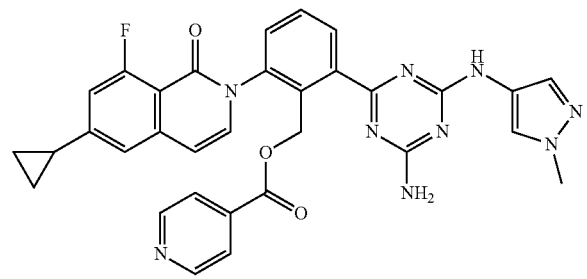
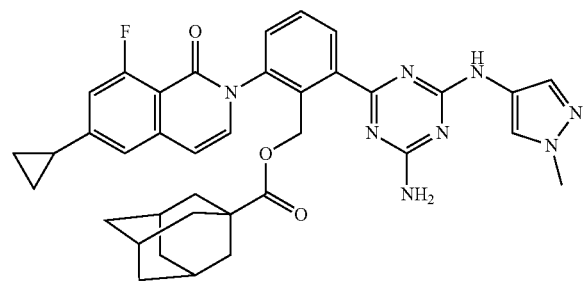
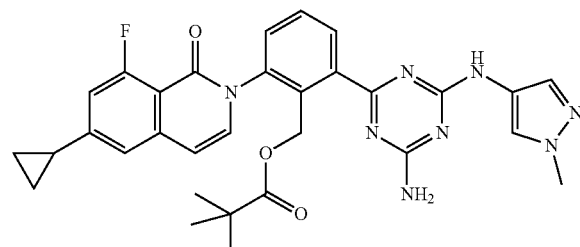
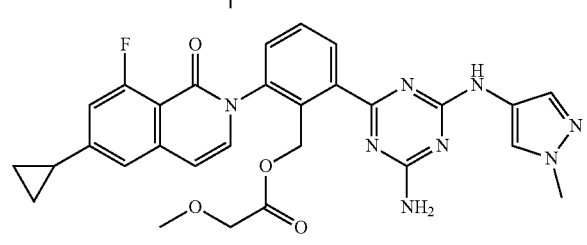
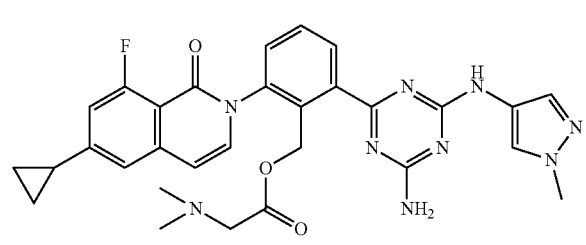 [SMILES: CN(C)CC(=O)OCc1c(-c2nc(N)nc(Nc3cnn(C)c3)n2)cccc1-n1ccc2cc(C3CC3)cc(F)c2c1=O]
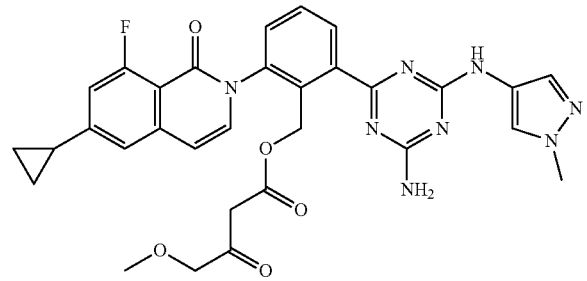 [SMILES: CCOC(=O)CC(=O)OCc1c(-c2nc(N)nc(Nc3cnn(C)c3)n2)cccc1-n1ccc2cc(C3CC3)cc(F)c2c1=O]
70
-continued
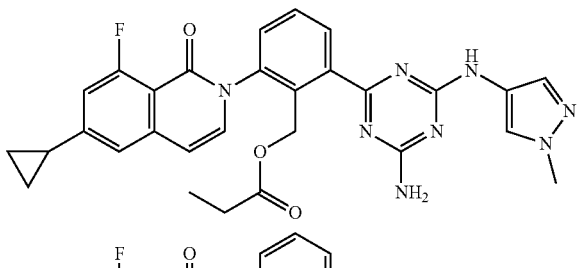
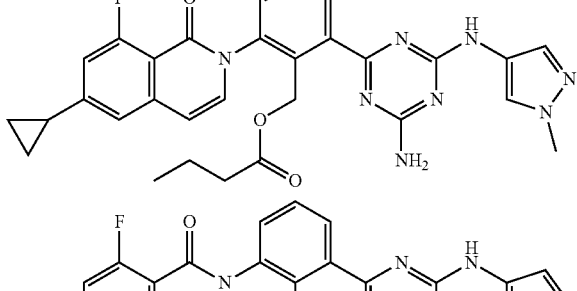
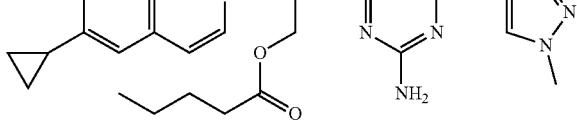
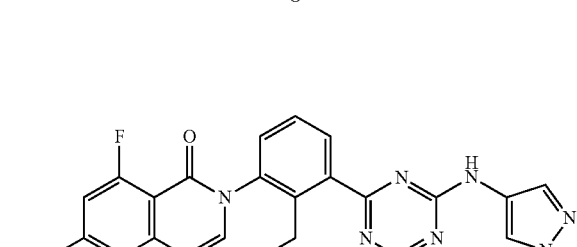
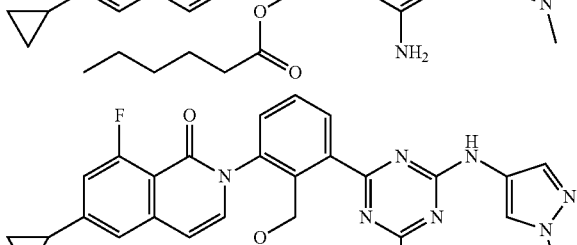
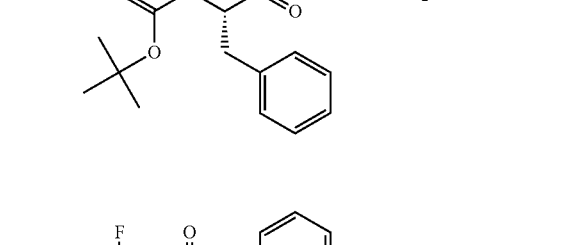
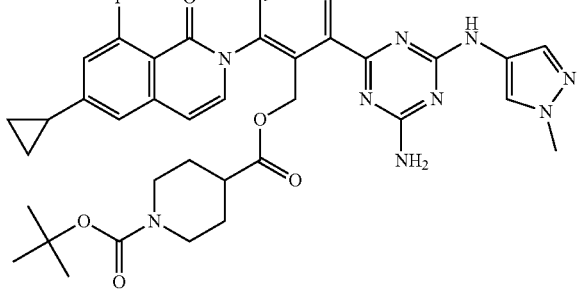

-continued
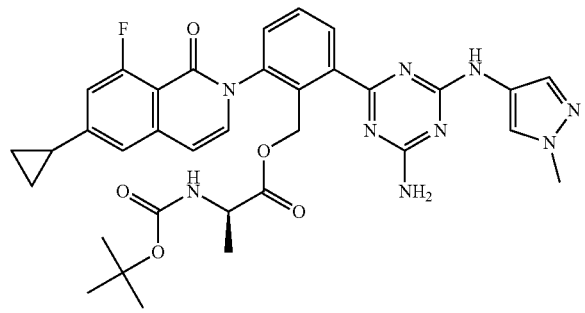 [SMILES: C[C@@H](NC(=O)OC(C)(C)C)C(=O)OCc1c(-c2nc(N)nc(Nc3cnn(C)c3)n2)cccc1-n1ccc2cc(C3CC3)cc(F)c2c1=O]
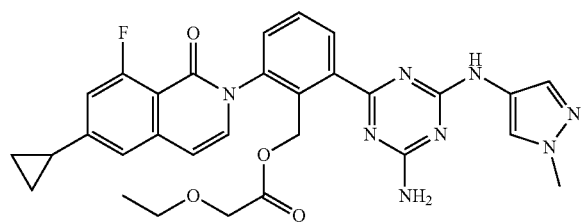 [SMILES: CCOCC(=O)OCc1c(-c2nc(N)nc(Nc3cnn(C)c3)n2)cccc1-n1ccc2cc(C3CC3)cc(F)c2c1=O]
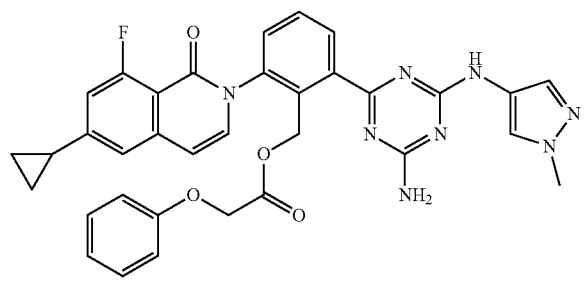 [SMILES: Cn1cc(Nc2nc(N)nc(-c3cccc(-n4ccc5cc(C6CC6)cc(F)c5c4=O)c3COC(=O)COc3ccccc3)n2)cn1]
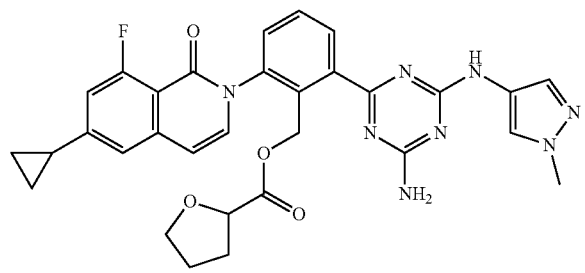 [SMILES: Cn1cc(Nc2nc(N)nc(-c3cccc(-n4ccc5cc(C6CC6)cc(F)c5c4=O)c3COC(=O)C3CCCO3)n2)cn1]
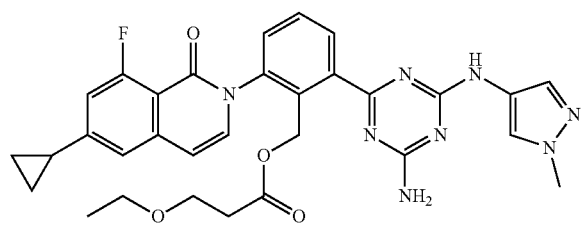 [SMILES: CCOCCC(=O)OCc1c(-c2nc(N)nc(Nc3cnn(C)c3)n2)cccc1-n1ccc2cc(C3CC3)cc(F)c2c1=O]
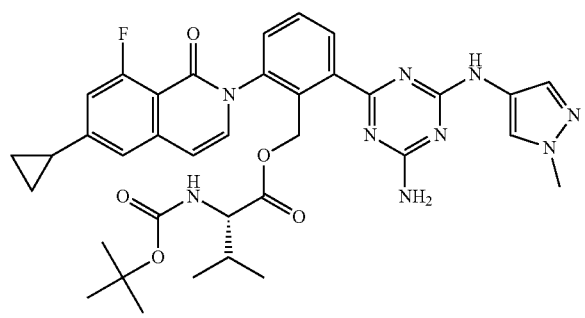 [SMILES: CC(C)[C@H](NC(=O)OC(C)(C)C)C(=O)OCc1c(-c2nc(N)nc(Nc3cnn(C)c3)n2)cccc1-n1ccc2cc(C3CC3)cc(F)c2c1=O]
-continued
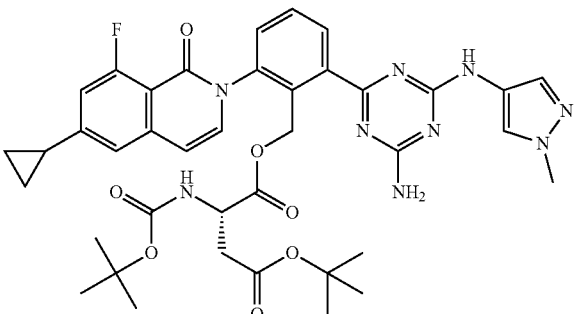 [SMILES: CC(C)C[C@H](NC(=O)OC(C)(C)C)C(=O)OCc1c(-c2nc(N)nc(Nc3cnn(C)c3)n2)cccc1-n1ccc2cc(C3CC3)cc(F)c2c1=O]
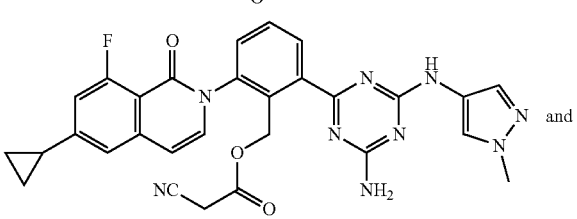
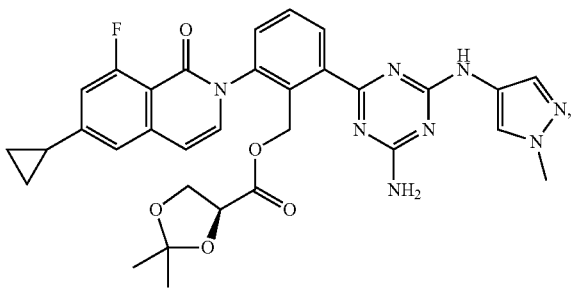 and
or a pharmaceutically acceptable salt thereof.
11. A compound selected from the group consisting of:
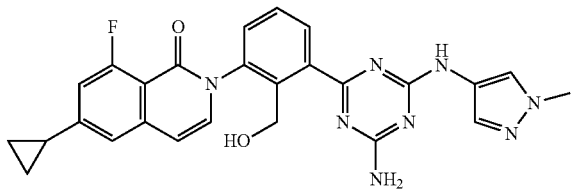
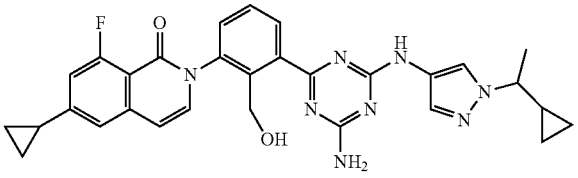
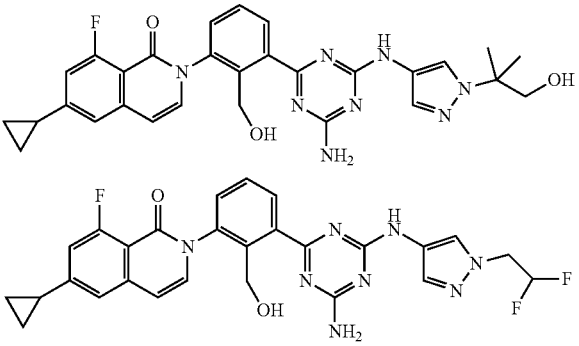

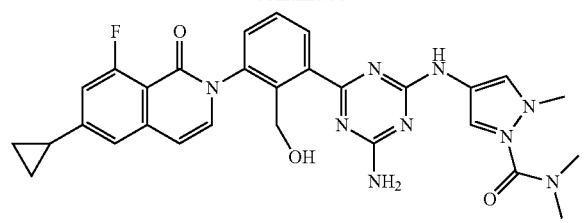
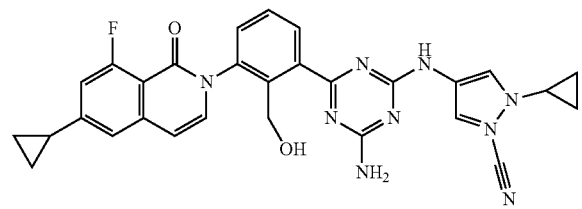
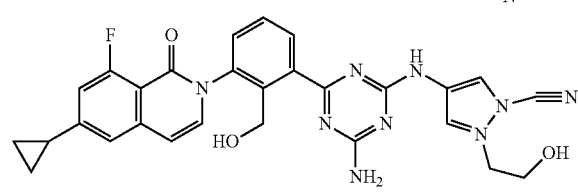
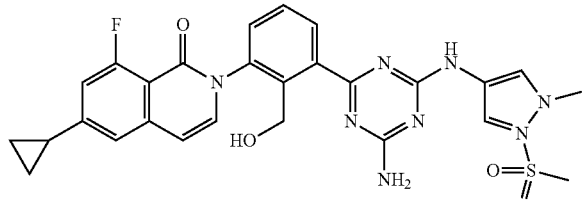
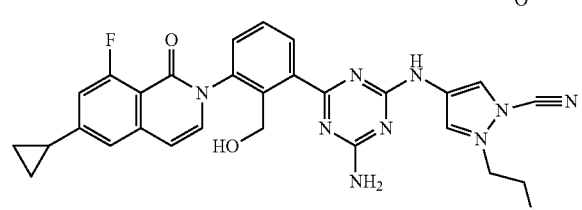
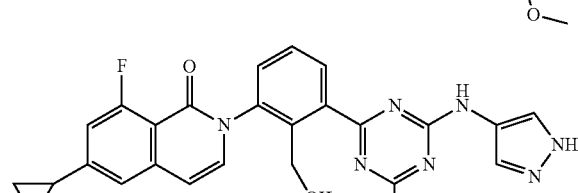
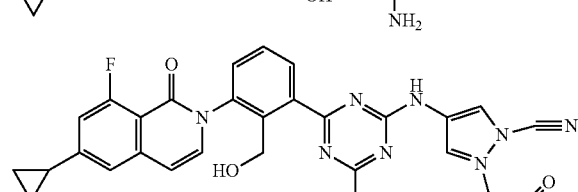
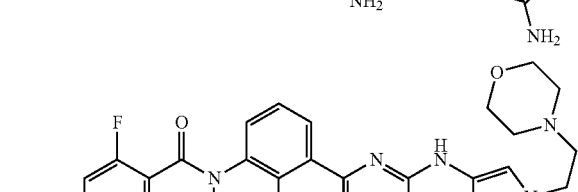
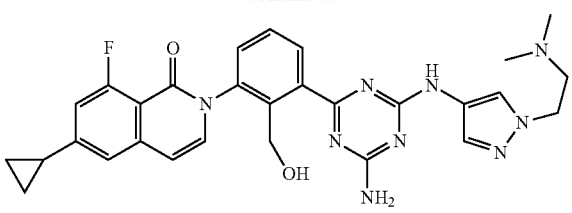
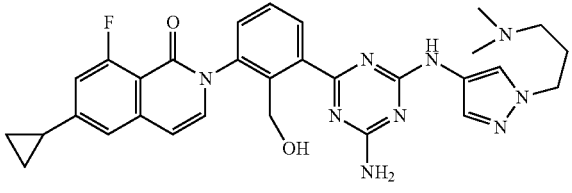
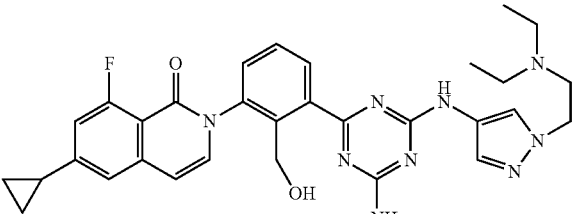
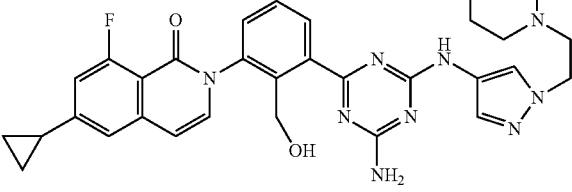
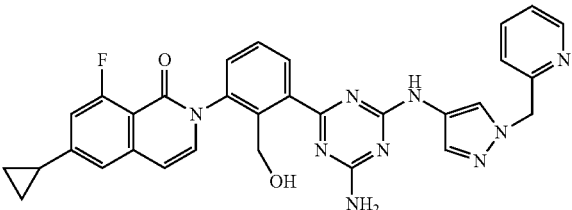
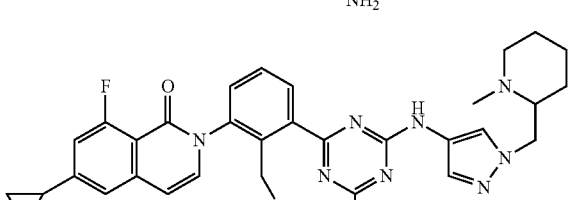
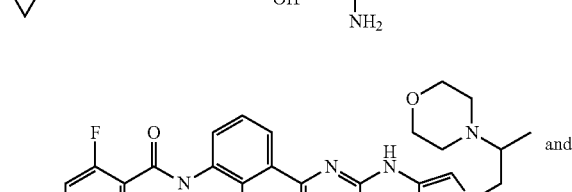

-continued

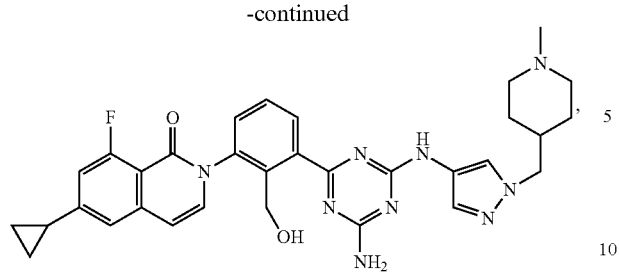

or a pharmaceutically acceptable salt thereof.

12. A pharmaceutical composition comprising the compound according to claim 1, or a pharmaceutically acceptable salt thereof, and a pharmaceutical carrier.

13. A pharmaceutical composition comprising the compound according to claim 10, or a pharmaceutically acceptable salt thereof, and a pharmaceutical carrier.

14. A pharmaceutical composition comprising the compound according to claim 11, or a pharmaceutically acceptable salt thereof, and a pharmaceutical carrier.

* * * * *